(12) United States Patent
Parmee et al.

(10) Patent No.: US 7,563,815 B2
(45) Date of Patent: Jul. 21, 2009

(54) BENZAMIDAZOLES, COMPOSITIONS CONTAINING SUCH COMPOUNDS AND METHODS OF USE

(75) Inventors: Emma R. Parmee, Scotch Plains, NJ (US); Ronald M. Kim, Summit, NJ (US); Rui Liang, East Brunswick, NJ (US); Jiang Chang, Westfield, NJ (US); Elizabeth Ashley Rouse, Edison, NJ (US); Kevin T. Chapman, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 605 days.

(21) Appl. No.: 10/556,230

(22) PCT Filed: May 5, 2004

(86) PCT No.: PCT/US2004/013874

§ 371 (c)(1),
(2), (4) Date: Nov. 9, 2005

(87) PCT Pub. No.: WO2004/098572

PCT Pub. Date: Nov. 18, 2004

(65) Prior Publication Data

US 2007/0093544 A1    Apr. 26, 2007

Related U.S. Application Data

(60) Provisional application No. 60/469,332, filed on May 9, 2003.

(51) Int. Cl.
*A61K 31/4184* (2006.01)
*C07D 235/28* (2006.01)

(52) U.S. Cl. .................. 514/394; 548/305.4; 548/307.1

(58) Field of Classification Search ....................... None
See application file for complete search history.

(56) References Cited

U.S. PATENT DOCUMENTS

| 5,705,515 A | 1/1998 | Fisher et al. | |
|---|---|---|---|
| 6,596,751 B2 * | 7/2003 | Fujita et al. | 514/394 |
| 7,301,036 B2 * | 11/2007 | Parmee et al. | 548/307.4 |

FOREIGN PATENT DOCUMENTS

WO    WO 03/053938    7/2003

* cited by examiner

*Primary Examiner*—Kamal A Saeed
(74) *Attorney, Agent, or Firm*—Richard C. Billups; Catherine D. Fitch

(57) ABSTRACT

The present invention relates to substituted benzimidazoles, compositions containing such compounds and methods of treatment The compounds are glucagon receptor antagonists and thus are useful for treating, preventing or delaying the onset of type 2 diabetes mellitus.

10 Claims, No Drawings

BENZAMIDAZOLES, COMPOSITIONS CONTAINING SUCH COMPOUNDS AND METHODS OF USE

CROSS REFERENCE TO RELATED APPLICATIONS

This application is a U.S. national phase application based upon PCT application No. PCT/US2004/013874 filed on May 5, 2004, which was based upon provisional application Ser. No. 60/469,332 filed on May 9, 2003, priority of which is claimed.

BACKGROUND OF THE INVENTION

The present invention relates to substituted benzimidazole derivatives, compositions containing such compounds and methods of treating type 2 diabetes mellitus.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level $\geq 126$ mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure $\geq 130/80$ mmHg in a resting state), nephropathy, neuropathy and retinopathy.

Patients having type 2 diabetes mellitus characteristically exhibit elevated plasma insulin levels compared with nondiabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by pancreatic islet cells in response to falling blood glucose levels. The hormone binds to specific receptors in liver cells that triggers glycogenolysis and an increase in gluconeogenesis through cAMP-mediated events. These responses generate glucose (e.g. hepatic glucose production) to help maintain euglycemia by preventing blood glucose levels from falling significantly.

In addition to elevated levels of circulating insulin, type II diabetics have elevated levels of plasma glucagon and increased rates of hepatic glucose production. Antagonists of glucagon are useful in improving insulin responsiveness in the liver, decreasing the rate of gluconeogenesis and lowering the rate of hepatic glucose output resulting in a decrease in the levels of plasma glucose.

SUMMARY OF THE INVENTION

The present invention is directed to a compound represented by formula I:

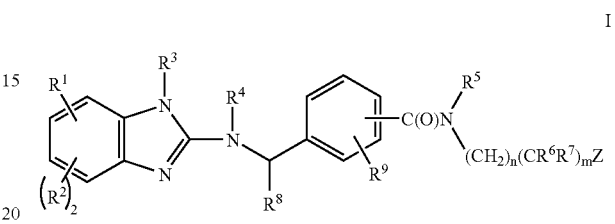

I or a pharmaceutically acceptable salt or solvate thereof, wherein:

$R^1$ represents H or is independently selected from the group consisting of:

a) OH, halo, $CO_2R^a$, $C(O)NR^bR^c$, $NR^bR^c$, CN or $S(O)_pR^d$;

b) $C_{1-10}$alkyl, $C_{2-10}$alkenyl, $C_{2-10}$alkynyl, $OC_{1-10}$alkyl, $OC_{3-10}$alkenyl and $OC_{3-10}$alkynyl, said groups being optionally substituted with: (1) 1-5 halo groups up to a perhaloalkyl group; (2) 1 oxo group; (3) 1-2 OH groups; (4) 1-2 $C_{1-10}$alkoxy groups, each optionally substituted with: up to five halo or a perhaloalkoxy, 1 OH or $CO_2R^a$ group; (5) 1 $CO_2R^a$ or $S(O)_pR^d$; (6) 1-2 Aryl, Hetcy or HAR groups, each optionally substituted as follows: (a) 1-5 halo groups, (b) 1 OH, $CO_2R^a$, CN, $S(O)_pR^d$, $NO_2$ or $C(O)NR^bR^c$ group, (c) 1-2 $C_{1-10}$alkyl or alkoxy groups, each optionally substituted with: 1-5 halo, up to perhaloalkyl, and 1-2 OH or $CO_2R^a$ groups; and (d) 1-2 phenyl rings, each of which is optionally substituted as follows: 1-5 halo groups up to perhalo, 1-3 $C_{1-10}$alkyl or alkoxy groups, each being further optionally substituted with 1-5 halo up to perhalo, or 1-2 hydroxy or $CO_2R^a$ groups; (e) —$NR^a$—C(O)—$NR^bR^c$; (f) —$NR^a$—$CO_2R^c$; (g) —$NR^a$—C(O)$R^c$; (h) —$NR^bR^c$; (i) —$NR^aSO_2R^c$; (j) —$SO_2$—$NR^bR^c$; (k) —$C(O)NR^bR^c$ and (l) —$OC(O)$—$NR^bR^c$;

c) Aryl, HAR, Hetcy, —O-Aryl, —O-HAR and —O-Hetcy, each optionally substituted as set forth below: (1) 1-3 $C_{1-10}$alkyl, $C_{2-10}$alkenyl or $C_{2-10}$alkynyl groups optionally substituted with 1-5 halo groups; 1-2 OH groups; phenyl optionally substituted with 1-3 halo, $C_{1-6}$ alkyl or $C_{1-6}$ alkoxy groups, the alkyl and alkoxy groups being further optionally substituted with 1-3 halo groups; $CO_2R^a$; CN or $S(O)_pR^d$ groups; and (2) 1-3 $C_{1-10}$alkoxy groups, the alkyl portion of which is optionally substituted with 1-5 halo groups, 1-2 OH; phenyl optionally substituted with 1-3 halo, $C_{1-6}$ alkyl or $C_{1-6}$ alkoxy groups, the alkyl and alkoxy groups being further optionally substituted with 1-3 halo groups; $CO_2R^a$; CN or $S(O)_pR^d$ groups;

said Aryl, HAR, Hetcy —O-Aryl, —O-HAR and —O-Hetcy group c) being further optionally substituted on carbon by a group selected from the group consisting of: (3) 1-5 halo groups; (4) 1-2 OH groups; (5) 1 $S(O)_pR^d$, $NO_2$ or CN group; (6) 1-2 $CO_2R^a$; (7) —$NR^a$—C(O)—$NR^bR^c$; (8) —$NR^a$—$CO_2R^c$; (9) —$NR^a$—C(O)$R^c$; (10) —$NR^bR^c$; (11) —$NR^aSO_2R^c$; (12) —$SO_2$—$NR^bR^c$; and (13) —$C(O)NR^bR^c$;

and when $R^1$ represents Hetcy containing a nitrogen atom, said nitrogen atom can be optionally substituted with a member selected from the group consisting of: (a) —C(O)NR$^b$R$^c$; (b) —CO$_2$R$^c$; (c) —C(O)R$^c$; and (d) —SO$_2$R$^c$;

each $R^2$ represents H or is independently selected from the group consisting of:

a) OH, halo, CO$_2$R$^a$, C(O)NR$^b$R$^c$, NR$^b$R$^c$, CN or S(O)$_p$R$^d$;

b) $C_{1-10}$alkyl, $C_{2-10}$alkenyl, $C_{2-10}$alkynyl, OC$_{1-10}$alkyl, OC$_{3-10}$alkenyl and OC$_{3-10}$alkynyl, said groups being optionally substituted with: (1) 1-5 halo groups up to a perhaloalkyl group; (2) 1 oxo group; (3) 1 OH group; (4) 1 $C_{1-10}$alkoxy group, each optionally substituted with: up to five halo or a perhaloalkoxy, 1 OH or CO$_2$R$^a$ group; (5) 1 CO$_2$R$^a$ or S(O)$_p$R$^d$; (6) 1 Aryl, Hetcy or HAR group, each optionally substituted as follows: (a) 1-5 halo groups, (b) 1 OH, CO$_2$R$^a$, CN, S(O)$_p$R$^d$, NO$_2$ or C(O)NR$^b$R$^c$ group, (c) 1-2 $C_{1-10}$alkyl or alkoxy groups, each optionally substituted with: 1-5 halo, up to perhaloalkyl, and 1-2 OH or CO$_2$R$^a$ groups; and (d) 1-2 phenyl rings, each of which is optionally substituted as follows: 1-5 halo groups up to perhalo; 1-3 $C_{1-10}$alkyl or alkoxy groups, each being further optionally substituted with 1-5 halo up to perhalo; and 1-2 hydroxy or CO$_2$R$^a$ groups;

c) Aryl, HAR, Hetcy, —O-Aryl, —O-HAR and —O-Hetcy, each optionally substituted as set forth below: (1) 1-3 $C_{1-10}$alkyl, $C_{2-10}$alkenyl or $C_{2-10}$alkynyl groups optionally substituted with 1-5 halo groups, 1-2 OH, phenyl, CO$_2$R$^a$, CN or S(O)$_p$R$^d$ groups; (2) 1-3 $C_{1-10}$alkoxy groups, the alkyl portion of which is optionally substituted with 1-5 halo groups, 1-2 OH, phenyl, CO$_2$R$^a$, CN or S(O)$_p$R$^d$ groups;

said Aryl, HAR or Hetcy group c) being further optionally substituted on carbon by a group selected from the group consisting of: (3) 1-5 halo groups up to perhalo; (4) 1 OH group; (5) 1S(O)$_p$R$^d$, NO$_2$ or CN group; and (6) 1 CO$_2$R$^a$;

$R^3$ represents H or is selected from the group consisting of:
a) $C_{1-10}$alkyl or $C_{2-10}$alkenyl, each optionally substituted with 1-5 halo groups up to perhalo; 1-2 OH, $C_{1-3}$alkoxy or haloC$_{1-3}$ alkoxy groups; 1-2NR$^c$R$^d$ groups; and 1-2 Aryl, HAR or Hetcy groups, each optionally substituted with 1-3 halo groups and 1-2 groups selected from CN, NO$_2$, $C_{1-3}$alkyl, haloC$_{1-3}$alkyl, $C_{1-3}$alkoxy and haloC$_{1-3}$ alkoxy groups; and b) Aryl, HAR or Hetcy, each optionally substituted with 1-3 halo groups and 1-2 groups selected from CN, NO$_2$, $C_{1-3}$alkyl, haloC$_{1-3}$alkyl, $C_{1-3}$alkoxy and haloC$_{1-3}$ alkoxy groups;

$R^4$ is independently selected from the group consisting of:

a) $C_{1-14}$alkyl, $C_{2-10}$alkenyl and $C_{2-10}$alkynyl, said groups being optionally substituted with: (1) 1-5 halo groups up to perhaloalkyl; (2) 1 oxo group; (3) 1-2 OH groups; (4) 1-2 $C_{1-10}$alkoxy groups, each optionally substituted with up to five halo or a perhaloalkoxy, 1 OH or CO$_2$R$^a$ group; (5) 1 CO$_2$R$^a$ or S(O)$_p$R$^d$; (6) 1-2 Aryl, Hetcy or HAR groups, each optionally substituted as follows: (i) 1-5 halo groups, (ii) 1 OH, CO$_2$R$^a$, CN, S(O)$_p$R$^d$, NO$_2$ or C(O)NR$^b$R$^c$ group, (iii) 1-2 $C_{1-10}$alkyl or alkoxy groups, each optionally substituted with: 1-5 halo, up to perhaloalkyl, and 1-2 OH or CO$_2$R$^a$ groups; and (iv) 1-2 phenyl rings, each of which is optionally substituted as follows: 1-5 halo groups up to perhalo; 1-3 $C_{1-10}$alkyl or alkoxy groups, each being further optionally substituted with 1-5 halo up to perhalo, or 1-2 hydroxy or CO$_2$R$^a$ groups;

b) Aryl, HAR or Hetcy, each optionally substituted as follows: (1) 1-3 $C_{1-14}$alkyl, $C_{2-10}$alkenyl or $C_{2-10}$alkynyl groups optionally substituted with 1-5 halo groups, 1-2 OH, CO$_2$R$^a$, CN or S(O)$_p$R$^d$ groups or phenyl optionally substituted as follows: 1-5 halo groups up to perhalo; 1-3 $C_{1-10}$alkyl or alkoxy groups, each being further optionally substituted with 1-5 halo up to perhalo, or 1-2 hydroxy or CO$_2$R$^a$ groups;

(2) 1-3 $C_{1-10}$alkoxy groups, the alkyl portion of which is optionally substituted with 1-5 halo groups, 1-2 OH, CO$_2$R$^a$, CN, S(O)$_p$R$^d$, and phenyl optionally substituted as follows: 1-5 halo groups up to perhalo; 1-3 $C_{1-10}$alkyl or alkoxy groups, each being further optionally substituted with 1-5 halo up to perhalo, or 1-2 hydroxy or CO$_2$R$^a$ groups; (3) 1-2 Aryl, HAR or Hetcy, OAryl, OHAR or OHetcy groups, each optionally substituted as follows: (i) 1-3 halo groups; (ii) 1-2 $C_{1-10}$alkyl, $C_{2-10}$alkenyl or $C_{2-10}$alkynyl groups each optionally substituted with 1-5 halo groups, 1-2 OH, phenyl, CO$_2$R$^a$, CN or S(O)$_p$R$^d$ groups; (iii) 1-2 $C_{1-10}$alkoxy groups the alkyl portion of which being optionally substituted with 1-5 halo groups, 1-2 OH, phenyl, CO$_2$R$^a$, CN or S(O)$_p$R$^d$ groups; and (iv) 1-2 CO$_2$R$^a$, S(O)$_p$R$^d$, CN, NR$^b$R$^c$, NO$_2$ or OH groups;

said Aryl, HAR or Hetcy group b) being further optionally substituted on carbon by a group selected from the group consisting of: (4) 1-5 halo groups; (5) 1-2 OH groups; (6) 1 S(O)$_p$R$^d$, NO$_2$ or CN group; (7) 1-2 CO$_2$R$^a$; (8) —NR$^a$—C(O)—NR$^b$R$^c$; (9) —NR$^a$—CO$_2$R$^c$; (10) —NR$^a$—C(O)R$^c$; (11) —NR$^b$R$^c$; (12) —NR$^a$SO$_2$R$^c$; (13) —SO$_2$—NR$^b$R$^c$; (14) —C(O)NR$^b$R$^c$ and —OC(O)—NR$^b$R$^c$;

and when $R^4$ represents Hetcy containing a nitrogen atom, said nitrogen atom can be optionally substituted with a member selected from the group consisting of: (a) —C(O)NR$^b$R$^c$; (b) —CO$_2$R$^c$; (c) —C(O)R$^c$; and (d) —SO$_2$R$^c$;

$R^5$ represents H or $C_{1-6}$ alkyl;

$R^6$ is selected from the group consisting of H, OH, F or $C_{1-3}$alkyl;

$R^7$ is H or F, or $R^6$ and $R^7$ are taken in combination and represent oxo;

$R^8$ represents H or $C_{1-6}$ alkyl, optionally substituted with OH and 1-5 halo groups up to perhalo;

$R^9$ represents H, halo, OH, $C_{1-6}$alkyl, optionally substituted with 1-5 halo groups up to perhalo, or $C_{1-6}$alkoxy, optionally substituted with 1-3 halo groups up to perhalo, or when $R^9$ is ortho to the benzylic group, $R^8$ and $R^9$ can be taken together and represent a —(CH$_2$)$_{2-4}$— or a —O—(CH$_2$)$_{1-3}$ group;

$R^a$ is H or $C_{1-10}$alkyl, optionally substituted with phenyl, OH, OC$_{1-6}$alkyl, CO$_2$H, CO$_2$C$_{1-6}$alkyl and 1-3 halo groups;

$R^b$ is H or $C_{1-10}$alkyl;

$R^c$ is H or is independently selected from: (a) $C_{1-10}$alkyl, optionally substituted with OH, OC$_{1-6}$alkyl, CO$_2$H, CO$_2$C$_{1-6}$ alkyl, and 1-3 halo groups; (b) Aryl or Ar—C$_{1-6}$alkyl, each optionally substituted with 1-5 halos and 1-3 members selected from the group consisting of: CN, OH, $C_{1-10}$alkyl and OC$_{1-10}$ alkyl, said alkyl and alkoxy being further optionally substituted with 1-5 halo groups up to perhalo; (c) Hetcy or Hetcy-C$_{1-6}$alkyl, optionally substituted with 1-5 halo groups and 1-3 groups selected from: oxo, $C_{1-10}$alkyl and OC$_{1-10}$ alkyl, said alkyl and alkoxy being further optionally substituted with 1-5 halo groups up to perhalo; and (d) HAR or HAR-C$_{1-6}$alkyl, optionally substituted with 1-5 halo groups and 1-3 groups selected from: $C_{1-10}$alkyl and OC$_{1-10}$ alkyl, said alkyl and alkoxy being further optionally substituted with 1-5 halo groups up to perhalo;

$R^d$ is $C_{1-10}$alkyl, Aryl or Ar—C$_{1-10}$alkyl;

m is an integer selected from 0, 1 and 2;

n is an integer selected from 0 to 6;

p is an integer selected from 0, 1 and 2, and when at least one of m and n is other than 0, Z is selected from CO$_2$R$^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl).

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Aryl" (Ar) means mono- and bicyclic aromatic rings containing 6-12 carbon atoms. Examples of aryl include phenyl, naphthyl, indenyl and the like.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings. Heteroaryl also includes such groups in charged form, e.g., pyridinium.

"Heterocyclyl" (Hetcy) means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2,3-b)pyridyl, benzoxazinyl, tetrahydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils). Heterocyclyl moreover includes such moieties in charged form, e.g., piperidinium.

"Halogen" (Halo) includes fluorine, chlorine, bromine and iodine, preferably F and Cl, more preferably F.

In one aspect, the invention is directed to a compound represented by formula I:

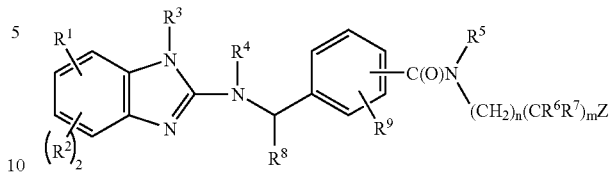

or a pharmaceutically acceptable salt or solvate thereof, wherein:

$R^1$ represents H or is independently selected from the group consisting of:

a) OH, halo, $CO_2R^a$, $C(O)NR^bR^c$, $NR^bR^c$, CN or $S(O)_pR^d$;

b) $C_{1-10}$alkyl, $C_{2-10}$alkenyl, $C_{2-10}$alkynyl, $OC_{1-10}$alkyl, $OC_{3-10}$alkenyl and $OC_{3-10}$alkynyl, said groups being optionally substituted with: (1) 1-5 halo groups up to a perhaloalkyl group; (2) 1 oxo group; (3) 1-2 OH groups; (4) 1-2 $C_{1-10}$alkoxy groups, each optionally substituted with: up to five halo or a perhaloalkoxy, 1 OH or $CO_2R^a$ group; (5) 1 $CO_2R^a$ or $S(O)_pR^d$; (6) 1-2 Aryl, Hetcy or HAR groups, each optionally substituted as follows: (a) 1-5 halo groups, (b) 1 OH, $CO_2R^a$, CN, $S(O)_pR^d$, $NO_2$ or $C(O)NR^bR^c$ group, (c) 1-2 $C_{1-10}$alkyl or alkoxy groups, each optionally substituted with: 1-5 halo, up to perhaloalkyl, and 1-2 OH or $CO_2R^a$ groups; and (d) 1-2 phenyl rings, each of which is optionally substituted as follows: 1-5 halo groups up to perhalo, 1-3 $C_{1-10}$alkyl or alkoxy groups, each being further optionally substituted with 1-5 halo up to perhalo, or 1-2 hydroxy or $CO_2R^a$ groups; (e) —$NR^a$—$C(O)$—$NR^bR^c$; (f) —$NR^a$—$CO_2R^c$; (g) —$NR^a$—$C(O)R^c$; (h) —$NR^bR^c$; (i) —$NR^aSO_2R^c$; (j) —$SO_2$—$NR^bR^c$; (k) —$C(O)NR^bR^c$ and (l) —$OC(O)$—$NR^bR^c$;

c) Aryl, HAR, Hetcy, —O-Aryl, —O-HAR and —O-Hetcy, each optionally substituted as set forth below: (1) 1-3 $C_{1-10}$alkyl, $C_{2-10}$alkenyl or $C_{2-10}$alkynyl groups optionally substituted with 1-5 halo groups; 1-2 OH groups; phenyl optionally substituted with 1-3 halo, $C_{1-6}$ alkyl or $C_{1-6}$ alkoxy groups, the alkyl and alkoxy groups being further optionally substituted with 1-3 halo groups; $CO_2R^a$; CN or $S(O)_pR^d$ groups; and (2) 1-3 $C_{1-10}$alkoxy groups, the alkyl portion of which is optionally substituted with 1-5 halo groups, 1-2 OH; phenyl optionally substituted with 1-3 halo, $C_{1-6}$ alkyl or $C_{1-6}$ alkoxy groups, the alkyl and alkoxy groups being further optionally substituted with 1-3 halo groups; $CO_2R^a$; CN or $S(O)_pR^d$ groups;

said Aryl, HAR, Hetcy —O-Aryl, —O-HAR and —O-Hetcy group c) being further optionally substituted on carbon by a group selected from the group consisting of: (3) 1-5 halo groups; (4) 1-2 OH groups; (5) 1 $S(O)_pR^d$, $NO_2$ or CN group; (6) 1-2 $CO_2R^a$; (7) —$NR^a$—$C(O)$—$NR^bR^c$; (8) —$NR^a$—$CO_2R^c$; (9) —$NR^a$—$C(O)R^c$; (10) —$NR^bR^c$; (11) —$NR^aSO_2R^c$; (12) —$SO_2$—$NR^bR^c$; and (13) —$C(O)NR^bR^c$; and when $R^1$ represents Hetcy containing a nitrogen atom, said nitrogen atom can be optionally substituted with a member selected from the group consisting of: (a) —$C(O)NR^bR^c$; (b) —$CO_2R^c$; (c) —$C(O)R^c$; and (d) —$SO_2R^c$;

each $R^2$ represents H or is independently selected from the group consisting of:

a) OH, halo, $CO_2R^a$, $C(O)NR^bR^c$, $NR^bR^c$, CN or $S(O)_pR^d$;

b) $C_{1-10}$alkyl, $C_{2-10}$alkenyl, $C_{2-10}$alkynyl, $OC_{1-10}$alkyl, $OC_{3-10}$alkenyl and $OC_{3-10}$alkynyl, said groups being optionally substituted with: (1) 1-5 halo groups up to a perhaloalkyl group; (2) 1 oxo group; (3) 1 OH group; (4) 1 $C_{1-10}$alkoxy group, each optionally substituted with: up to five halo or a perhaloalkoxy, 1 OH or $CO_2R^a$ group; (5) 1 $CO_2R^a$ or $S(O)_pR^d$; (6) 1 Aryl, Hetcy or HAR group, each optionally substituted as follows: (a) 1-5 halo groups, (b) 1 OH, $CO_2R^a$, CN, $S(O)_pR^d$, $NO_2$ or $C(O)NR^bR^c$ group, (c) 1-2 $C_{1-10}$alkyl or alkoxy groups, each optionally substituted with: 1-5 halo, up to perhaloalkyl, and 1-2 OH or $CO_2R^a$ groups; and (d) 1-2 phenyl rings, each of which is optionally substituted as follows: 1-5 halo groups up to perhalo; 1-3 $C_{1-10}$alkyl or alkoxy groups, each being further optionally substituted with 1-5 halo up to perhalo; and 1-2 hydroxy or $CO_2R^a$ groups;

c) Aryl, HAR, Hetcy, —O-Aryl, —O-HAR and —O-Hetcy, each optionally substituted as set forth below: (1) 1-3 $C_{1-10}$alkyl, $C_{2-10}$alkenyl or $C_{2-10}$alkynyl groups optionally substituted with 1-5 halo groups, 1-2 OH, phenyl, $CO_2R^a$, CN or $S(O)_pR^d$ groups; (2) 1-3 $C_{1-10}$alkoxy groups, the alkyl portion of which is optionally substituted with 1-5 halo groups, 1-2 OH, phenyl, $CO_2R^a$, CN or $S(O)_pR^d$ groups;

said Aryl, HAR or Hetcy group c) being further optionally substituted on carbon by a group selected from the group consisting of; (3) 1-5 halo groups up to perhalo; (4) 1 OH group; (5) 1 $S(O)_pR^d$, $NO_2$ or CN group; (6) 1 $CO_2R^a$;

$R^3$ represents H or is selected from the group consisting of:
a) $C_{1-10}$alkyl or $C_{2-10}$alkenyl, each optionally substituted with 1-5 halo groups up to perhalo; 1-2 OH, $C_{1-3}$alkoxy or halo$C_{1-3}$ alkoxy groups; 1-2 $NR^cR^d$ groups; and 1-2 Aryl, HAR or Hetcy groups, each optionally substituted with 1-3 halo groups and 1-2 groups selected from CN, $NO_2$, $C_{1-3}$alkyl, halo$C_{1-3}$alkyl, $C_{1-3}$alkoxy and halo$C_{1-3}$ alkoxy groups; and b) Aryl, HAR or Hetcy, each optionally substituted with 1-3 halo groups and 1-2 groups selected from CN, $NO_2$, $C_{1-3}$alkyl, halo$C_{1-3}$alkyl, $C_{1-3}$alkoxy and halo$C_{1-3}$ alkoxy groups;

$R^4$ is independently selected from the group consisting of:
a) $C_{1-14}$alkyl, $C_{2-10}$alkenyl and $C_{2-10}$alkynyl, said groups being optionally substituted with: (1) 1-5 halo groups up to perhaloalkyl; (2) 1 oxo group; (3) 1-2 OH groups; (4) 1-2 $C_{1-10}$alkoxy groups, each optionally substituted with up to five halo or a perhaloalkoxy, 1 OH or $CO_2R^a$ group; (5) 1 $CO_2R^a$ or $S(O)_pR^d$; (6) 1-2 Aryl, Hetcy or HAR groups, each optionally substituted as follows: (i) 1-5 halo groups, (ii) 1 OH, $CO_2R^a$, CN, $S(O)_pR^d$, $NO_2$ or $C(O)NR^bR^c$ group, (iii) 1-2 $C_{1-10}$alkyl or alkoxy groups, each optionally substituted with: 1-5 halo, up to perhaloalkyl, and 1-2 OH or $CO_2R^a$ groups; and (iv) 1-2 phenyl rings, each of which is optionally substituted as follows: 1-5 halo groups up to perhalo; 1-3 $C_{1-10}$alkyl or alkoxy groups, each being further optionally substituted with 1-5 halo up to perhalo, or 1-2 hydroxy or $CO_2R^a$ groups;

b) Aryl, HAR or Hetcy, each optionally substituted as follows: (1) 1-3 $C_{1-14}$alkyl, $C_{2-10}$alkenyl or $C_{2-10}$alkynyl groups optionally substituted with 1-5 halo groups, 1-2 OH, $CO_2R^a$, CN or $S(O)_pR^d$, groups or phenyl optionally substituted as follows: 1-5 halo groups up to perhalo; 1-3 $C_{1-10}$alkyl or alkoxy groups, each being further optionally substituted with 1-5 halo up to perhalo, or 1-2 hydroxy or $CO_2R^a$ groups;

(2) 1-3 $C_{1-10}$alkoxy groups, the alkyl portion of which is optionally substituted with 1-5 halo groups, 1-2 OH, $CO_2R^a$, CN, $S(O)_pR^d$, and phenyl optionally substituted as follows: 1-5 halo groups up to perhalo; 1-3 $C_{1-10}$alkyl or alkoxy groups, each being further optionally substituted with 1-5 halo up to perhalo, or 1-2 hydroxy or $CO_2R^a$ groups; (3) 1-2 Aryl, HAR or Hetcy, OAryl, OHAR or OHetcy groups, each optionally substituted as follows: (i) 1-3 halo groups; (ii) 1-2 $C_{1-10}$alkyl, $C_{2-10}$alkenyl or $C_{2-10}$alkynyl groups each optionally substituted with 1-5 halo groups, 1-2 OH, phenyl, $CO_2R^a$, CN or $S(O)_pR^d$ groups; (iii) 1-2 $C_{1-10}$alkoxy groups the alkyl portion of which being optionally substituted with 1-5 halo groups, 1-2 OH, phenyl, $CO_2R^a$, CN or $S(O)_pR^d$ groups; and (iv) 1-2 $CO_2R^a$, $S(O)_pR^d$, CN, $NR^bR^c$, $NO_2$ or OH groups;

said Aryl, HAR or Hetcy group b) being further optionally substituted on carbon by a group selected from the group consisting of: (4) 1-5 halo groups; (5) 1-2 OH groups; (6) 1 $S(O)_pR^d$, $NO_2$ or CN group; (7) 1-2 $CO_2R^a$; (8) —$NR^a$—$C(O)$—$NR^bR^c$; (9) —$NR^a$—$CO_2R^c$; (10) —$NR^a$—$C(O)R^c$; (11) —$NR^bR^c$; (12) —$NR^aSO_2R^c$; (13) —$SO_2$—$NR^bR^c$; (14) —$C(O)NR^bR^c$ and —$OC(O)$—$NR^bR^c$;

and when $R^4$ represents Hetcy containing a nitrogen atom, said nitrogen atom can be optionally substituted with a member selected from the group consisting of: (a) —$C(O)NR^bR^c$; (b) —$CO_2R^c$; (c) —$C(O)R^c$; and (d) —$SO_2R^c$;

$R^5$ represents H or $C_{1-6}$alkyl;

$R^6$ is selected from the group consisting of H, OH, F or $C_{1-3}$alkyl;

$R^7$ is H or F, or $R^6$ and $R^7$ are taken in combination and represent oxo;

$R^8$ represents H or $C_{1-6}$ alkyl, optionally substituted with OH and 1-5 halo groups up to perhalo;

$R^9$ represents H, halo, OH, $C_{1-6}$alkyl, optionally substituted with 1-5 halo groups up to perhalo, or $C_{1-6}$alkoxy, optionally substituted with 1-3 halo groups up to perhalo, or when $R^9$ is ortho to the benzylic group, $R^8$ and $R^9$ can be taken together and represent a —$(CH_2)_{2-4}$— or a —O—$(CH_2)_{1-3}$— group;

$R^a$ is H or $C_{1-10}$alkyl, optionally substituted with phenyl, OH, $OC_{1-6}$alkyl, $CO_2H$, $CO_2C_{1-6}$alkyl and 1-3 halo groups;

$R^b$ is H or $C_{1-10}$alkyl;

$R^c$ is H or is independently selected from: (a) $C_{1-10}$alkyl, optionally substituted with OH, $OC_{1-6}$alkyl, $CO_2H$, $CO_2C_{1-6}$ alkyl, and 1-3 halo groups; (b) Aryl or Ar—$C_{1-6}$alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo; (c) Hetcy or Hetcy-$C_{1-6}$alkyl, optionally substituted with 1-5 halo groups and 1-3 groups selected from: oxo, $C_{1-10}$alkyl and $OC_{1-10}$ alkyl, said alkyl and alkoxy being further optionally substituted with 1-5 halo groups up to perhalo; and (d) HAR or HAR-$C_{1-6}$alkyl, optionally substituted with 1-5 halo groups and 1-3 groups selected from: $C_{1-10}$alkyl and $OC_{1-10}$ alkyl, said alkyl and alkoxy being further optionally substituted with 1-5 halo groups up to perhalo;

$R^d$ is $C_{1-10}$alkyl, Aryl or Ar—$C_{1-10}$alkyl;

m is an integer selected from 0, 1 and 2;

n is an integer selected from 0 to 6;

p is an integer selected from 0, 1 and 2, and when at least one of m and n is other than 0, Z is selected from $CO_2R^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl).

One aspect of the invention that is of interest relates to a compound of formula I or a pharmaceutically acceptable salt or solvate thereof wherein $R^1$ represents H. Within this aspect of the invention, all other variables are as originally defined with respect to formula I.

Another aspect of the invention that is of interest relates to a compound of formula I or a pharmaceutically acceptable salt or solvate thereof wherein one $R^2$ represents H, halo or $C_{1-6}$alkyl, and the other is selected from the group consisting of: H, halo, OH, $C_{1-6}$alkyl optionally substituted with 1-3 halo groups, $C_{1-6}$alkoxy optionally substituted with 1-3 halo groups or 1 phenyl or heterocyclic ring, $C_{2-4}$alkenyl or $OC_{2-4}$alkenyl. Within this aspect of the invention, all other variables are as originally defined with respect to formula I.

Another aspect of the invention that is of interest relates to a compound of formula I or a pharmaceutically acceptable salt or solvate thereof wherein $R^3$ is selected from the group consisting of: H, $C_{2-4}$alkenyl and $C_{1-6}$alkyl optionally substituted as follows: a) up to 3 halo groups; b) $NR^cR^d$ wherein $R^c$ and $R^d$ are H or $C_{1-4}$ alkyl; c) OH; and d) Aryl optionally substituted with 1-3 halo groups, $C_{1-3}$ alkyl, $OC_{1-3}$alkyl, CN, $NO_2$, halo$C_{1-3}$alkyl or O-halo$C_{1-3}$alkyl. Within this aspect of the invention, all other variables are as originally defined with respect to formula I.

Another aspect of the invention that is of interest relates to a compound of formula I or a pharmaceutically acceptable salt or solvate thereof wherein $R^4$ is independently selected from the group consisting of:

(a) $C_{1-14}$alkyl, optionally substituted with: (1) 1-5 halo groups up to perhaloalkyl; (2) 1-2$C_{1-10}$alkoxy groups, each optionally substituted with 1-5 halo groups up to perhaloalkoxy; (3) 1-2 Aryl groups, each optionally substituted as follows: (i) 1-5 halo groups, (ii) CN or $NO_2$, (iii) 1-2 $C_{1-10}$alkyl or alkoxy groups, each optionally substituted with: 1-5 halo, up to perhaloalkyl; and (b) Aryl, HAR or Hetcy, each optionally substituted as follows: (1) 1-2 $C_{1-10}$alkyl or $C_{2-10}$alkenyl groups, optionally substituted with 1-5 halo groups, phenyl or $CO_2R^a$ groups; (2) 1-2 $C_{1-10}$alkoxy groups, the alkyl portion of which is optionally substituted with 1-5 halo groups; (3) 1-2 Aryl, HAR or Hetcy, OAryl, OHAR or OHetcy groups, each optionally substituted as follows: (i) 1-3 halo groups; (ii) 1-2 $C_{1-10}$alkyl or $C_{2-10}$alkenyl, each optionally substituted with 1-3 halo groups; (iii) 1-2 $C_{1-10}$alkoxy groups the alkyl portion of which being optionally substituted with 1-3 halo groups, and (iv) 1-2 $CO_2R^a$, $S(O)_pR^d$, CN, $NR^bR^c$, $NO_2$ or OH groups;

said Aryl, HAR or Hetcy group b) being further optionally substituted on carbon by a group selected from the group consisting of: (4) 1-5 halo groups; (5) 1-2 OH groups; (6) 1 $S(O)_pR^d$, $NO_2$ or CN group; (7) 1-2 $CO_2R^a$; (8) —$NR^a$—C(O)—$NR^bR^c$; (9) —$NR^a$—$CO_2R^c$; (10) —$NR^a$—$C(O)R^c$; (11) —$NR^bR^c$; (12) —$NR^aSO_2R^c$; (13) —$SO_2$—$NR^bR^c$; (14) —$C(O)NR^bR^c$ and (15) —$OC(O)$—$NR^bR^c$;

and when $R^4$ represents Hetcy containing a nitrogen atom, said nitrogen atom can be optionally substituted with a member selected from the group consisting of: (a) —$C(O)NR^bR^c$; (b) —$CO_2R^c$; (c) —$C(O)R^c$; and (d) —$SO_2R^c$. Within this aspect of the invention, all other variables are as originally defined with respect to formula I.

Another aspect of the invention that is of interest relates to a compound of formula I or a pharmaceutically acceptable salt or solvate thereof wherein $R^a$ represents H or $C_{1-6}$ alkyl. More particularly, $R^8$ represents H or methyl. Within these aspects of the invention, all other variables are as originally defined with respect to formula I.

Another aspect of the invention that is of interest relates to a compound of formula I or a pharmaceutically acceptable salt or solvate thereof wherein $R^9$ represents H or halo. Within this aspect of the invention, all other variables are as originally defined with respect to formula I.

Yet another aspect of the invention that is of interest relates to a compound of formula I or a pharmaceutically acceptable salt or solvate thereof wherein $R^8$ and $R^9$ are taken in combination and represent —$(CH_2)_{2-4}$—. More particularly, an aspect of the invention that is of interest relates to a compound of formula I or a pharmaceutically acceptable salt or solvate thereof wherein $R^8$ and $R^9$ are taken in combination and represent ethylene. Within these aspects of the invention, all other variables are as originally defined with respect to formula I.

More particularly, an aspect of the invention that is of interest relates to a compound of formula I or a pharmaceutically acceptable salt or solvate thereof wherein $R^1$ represents H;

one $R^2$ represents H, halo or $C_{1-6}$alkyl, and the other is selected from the group consisting of: H, halo, OH, $C_{1-6}$alkyl optionally substituted with 1-3 halo groups, $C_{1-6}$alkoxy optionally substituted with 1-3 halo groups or 1 phenyl or heterocyclic ring, $C_{2-4}$alkenyl or $OC_{2-4}$alkenyl;

$R^3$ is selected from the group consisting of: H, $C_{2-4}$alkenyl and $C_{1-6}$alkyl optionally substituted as follows: a) up to 3 halo groups; b) $NR^cR^d$ wherein $R^c$ and $R^d$ are H or $C_{1-4}$ alkyl; c) OH; and d) Aryl optionally substituted with 1-3 halo groups, $C_{1-3}$ alkyl, $OC_{1-3}$alkyl, CN, $NO_2$, halo$C_{1-3}$alkyl or O-halo$C_{1-3}$ alkyl;

$R^4$ is independently selected from the group consisting of:

(a) $C_{1-14}$alkyl, optionally substituted with: (1) 1-5 halo groups up to perhaloalkyl; (2) 1-2 $C_{1-10}$alkoxy groups, each optionally substituted with 1-5 halo groups up to perhaloalkoxy; (3) 1-2 Aryl groups, each optionally substituted as follows: (i) 1-5 halo groups, (ii) CN or $NO_2$, (iii) 1-2 $C_{1-10}$alkyl or alkoxy groups, each optionally substituted with: 1-5 halo, up to perhaloalkyl; and (b) Aryl, HAR or Hetcy, each optionally substituted as follows: (1) 1-2 $C_{1-10}$alkyl or $C_{2-10}$alkenyl, optionally substituted with 1-5 halo groups, phenyl or $CO_2R^a$ groups; (2) 1-2 $C_{1-10}$alkoxy groups, the alkyl portion of which is optionally substituted with 1-5 halo groups; (3) 1-2 Aryl, HAR or Hetcy, OAryl, OHAR or OHetcy groups, each optionally substituted as follows: (i) 1-3 halo groups; (ii) 1-2 $C_{1-10}$alkyl or $C_{2-10}$alkenyl, each optionally substituted with 1-3 halo groups; (iii) 1-2 $C_{1-10}$alkoxy groups the alkyl portion of which being optionally substituted with 1-3 halo groups, and (iv) 1-2 $CO_2R^a$, $S(O)_pR^d$, CN, $NR^bR^c$, $NO_2$ or OH groups;

said Aryl, HAR or Hetcy group b) being further optionally substituted on carbon by a group selected from the group consisting of: (4) 1-5 halo groups; (5) 1-2 OH groups; (6) 1 $S(O)_pR^d$, $NO_2$ or CN group; (7) 1-2 $CO_2R^a$; (8) —$NR^a$—C (O)—NR$^b$R$^c$; (9) —NR$^a$—CO$_2$R$^c$; (10) —NR$^a$—C(O)R$^c$; (11) —NR$^b$R$^c$; (12) —NR$^a$SO$_2$R$^c$; (13) —SO$_2$—NR$^b$R$^c$; (14) —C(O)NR$^b$R$^c$ and (15) —OC(O)—NR$^b$R$^c$;

and when R$^4$ represents Hetcy containing a nitrogen atom, said nitrogen atom can be optionally substituted with a member selected from the group consisting of: (a) —C(O)NR$^b$R$^c$; (b) —CO$_2$R$^c$; (c) —C(O)R$^c$; and (d) —SO$_2$R$^c$;

R$^8$ represents H or C$_{1-6}$ alkyl;
R$^9$ represents H or halo;
R$^5$ represents H or C$_{1-6}$ alkyl;
R$^6$ is selected from the group consisting of H, OH, F or C$_{1-3}$alkyl;
R$^7$ is H or F, or R$^6$ and R$^7$ are taken in combination and represent oxo;
R$^a$ is H or C$_{1-10}$alkyl, optionally substituted with phenyl, OH, OC$_{1-6}$alkyl, CO$_2$H, CO$_2$C$_{1-6}$alkyl and 1-3 halo groups;
R$^b$ is H or C$_{1-10}$alkyl;
R$^c$ is H or is independently selected from: (a) C$_{1-10}$alkyl, optionally substituted with OH, OC$_{1-6}$alkyl, CO$_2$H, CO$_2$C$_{1-6}$ alkyl, and 1-3 halo groups; (b) Aryl or Ar—C$_{1-6}$alkyl, each optionally substituted with 1-5 halos and 1-3 members selected from the group consisting of: CN, OH, C$_{1-10}$alkyl and OC$_{1-10}$alkyl, said alkyl and alkoxy being further optionally substituted with 1-5 halo groups up to perhalo; (c) Hetcy or Hetcy-C$_{1-6}$alkyl, optionally substituted with 1-5 halo groups and 1-3 groups selected from: oxo, C$_{1-10}$alkyl and OC$_{1-10}$alkyl, said alkyl and alkoxy being further optionally substituted with 1-5 halo groups up to perhalo; and (d) HAR or HAR-C$_{1-6}$alkyl, optionally substituted with 1-5 halo groups and 1-3 groups selected from: C$_{1-10}$alkyl and OC$_{1-10}$ alkyl, said alkyl and alkoxy being further optionally substituted with 1-5 halo groups up to perhalo;

R$^d$ is C$_{1-10}$alkyl, Aryl or Ar—C$_{1-10}$alkyl;
m is an integer selected from 0, 1 and 2;
n is an integer selected from 0 to 6;
p is an integer selected from 0, 1 and 2, and
when at least one of m and n is other than 0, Z is selected from CO$_2$R$^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl). Within this aspect of the invention, all other variables are as originally defined with respect to formula I.

Another more particular aspect of the invention that is of interest relates to a compound of formula I or a pharmaceutically acceptable salt or solvate thereof wherein:

R$^1$ represents H;
one R$^2$ represents H, halo or C$_{1-6}$alkyl, and the other is selected from the group consisting of: H, halo, OH, C$_{1-6}$alkyl optionally substituted with 1-3 halo groups, C$_{1-6}$alkoxy optionally substituted with 1-3 halo groups or 1 phenyl or heterocyclic ring, C$_{2-4}$alkenyl or OC$_{2-4}$alkenyl;
R$^3$ is selected from the group consisting of: H, C$_{2-4}$alkenyl and C$_{1-6}$alkyl optionally substituted as follows: a) up to 3 halo groups; b) NR$^c$R$^d$ wherein R$^c$ and R$^d$ are H or C$_{1-4}$ alkyl; c) OH; and d) Aryl optionally substituted with 1-3 halo groups, C$_{1-3}$ alkyl, OC$_{1-3}$alkyl, CN, NO$_2$, haloC$_{1-3}$alkyl or O-haloC$_{1-3}$ alkyl;
R$^4$ is independently selected from the group consisting of:
a) C$_{1-14}$alkyl, optionally substituted with: (1) 1-5 halo groups up to perhaloalkyl; (2) 1-2 C$_{1-10}$alkoxy groups, each optionally substituted with 1-5 halo groups up to perhaloalkoxy; (3) 1-2 Aryl groups, each optionally substituted as follows: (i) 1-5 halo groups, (ii) CN or NO$_2$, and (iii) 1-2 C$_{1-10}$alkyl or alkoxy groups, each optionally substituted with: 1-5 halo, up to perhaloalkyl; and b) Aryl, HAR or Hetcy, each optionally substituted as follows: (1) 1-2 C$_{1-10}$alkyl or C$_{2-10}$alkenyl, optionally substituted with 1-5 halo groups, phenyl or CO$_2$R$^a$ groups; (2) 1-2 C$_{1-10}$alkoxy groups, the alkyl portion of which is optionally substituted with 1-5 halo groups; (3) 1-2 Aryl, HAR or Hetcy, OAryl, OHAR or OHetcy groups, each optionally substituted as follows: (a) 1-3 halo groups; (b) 1-2 C$_{1-10}$alkyl or C$_{2-10}$alkenyl, each optionally substituted with 1-3 halo groups; (c) 1-2 C$_{1-10}$alkoxy groups the alkyl portion of which being optionally substituted with 1-3 halo groups, and (d) 1-2 CO$_2$R$^a$, S(O)$_p$R$^d$, CN, NR$^b$R$^c$, NO$_2$ or OH groups;

said Aryl, HAR or Hetcy group b) being further optionally substituted on carbon by a group selected from the group consisting of: (4) 1-5 halo groups; (5) 1-2 OH groups; (6) 1 S(O)$_p$R$^d$, NO$_2$ or CN group; (7) 1-2 CO$_2$R$^a$; (8) —NR$^a$—C (O)—NR$^b$R$^c$; (9) —NR$^a$—CO$_2$R$^c$; (10) —NR$^a$—C(O)R$^c$; (11) —NR$^b$R$^c$; (12) —NR$^a$SO$_2$R$^c$; (13) —SO$_2$—NR$^b$R$^c$; (14) —C(O)NR$^b$R$^c$ and (15) —OC(O)—NR$^b$R$^c$;

and when R$^4$ represents Hetcy containing a nitrogen atom, said nitrogen atom can be optionally substituted with a member selected from the group consisting of: (a) —C(O)NR$^b$R$^c$; (b) —CO$_2$R$^c$; (c) —C(O)R$^c$; and (d) —SO$_2$R$^c$;

R$^8$ and R$^9$ are taken in combination and represent —(CH$_2$)$_{2-4}$—;
R$^5$ represents H or C$_{1-6}$ alkyl;
R$^6$ is selected from the group consisting of H, OH, F or C$_{1-3}$alkyl;
R$^7$ is H or F, or R$^6$ and R$^7$ are taken in combination and represent oxo;
R$^a$ is H or C$_{1-10}$alkyl, optionally substituted with phenyl, OH, OC$_{1-6}$alkyl, CO$_2$H, CO$_2$C$_{1-6}$alkyl and 1-3 halo groups;
R$^b$ is H or C$_{1-10}$alkyl;
R$^c$ is H or is independently selected from: (a) C$_{1-10}$alkyl, optionally substituted with OH, OC$_{1-6}$alkyl, CO$_2$H, CO$_2$C$_{1-6}$ alkyl, and 1-3 halo groups; (b) Aryl or Ar—C$_{1-6}$alkyl, each optionally substituted with 1-5 halos and 1-3 members selected from the group consisting of: CN, OH, C$_{1-10}$alkyl and OC$_{1-10}$ alkyl, said alkyl and alkoxy being further optionally substituted with 1-5 halo groups up to perhalo; (c) Hetcy or Hetcy-C$_{1-6}$alkyl, optionally substituted with 1-5 halo groups and 1-3 groups selected from: oxo, C$_{1-10}$alkyl and OC$_{1-10}$ alkyl, said alkyl and alkoxy being further optionally substituted with 1-5 halo groups up to perhalo; and (d) HAR or HAR-C$_{1-6}$alkyl, optionally substituted with 1-5 halo groups and 1-3 groups selected from: C$_{1-10}$alkyl and OC$_{1-10}$ alkyl, said alkyl and alkoxy being further optionally substituted with 1-5 halo groups up to perhalo;

R$^d$ is C$_{1-10}$alkyl, Aryl or Ar—C$_{1-10}$alkyl;
m is an integer selected from 0, 1 and 2;
n is an integer selected from 0 to 6;
p is an integer selected from 0, 1 and 2, and
when at least one of m and n is other than 0, Z is selected from CO$_2$R$^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl). Within this aspect of the invention, all other variables are as originally defined with respect to formula I Selected compounds of the invention that are of interest are shown in the table below.

TABLE A

Key to Compounds

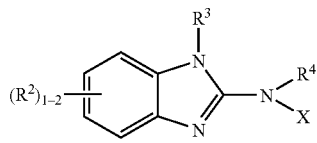

wherein $R^2$, $R^3$ and $R^4$ are in accordance with formula I and X is as shown below.

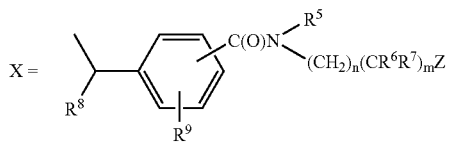

| | | | |
|---|---|---|---|
| R4-1 = | (4-chlorophenoxy)-2-chloro-4-methylphenyl | X-1 = | —CH₂—C₆H₄—C(O)NHCH₂CH₂CO₂H |
| R4-2 = | 4-methyl-t-Bu-cyclohexyl | X-3 = | —CH₂—C₆H₄—C(O)NH-tetrazolyl |
| R4-54 = | 4-cyclohexylphenyl | X-19 = | —CH₂—C₆H₄—C(O)NHCH(OH)CO₂Me |
| R4-95 = | 4-(OCF₃)phenyl | X-21 = | —CH₂—C₆H₄—C(O)NHCH(OH)CO₂H |
| R4-113 = | indanyl | X-29 = | —CH₂—C₆H₄—C(O)NHCH₂-tetrazolyl |
| R4-122 = | 3,5-dichlorophenyl | X-70 = | —CH(Me)—C₆H₄—C(O)NH-tetrazolyl |
| R4-238 = | biphenyl | X-85 = | —CH(CH₃)—C₆H₄—C(O)NH(CH₂)₂CO₂H |
| R4-245 = | diphenylmethyl | X-86 = | —CH(CH₃)—C₆H₄—C(O)NHCH₂CH(OH)CO₂H |

TABLE A-continued

Key to Compounds

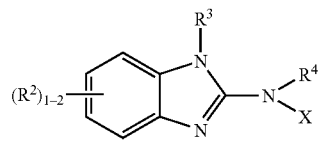

wherein $R^2$, $R^3$ and $R^4$ are in accordance with formula I and X is as shown below.

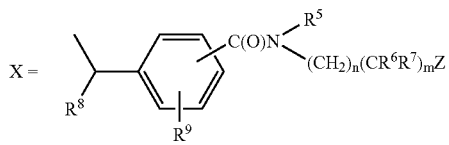

| | | | |
|---|---|---|---|
| R4-256 = | (adamantyl) | X-226 = | —CH₂—C₆H₄—C(O)NHCH₂CO₂H |
| R4-258 = | 3-Cl benzyl (ethyl) | X-227 = | —CH₂—C₆H₄—C(O)NH(CH₂)₃CO₂H |
| R4-260 = | 4-methyl-1-CF₃-cyclohexyl | X-237 = | 1-methylindane-5-C(O)NH-tetrazole |
| R4-261 = | 4-Br benzyl (methyl) | X-238 = | 1-methylindane-5-C(O)NH—CH₂CH₂CO₂H |
| R4-262 = | 4-t-Bu benzyl (methyl) | X-239 = | 1-methylindane-5-C(O)NH—CH₂CH(OH)CO₂H |
| R4-265 = | 4-Cl benzyl (ethyl) | X-244 = | 4-ethyl-3-Br-benzoyl-NH-tetrazole |
| R4-266 = | 2-Cl benzyl (ethyl) | R4-267 = | 4-methylcyclohexyl-phenyl |
| R4-269 = | methyl-tetrahydronaphthyl-F | R4-273 = | 4-methyl-isopropyl-phenyl |

TABLE A-continued
Key to Compounds
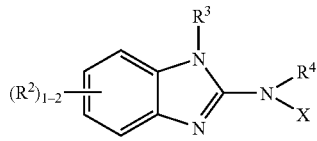
wherein $R^2$, $R^3$ and $R^4$ are in accordance with formula I and X is as shown below.
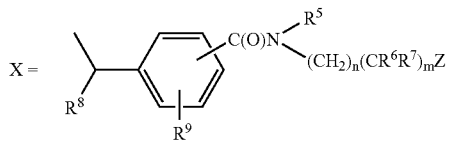
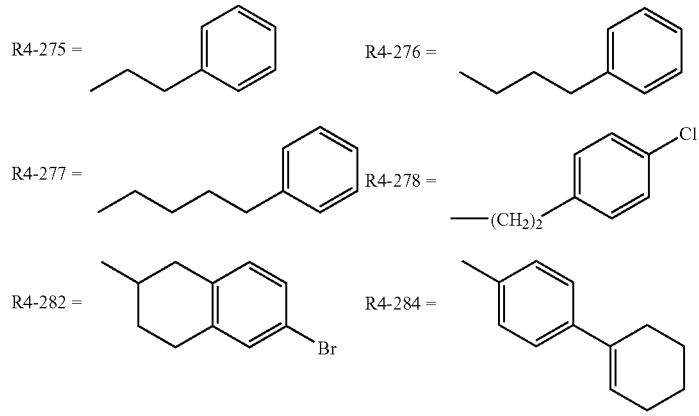
TABLE A
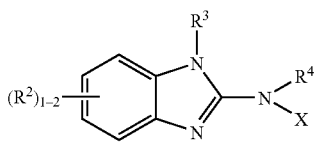
wherein
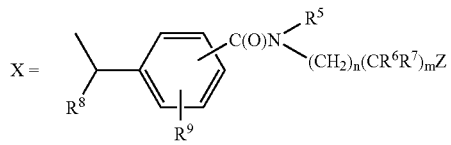
| Cpd No. | $R^2$ | $R^3$ | $R^4$ | X |
|---|---|---|---|---|
| 1 | 5-Me | H | R4-1 | X-1 |
| 2 | 5-Me | H | R4-2 | X-1 |
| 3 | 5-Me | H | R4-1 | X-3 |
| 4 | 5-Me | H | R4-2 | X-3 |
| 5 | 5-OCF$_3$ | H | R4-1 | X-1 |
| 6 | 5-OCF$_3$ | H | R4-2 | X-3 |
| 7 | 5-OCF$_3$ | H | R4-2 | X-1 |
| 8 | 6-Me | Me | R4-2 | X-3 |
| 9 | 5-Cl | H | R4-2 | X-3 |
| 10 | 5-Cl | H | R4-1 | X-3 |
| 11 | 6-Me | Me | R4-2 | X-1 |
| 12 | 5-Cl | H | R4-2 | X-1 |
| 13 | 5-Cl | H | R4-1 | X-1 |
| 14 | 5-Me | Me | R4-1 | X-3 |
| 15 | 5-Me | Me | R4-1 | X-1 |
| 16 | H | H | R4-2 | X-3 |

TABLE A-continued

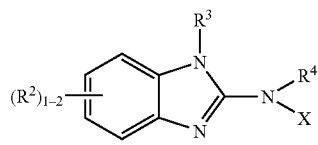

wherein

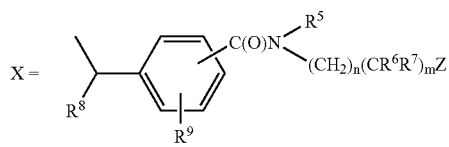

| Cpd No. | $R^2$ | $R^3$ | $R^4$ | X |
|---|---|---|---|---|
| 17 | H | H | R4-2 | X-1 |
| 18 | H | Me | R4-2 | X-1 |
| 19 | H | Me | R4-2 | X-19 |
| 20 | H | Me | R4-2 | X-3 |
| 21 | H | Me | R4-2 | X-21 |
| 22 | 6-Me | Me | R4-2 | X-21 |
| 23 | 5-Me | H | R4-2 | X-21 |
| 24 | H | Et | R4-2 | X-3 |
| 25 | H | Et | R4-2 | X-1 |
| 26 | H | Et | R4-2 | X-21 |
| 27 | H | n-Pr | R4-2 | X-3 |
| 28 | H | n-Pr | R4-2 | X-1 |
| 29 | H | n-Pr | R4-2 | X-29 |
| 30 | H | n-Pr | R4-2 | X-21 |
| 31 | 5-Me | H | R4-2 | X-29 |
| 32 | H | cPentyl | R4-2 | X-3 |
| 33 | H | cPentyl | R4-2 | X-1 |
| 34 | H | cPentyl | R4-2 | X-21 |
| 35 | H | Et | R4-2 | X-29 |
| 36 | H | Benzyl | R4-2 | X-3 |
| 37 | H | Benzyl | R4-2 | X-29 |
| 38 | H | Benzyl | R4-2 | X-1 |
| 39 | H | Benzyl | R4-2 | X-21 |
| 40 | H | —$CH_2CH(Me)_2$ | R4-2 | X-3 |
| 41 | H | —$CH_2CH(Me)_2$ | R4-2 | X-29 |
| 42 | H | —$CH_2CH(Me)_2$ | R4-2 | X-1 |
| 43 | H | —$CH_2CH(Me)_2$ | R4-2 | X-21 |
| 44 | H | H | R4-2 | X-29 |
| 45 | H | H | R4-2 | X-21 |
| 46 | H | Me | R4-2 | X-29 |
| 47 | H | $CH_2CH_2F$ | R4-2 | X-3 |
| 48 | H | $CH_2CH_2F$ | R4-2 | X-1 |
| 49 | H | $CH_2CH_2F$ | R4-2 | X-21 |
| 50 | H | $CH_2CH_2F$ | R4-2 | X-29 |
| 51 | H | $CH_2CH=CH_2$ | R4-2 | X-3 |
| 52 | H | $CH_2CH=CH_2$ | R4-2 | X-1 |
| 53 | H | $CH_2CH=CH_2$ | R4-2 | X-21 |
| 54 | H | H | R4-54 | X-3 |
| 55 | H | H | R4-54 | X-1 |
| 56 | H | H | R4-54 | X-21 |
| 57 | H | Me | R4-54 | X-3 |
| 58 | H | Me | R4-54 | X-1 |
| 59 | H | Me | R4-54 | X-21 |
| 60 | 5,6-di-Cl | H | R4-2 | X-3 |
| 61 | 5,6-di-Cl | H | R4-2 | X-29 |
| 62 | 5,6-di-Cl | H | R4-2 | X-1 |
| 63 | 5,6-di-Cl | H | R4-2 | X-21 |
| 64 | 5,6-di-Cl | Et | R4-2 | X-3 |
| 65 | 5,6-di-Me | H | R4-2 | X-3 |
| 66 | 5,6-di-Me | H | R4-2 | X-29 |
| 67 | 5,6-di-Me | H | R4-2 | X-1 |
| 68 | 5,6-di-Me | H | R4-2 | X-21 |
| 69 | H | Me | R4-2 | X-70 |
| 70 | H | $CH_2CH_2OH$ | R4-2 | X-3 |
| 71 | H | $CH_2CH_2OH$ | R4-2 | X-1 |
| 72 | H | $CH_2CH_2OH$ | R4-2 | X-21 |
| 73 | 5,6-di-Me | Me | R4-2 | X-3 |
| 74 | 5,6-di-Me | Me | R4-2 | X-29 |
| 75 | 5,6-di-Me | Me | R4-2 | X-1 |

TABLE A-continued wherein

X structure: contains C(O)N(R$^5$)(CH$_2$)$_n$(CR$^6$R$^7$)$_m$Z group on a phenyl ring with R$^9$ substituent, connected via CH(R$^8$)CH$_3$ group.

| Cpd No. | R$^2$ | R$^3$ | R$^4$ | X |
|---|---|---|---|---|
| 76 | 5,6-di-Me | Me | R4-2 | X-21 |
| 77 | 5,6-di-Cl | Me | R4-2 | X-3 |
| 78 | 5,6-di-Cl | Me | R4-2 | X-1 |
| 79 | 5,6-di-Cl | Me | R4-2 | X-21 |
| 80 | 5,6-di-F | H | R4-2 | X-3 |
| 81 | 5,6-di-F | H | R4-2 | X-1 |
| 82 | 5,6-di-F | H | R4-2 | X-29 |
| 83 | 5,6-di-F | H | R4-2 | X-21 |
| 84 | H | Me | R4-2 | X-85 |
| 85 | H | Me | R4-2 | X-86 |
| 86 | 5,6-di-F | Me | R4-2 | X-3 |
| 87 | 5,6-di-F | Me | R4-2 | X-1 |
| 88 | 5,6-di-F | Me | R4-2 | X-21 |
| 89 | H | (CH$_2$)$_3$OH | R4-2 | X-3 |
| 90 | H | (CH$_2$)$_3$OH | R4-2 | X-21 |
| 91 | H | Me | R4-95 | X-3 |
| 92 | H | Me | R4-95 | X-21 |
| 93 | H | (CH$_2$)$_2$NMe$_2$ | R4-2 | X-3 |
| 94 | H | —CH$_2$—C$_6$H$_4$—OCF$_3$ | R4-2 | X-3 |
| 95 | H | —CH$_2$—C$_6$H$_4$—OCF$_3$ | R4-2 | X-21 |
| 96 | H | —CH$_2$—C$_6$H$_4$—OCF$_3$ | R4-2 | X-1 |
| 97 | H | Phenyl | R4-2 | X-3 |
| 98 | H | Phenyl | R4-2 | X-29 |
| 99 | H | Phenyl | R4-2 | X-1 |
| 100 | H | Phenyl | R4-2 | X-21 |
| 101 | 6-allyloxy | Et | R4-2 | X-3 |
| 102 | 6-allyloxy | Et | R4-2 | X-1 |
| 103 | 6-allyloxy | Et | R4-2 | X-21 |
| 104 | 6-allyloxy | Et | R4-2 | X-29 |
| 105 | 5,6-di-F | Et | R4-2 | X-3 |
| 106 | H | Me | R4-113 | X-3 |
| 107 | 5,6-di-F | Et | R4-2 | X-21 |
| 108 | 6-OH | Et | R4-2 | X-3 |
| 109 | 6-OH | Et | R4-2 | X-1 |
| 110 | 5,6-di-F | Et | R4-2 | X-1 |
| 111 | 6-OH | Et | R4-2 | X-21 |
| 112 | 6-OH | Et | R4-2 | X-29 |
| 113 | 5-OMe | Me | R4-2 | X-3 |
| 114 | 5-OMe | Me | R4-2 | X-21 |
| 115 | 5-OMe | Me | R4-2 | X-1 |
| 116 | H | H | R4-122 | X-3 |
| 117 | H | H | R4-122 | X-1 |
| 118 | H | H | R4-122 | X-21 |
| 119 | H | H | R4-122 | X-29 |
| 120 | 5-OH | Me | R4-2 | X-3 |
| 121 | 5-OH | Me | R4-2 | X-1 |

TABLE A-continued
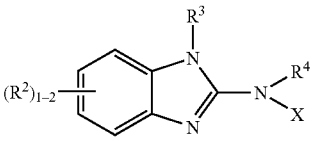
wherein
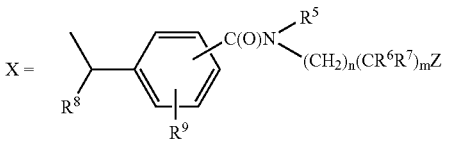
| Cpd No. | R² | R³ | R⁴ | X |
|---|---|---|---|---|
| 122 | 5-OH | Me | R4-2 | X-21 |
| 123 | 5-allyloxy | Me | R4-2 | X-3 |
| 124 | 5-allyloxy | Me | R4-2 | X-1 |
| 125 | 5-benzyloxy | Me | R4-2 | X-3 |
| 126 | 5-benzyloxy | Me | R4-2 | X-1 |
| 127 | 6-allyloxy | Me | R4-2 | X-3 |
| 128 | 6-allyloxy | Me | R4-2 | X-1 |
| 129 | 6-allyloxy | Me | R4-2 | X-21 |
| 130 | 6-allyloxy | Me | R4-2 | X-29 |
| 131 | H |  | R4-2 | X-3 |
| 132 | H | 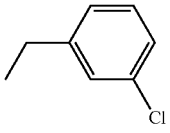 | R4-2 | X-3 |
| 133 | H | 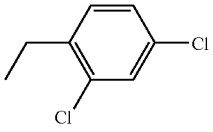 | R4-2 | X-3 |
| 134 | H |  | R4-2 | X-21 |
| 135 | H | 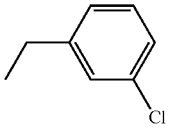 | R4-2 | X-21 |
| 136 | H | 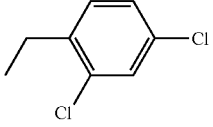 | R4-2 | X-21 |
| 137 | H | 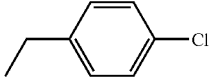 | R4-2 | X-1 |
| 138 | H | 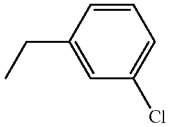 | R4-2 | X-1 |

TABLE A-continued wherein

X = [structure: phenyl with CH(R8)(Me) substituent, R9 substituent, and C(O)N(R5)(CH2)n(CR6R7)mZ group]

| Cpd No. | R² | R³ | R⁴ | X |
|---|---|---|---|---|
| 139 | H | [2,4-dichlorophenyl ethyl] | R4-2 | X-1 |
| 140 | 6-OH | Me | R4-2 | X-3 |
| 141 | 6-OH | Me | R4-2 | X-1 |
| 142 | 6-OH | Me | R4-2 | X-21 |
| 143 | 6-OH | Me | R4-2 | X-29 |
| 144 | 5-n-propyloxy | Me | R4-2 | X-3 |
| 145 | 5-n-propyloxy | Me | R4-2 | X-29 |
| 146 | 5-n-propyloxy | Me | R4-2 | X-1 |
| 147 | 5-n-propyloxy | Me | R4-2 | X-21 |
| 148 | 5-isopropyloxy | Me | R4-2 | X-3 |
| 149 | 5-isopropyloxy | Me | R4-2 | X-29 |
| 150 | 5-isopropyloxy | Me | R4-2 | X-1 |
| 151 | 5-isopropyloxy | Me | R4-2 | X-21 |
| 152 | 6-n-propyloxy | Me | R4-2 | X-3 |
| 153 | 6-n-propyloxy | Me | R4-2 | X-1 |
| 154 | 6-n-propyloxy | Me | R4-2 | X-21 |
| 155 | 5-OMe | Me | R4-2 | X-29 |
| 156 | 5-cyclo-pentyloxy | Me | R4-2 | X-3 |
| 157 | 5-cyclo-pentyloxy | Me | R4-2 | X-29 |
| 158 | 5-OCH₂CH(Me)₂ | Me | R4-2 | X-3 |
| 159 | 5-OCH₂CH(Me)₂ | Me | R4-2 | X-29 |
| 160 | 6-benzyloxy | Me | R4-2 | X-3 |
| 161 | 6-isopropyloxy | Me | R4-2 | X-3 |
| 162 | 6-OMe | Me | R4-2 | X-3 |
| 163 | 6-benzyloxy | Me | R4-2 | X-1 |
| 164 | 6-isopropyloxy | Me | R4-2 | X-1 |
| 165 | 6-OMe | Me | R4-2 | X-1 |
| 166 | 6-benzyloxy | Me | R4-2 | X-21 |
| 167 | 6-isopropyloxy | Me | R4-2 | X-21 |
| 168 | 6-OMe | Me | R4-2 | X-21 |
| 169 | 5-benzyloxy | Me | R4-2 | X-21 |
| 170 | 5-cyclopentyloxy | Me | R4-2 | X-1 |
| 171 | 5-cyclopentyloxy | Me | R4-2 | X-21 |
| 172 | 5-isobutyloxy | Me | R4-2 | X-1 |
| 173 | 5-isobutyloxy | Me | R4-2 | X-21 |
| 174 | 6-allyloxy | Me | R4-113 | X-3 |
| 175 | 6-allyloxy | Me | R4-113 | X-1 |
| 176 | H | [3,4-dichlorophenyl ethyl] | R4-2 | X-3 |
| 177 | 6-allyloxy | Me | R4-113 | X-21 |
| 178 | H | [4-cyanophenyl ethyl] | R4-2 | X-3 |

TABLE A-continued
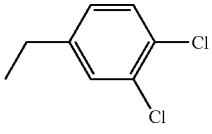
wherein
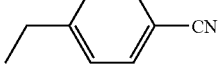
| Cpd No. | R² | R³ | R⁴ | X |
|---|---|---|---|---|
| 179 | H | 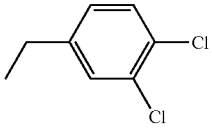 | R4-2 | X-21 |
| 180 | H | 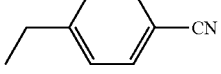 | R4-2 | X-21 |
| 181 | H | 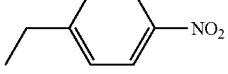 | R4-2 | X-1 |
| 182 | H | 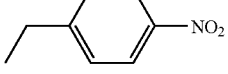 | R4-2 | X-1 |
| 183 | H | 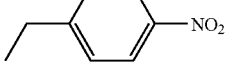 | R4-2 | X-3 |
| 184 | H | 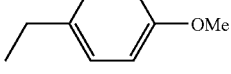 | R4-2 | X-21 |
| 185 | H | 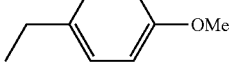 | R4-2 | X-1 |
| 186 | H | 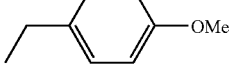 | R4-2 | X-3 |
| 187 | H | | R4-2 | X-21 |
| 188 | H | | R4-2 | X-1 |
| 189 | H | Me | R4-2 | X-237 |
| 190 | H | Me | R4-2 | X-238 |
| 191 | H | Me | R4-2 | X-239 |
| 192 | 6-cyclopentyloxy | Me | R4-2 | X-3 |
| 193 | 6-cyclopentyloxy | Me | R4-2 | X-1 |
| 194 | 6-cyclopentyloxy | Me | R4-2 | X-21 |

TABLE A-continued

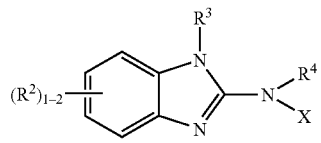

wherein

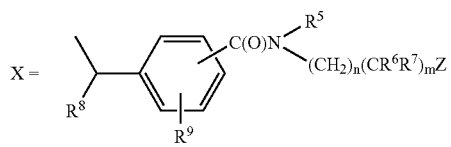

| Cpd No. | R² | R³ | R⁴ | X |
| --- | --- | --- | --- | --- |
| 195 | 5-OMe | Me | R4-54 | X-3 |
| 196 | 5-OMe | Me | R4-54 | X-1 |
| 197 | 6-allyloxy | Me | R4-95 | X-3 |
| 198 | 6-allyloxy | Me | R4-95 | X-1 |
| 199 | 6-allyloxy | Me | R4-95 | X-21 |
| 200 | 6-OH | Me | R4-95 | X-3 |
| 201 | 5-OEt | Me | R4-2 | X-3 |
| 202 | 5-cyclobutyloxy | Me | R4-2 | X-3 |
| 203 | 5-cyclopropyl methoxy | Me | R4-2 | X-3 |
| 204 | 5-cyclopropyl methoxy | Me | R4-2 | X-1 |
| 205 | 5-cyclohexyl methoxy | Me | R4-2 | X-3 |
| 206 | 5-cyclohexyl methoxy | Me | R4-2 | X-1 |
| 207 | 5-OEt | Me | R4-2 | X-1 |
| 208 | 5-cyclobutyloxy | Me | R4-2 | X-1 |
| 209 | 5-OCH₂CHF₂ | Me | R4-2 | X-3 |
| 210 | 5-OCH₂CHF₂ | Me | R4-2 | X-1 |
| 211 | 5-cyclobutyl methoxy | Me | R4-2 | X-3 |
| 212 | 5-cyclobutyl methoxy | Me | R4-2 | X-1 |
| 213 | 5-cyclopentyl methoxy | Me | R4-2 | X-3 |
| 214 | 5-cyclopentyl methoxy | Me | R4-2 | X-1 |
| 215 | 6-n-propyloxy | Me | R4-95 | X-3 |
| 216 | 5-CF₃ | Me | R4-2 | X-3 |
| 217 | 6-benzyloxy | Me | R4-95 | X-3 |
| 218 | 5-CF₃ | Me | R4-2 | X-1 |
| 219 | 5-n-propyloxy | Me | R4-54 | X-3 |
| 220 | 6-n-propyloxy | Me | R4-95 | X-1 |
| 221 | 6-benzyloxy | Me | R4-95 | X-1 |
| 222 | 6-OEt | Me | R4-2 | X-3 |
| 223 | 6-cyclopropyl methoxy | Me | R4-2 | X-3 |
| 224 | 6-OCH₂CH(Me)₂ | Me | R4-2 | X-3 |
| 225 | 6-OEt | Me | R4-2 | X-1 |
| 226 | 6-cyclopropyl methoxy | Me | R4-2 | X-1 |
| 227 | 6-OCH₂CH(Me)₂ | Me | R4-2 | X-1 |
| 228 | H | Me | R4-54 | X-237 |
| 229 | 5-Br | Me | R4-2 | X-3 |
| 230 | 5-Br | Me | R4-2 | X-1 |
| 231 | H | Et | R4-2 | X-226 |
| 232 | H | Et | R4-2 | X-227 |
| 233 | 6-OCH₂CHF₂ | Me | R4-2 | X-3 |
| 234 | 6-OCH₂CHF₂ | Me | R4-2 | XI |
| 235 | 5-OMe | Me | R4-2 | X-244 |
| 236 | H | Me | R4-245 | X-3 |
| 237 | 6-cyclohexyloxy | Me | R4-2 | X-3 |
| 238 | H | Me | R4-122 | X-3 |
| 249 | 5-n-propyloxy | Me | R4-2 | X-237 |
| 240 | 5-cyclopentyloxy | Me | R4-54 | X-3 |
| 241 | 5-cyclopentyloxy | Me | R4-54 | X-1 |

TABLE A-continued

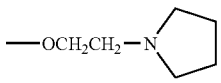

wherein

| Cpd No. | R² | R³ | R⁴ | X |
|---|---|---|---|---|
| 242 | 5-n-propyloxy | Me | R4-54 | X-1 |
| 243 | 6-cyclohexyl methoxy | Me | R4-2 | X-3 |
| 244 | 6-cyclohexyloxy | Me | R4-2 | X-1 |
| 245 | 6-cyclohexyl methoxy | Me | R4-2 | X-1 |
| 246 | H | Me | R4-256 | X-1 |
| 247 | 6- —OCH₂CH₂—N(pyrrolidine) | Me | R4-2 | X-3 |
| 248 | 5-OMe | Me | R4-258 | X-3 |
| 249 | 5-cyclopentyloxy | Me | R4-2 | X-244 |
| 250 | H | Me | R4-260 | X-3 |
| 251 | H | Me | R4-261 | X-3 |
| 252 | H | Me | R4-262 | X-3 |
| 253 | H | Me | R4-262 | X-1 |
| 254 | 5-OMe | Me | R4-122 | X-3 |
| 255 | 5-OMe | Me | R4-265 | X-3 |
| 256 | 5-OMe | Me | R4-266 | X-3 |
| 257 | H | Me | R4-267 | X-1 |
| 258 | H | Me | R4-267 | X-3 |
| 259 | H | Me | R4-269 | X-1 |
| 260 | H | Me | R4-269 | X-3 |
| 261 | H | Me | R4-238 | X-3 |
| 262 | H | Me | R4-238 | X-1 |
| 263 | H | Me | R4-273 | X-3 |
| 264 | H | Me | R4-273 | X-1 |
| 265 | H | Me | R4-275 | X-3 |
| 266 | H | Me | R4-276 | X-3 |
| 267 | H | Me | R4-277 | X-3 |
| 268 | H | Me | R4-278 | X-3 |
| 269 | H | Me | R4-278 | X-1 |
| 270 | 5-n-pentyloxy | Me | R4-122 | X-3 |
| 271 | 5-n-propyloxy | Me | R4-122 | X-3 |
| 272 | H | Me | R4-282 | X-1 |
| 273 | H | Me | R4-282 | X-3 |
| 274 | H | Me | R4-284 | X-3 |
| 275 | H | Me | R4-284 | X-1 |
| 276 | 5-OCF₃ | Me | R4-95 | X-3 |
| 277 | 5-CF₃ | Me | R4-95 | X-3 |
| 278 | 5-Cl | Me | R4-95 | X-3 |
| 279 | 5-OMe | Me | R4-95 | X-3 |
| 278 | 5-OMe | Me | R4-95 | X-1 |
| 281 | 5-n-propyloxy | Me | R4-95 | X-3 |
| 282 | 5-cyclopentyloxy | Me | R4-95 | X-3 | as the pharmaceutically acceptable salts and solvates thereof.

The invention further includes a pharmaceutical composition which is comprised of a compound of formula I in combination with a pharmaceutically acceptable carrier.

Also included is a method of treating type 2 diabetes mellitus in a mammalian patient in need of such treatment, comprising administering to said patient a compound of formula I in an amount that is effective to treat type 2 diabetes mellitus.

Also included is a method of preventing or delaying the onset of type 2 diabetes mellitus in a mammalian patient in need thereof, comprising administering to said patient a compound of formula I in an amount that is effective to prevent or delay the onset of type 2 diabetes mellitus.

Also included is a method of treating hyperglycemia, diabetes or insulin resistance in a mammalian patient in need of such treatment which comprises administering to said patient an effective amount of a compound of formula I.

Also included is a method of treating, preventing or delaying the onset of diseases or conditions that are associated with type 2 diabetes mellitus. Examples include diseases and conditions selected from the group consisting of: dyslipidemias, (e.g., hyperlipidemia), such as elevated levels of cholesterol (hypercholesterolemia), triglycerides (hypertriglyceridemia) or low density lipoproteins (LDL) (high LDL levels), low levels of high density lipoprotein (HDL), microvascular or macrovascular changes and the sequellae of such conditions, such as coronary heart disease, stroke, peripheral vascular disease, hypertension, renal hypertension, nephropathy, neuropathy and retinopathy. The method entails administering to a type 2 diabetic patient, e.g., a human patient, an amount of a compound of formula I that is effective for treating, preventing or delaying the onset of such diseases or conditions.

Also included is a method of treating atherosclerosis in a mammalian patient in need of such treatment, comprising administering to said patient a compound of formula I in an amount effective to treat atherosclerosis.

Also included is a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient a compound in accordance with formula I in an amount that is effective to treat said condition.

Also included is a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need thereof, comprising administering to the patient a compound of formula I in an amount that is effective to delay the onset of said condition.

Also included is a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component in a mammalian patient in need of such treatment, comprising administering to the patient a compound of formula I in an amount that is effective to reduce the risk of developing said condition.

Optical Isomers-Diastereomers-Geometric Isomers-Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Salts and Solvates

The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I include the pharmaceutically acceptable salts and solvates.

This invention relates to method of antagonizing or inhibiting the production or activity of glucagon, thereby reducing the rate of gluconeogenesis and glycogenolysis, and the concentration of glucose in plasma.

The compounds of formula I can be used in the manufacture of a medicament for the prophylactic or therapeutic treatment of disease states in mammals caused by elevated levels of glucose, comprised of combining the compound of formula I with the carrier materials to provide the medicament.

Dose Ranges

The prophylactic or therapeutic dose of the compound of formula I will, of course, vary with the nature of the condition to be treated, the particular compound selected and its route of administration. It will also vary according to the age, weight and response of the individual patient. In general, the daily dose range lie within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases. The terms "effective amount" "anti-diabetic effective amount" and the other terms appearing throughout the application addressing the amount of the compound to be used refer to the dosage ranges provided, taking into account any necessary variation outside of these ranges, as determined by the skilled physician.

Representative dosages for adults range from about 0.1 mg to about 1.0 g per day, preferably about 1 mg to about 200 mg, in single or divided doses.

When intravenous or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of Formula I per kg of body weight per day.

Pharmaceutical Compositions

As mentioned above, the pharmaceutical composition comprises a compound of Formula I or a pharmaceutically acceptable salt or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred. Thus, one aspect of the invention that is of interest is the use of a compound of formula I for preparing a pharmaceutical composition which is comprised of combining the compound of formula I with the carrier.

In preparing oral compositions, any of the usual pharmaceutical media may be employed, such as, for example, water, glycols, oils, alcohols, flavoring agents, preservatives, coloring agents and the like in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets, with the solid oral preparations being preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 1 g of the active ingredient and each cachet or capsule contains from about 1 to about 500 mg of the active ingredient.

The following are examples of pharmaceutical dosage forms for the compounds of

| Formula I: | |
| --- | --- |
| Injectable Suspension (I.M.) | mg/mL |
| Compound of Formula I | 10.0 |
| Methylcellulose | 5.0 |
| Tween 80 | 0.5 |
| Benzyl alcohol | 9.0 |
| Benzalkonium chloride | 1.0 |
| Water for injection to make | 1.0  mL |
| Capsule | mg/capsule |
| Compound of Formula I | 25.0 |
| Lactose Powder | 573.5 |
| Magnesium Stearate | 1.5 |
| Total | 600  mg |
| Tablet | mg/tablet |
| Compound of Formula I | 25 |
| Microcrystalline Cellulose | 415 |
| Povidone | 14.0 |
| Pregelatinized Starch | 43.5 |
| Magnesium Stearate | 2.5 |
| Total | 500  mg |
| Aerosol | Per canister |
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/delaying the onset of type 2 diabetes mellitus, as well as the diseases and conditions associated with type 2 diabetes mellitus, for which compounds of Formula I are useful. Other drugs may be administered, by a route and in an amount commonly used therefor, contemporaneously or sequentially with a compound of Formula I. When a compound of Formula I is used with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Examples of other active ingredients that may be combined with a compound of Formula I, either administered separately or in the same pharmaceutical compositions, include, but are not limited to: (a) bis-guanides (e.g., buformin, metformin, phenformin), (b) PPAR agonists (e.g., troglitazone, pioglitazone, rosiglitazone), (c) insulin, (d) somatostatin, (e) □-glucosidase inhibitors (e.g., voglibose, miglitol, acarbose), (f) DP-IV inhibitors, (g) LXR modulators and (h) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide and repaglinide).

The weight ratio of the compound of the Formula I to the second active ingredient may be varied within wide limits and depends upon the effective dose of each ingredient. Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

For combination products, the compound of formula I may be combined with any other active ingredients and then added to the carrier ingredients; alternatively the order of mixing may be varied.

Examples of pharmaceutical combination compositions include: 1) a compound according to formula I, 2) a compound selected from the group consisting of: a) DP-IV inhibitors; b) insulin sensitizers selected from the group consisting of (i) PPAR agonists and (ii) biguanides; c) insulin and insulin mimetics; d) sulfonylureas and other insulin secretagogues; e) alpha glucosidase inhibitors; f) glucagon receptor antagonists; g) GLP-1, GLP-1 mimetics, and GLP-1 receptor agonists; h) GIP, GIP mimetics, and GIP receptor agonists; i) PACAP, PACAP mimetics, and PACAP receptor 3 agonists; j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents other than glucocorticoids; and (o) protein tyrosine phosphatase-1B (PTP-1B) inhibitors; and 3) a pharmaceutically acceptable carrier.

A method that is of particular interest relates to a method of treating, preventing or delaying the onset of diabetes, and in particular, type 2 diabetes, in a mammalian patient in need thereof, comprising administering to the patient 1) a compound according to formula I, and 2) a compound selected from the group consisting of: a) DP-IV inhibitors; b) insulin sensitizers selected from the group consisting of (i) PPAR agonists and (ii) biguanides; c) insulin and insulin mimetics; d) sulfonylureas and other insulin secretagogues; e) alpha glucosidase inhibitors; f) glucagon receptor antagonists; g) GLP-1, GLP-1 mimetics, and GLP-1 receptor agonists; h) GIP, GIP mimetics, and GIP receptor agonists; i) PACAP, PACAP mimetics, and PACAP receptor 3 agonists; j) cholesterol lowering agents selected from the group consisting of (i) HMG-CoA reductase inhibitors, (ii) sequestrants, (iii) nicotinyl alcohol, nicotinic acid or a salt thereof, (iv) PPAR alpha agonists, (v) PPAR alpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents other than glucocorticoids; and (o) protein tyrosine phosphatase-1B (PTP-1B) inhibitors; said compounds being administered in an amount that is effective to treat, prevent or delay the onset of type 2 diabetes.

In accordance with the methods described herein one method that is of interest relates to a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other conditions and disorders where insulin resistance is a component, in a mammalian patient in need of such treatment, comprising administering to the patient an effective amount of a compound of formula I and a compound selected from the group consisting of: (a) DP-IV inhibitors; (b) insulin sensitizers selected from the group consisting of (i) PPAR agonists and (ii) biguanides; (c) insulin and insulin mimetics; (d) sulfonylureas and other insulin secretagogues; (e) alpha glucosidase inhibitors; (f) glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of: (i) HMG-CoA reductase inhibitors, (ii) sequestrants, (iii) nicotinyl alcohol, nicotinic acid and salts thereof, (iv) PPAR alpha agonists, (v) PPARalpha/gamma dual agonists, (vi) inhibitors of cholesterol absorption, (vii) acyl CoA:cholesterol acyltransferase inhibitors, (viii) anti-oxidants and (ix) LXR modulators; (k) PPAR delta agonists; (l) antiobesity compounds; (m) an ileal bile acid transporter inhibitor; (n) anti-inflammatory agents excluding glucocorticoids; and (o) protein tyrosine phosphatase-1B (PTP-1B) inhibitors, said compounds being administered to the patient in an amount that is effective to treat said condition.

More particularly, a method that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a therapeutically effective amount of a compound of formula I and an HMG-CoA reductase inhibitor.

Even more particularly, the method that is of interest comprises administering to the patient a therapeutically effective amount of a compound of formula I and an HMG-CoA reductase inhibitor wherein the HMG-CoA reductase inhibitor is a statin, and even more particularly, the statin is selected from the group consisting of lovastatin, simvastatin, pravastatin, fluvastatin, atorvastatin, itavastatin, ZD4522 and rivastatin.

A different aspect of the invention relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound of formula I and an HMG-CoA reductase inhibitor.

Another aspect of the invention relates to a method for delaying the onset or reducing the risk of developing atherosclerosis in a human patient in need of such treatment comprising administering to said patient an effective amount of a compound of formula I and an HMG-CoA reductase inhibitor. More particularly, the method comprises administering an effective amount of a compound of formula I and an HMG-CoA reductase inhibitor wherein the HMG-CoA reductase inhibitor is a statin. Even more particularly, the method comprises administering a compound of formula I and a statin selected from the group consisting of: lovastatin, simvastatin, pravastatin, fluvastatin, atorvastatin, itavastatin, ZD4522 and rivastatin. Still more particularly, the method comprises administering a compound of formula I and the statin known as simvastatin.

Another aspect of the invention relates to a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound of formula I and a cholesterol absorption inhibitor. In particular, the method comprises administering an effective amount of a compound of formula I and the cholesterol absorption inhibitor known as ezetimibe.

More particularly, a method for delaying the onset or reducing the risk of developing atherosclerosis in a human patient in need of such treatment is described which comprises administering to said patient an effective amount of a compound of formula I and a cholesterol absorption inhibitor. More particularly, the method comprises administering a compound of formula I and the cholesterol absorption inhibitor known as ezetimibe.

Throughout the instant application, the following abbreviations are used with the following meanings unless otherwise indicated:

| | |
|---|---|
| Bu = butyl, t-Bu = t-butyl | Bn and Bnzl = benzyl |
| BOC, Boc = t-butyloxycarbonyl | CBZ, Cbz = Benzyloxycarbonyl |
| DCC = Dicyclohexylcarbodiimide | DCM = dichloromethane |
| DIEA = diisopropylethylamine | DMF = N,N-dimethylformamide |
| DIAD = diisopropylazodicarboxylate | Et = ethyl |
| DMAP = 4-Dimethylaminopyridine | EtOH = ethanol |
| EtOAc = ethyl acetate | FAB-mass spectrum = Fast atom bombardment-mass spectroscopy |
| eq. = equivalent(s) | HPLC = High pressure liquid chromatography |
| HOAc = acetic acid | LAH = Lithium aluminum hydride |
| HOBT, HOBt = Hydroxybenztriazole | PBS = phosphate buffer saline |
| Me = methyl | TFA = Trifluoroacetic acid |
| Ph = phenyl | TMS = Trimethylsilane |
| THF = Tetrahydrofuran | $Nme_2$ = dimethylamino |
| $C_6H_{11}$ = cyclohexyl | 2ClPh = 2-chlorophenyl |
| iPr, $^iPr$ = isopropyl | Py, Pyr = pyridyl |
| 2,4-diClPh = 2,4-dichlorophenyl | |

Compounds of the present invention may be prepared according to the methodology outlined in the following general synthetic schemes.

In one embodiment of the present invention, the compounds (Ia) where $R^3$ is hydrogen may be prepared from ester IIa (vide infra),

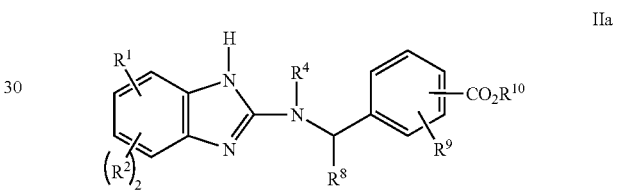

IIa where $R^1$, $R^2$, $R^4$, $R^8$, and $R^9$ are as defined above and $R^{10}$ represents an alkyl or aryl group.

Compounds IIa are known in the literature or may be conveniently prepared by a variety of methods familiar to those skilled in the art as described in "Comprehensive Organic Chemistry", Katritzky et. al., Vol 5. One such route is illustrated in Scheme 1. Amine 1 may be commercially available or readily prepared via a reductive amination sequence by treating, for example, carbomethoxy benzaldehyde 2 (if $R^8$ and $R^9$ are hydrogen) and an amine 3 with a reducing agent such as sodium triacetoxyborohydride or cyanoborohydride in a solvent such as dichloroethane at ambient temperature. Alternatively, the benzylamine 4 can be reacted with the appropriate $R^4$ carbonyl containing substituent under the same conditions to give amine 1. Amine 1 is then treated with thiophosgene in the presence of a base such as diethylisopropylamine (DIEA) in a nonpolar aprotic solvent such as dichloromethane at temperatures of zero to 25° C. followed by direct addition of a 1,2-diaminobenzene and either mercury (II) trifluoroacetate or methyl iodide (for example *J. Med. Chem.*, 1985, 28, 1925 and *Synthesis*, 1974, 41). The reaction is stirred a further 30 min to 6 h before isolation of benzimidazole 5 with an aqueous work-up. 1,2-Diaminobenzene analogs are commercially available, or readily prepared by those skilled in the art by reduction of the corresponding 2-nitroaniline with, for example hydrogen and a palladium catalyst or stannous chloride. Either reaction is effected in an alcoholic solvent such as methanol or ethanol.

SCHEME 1

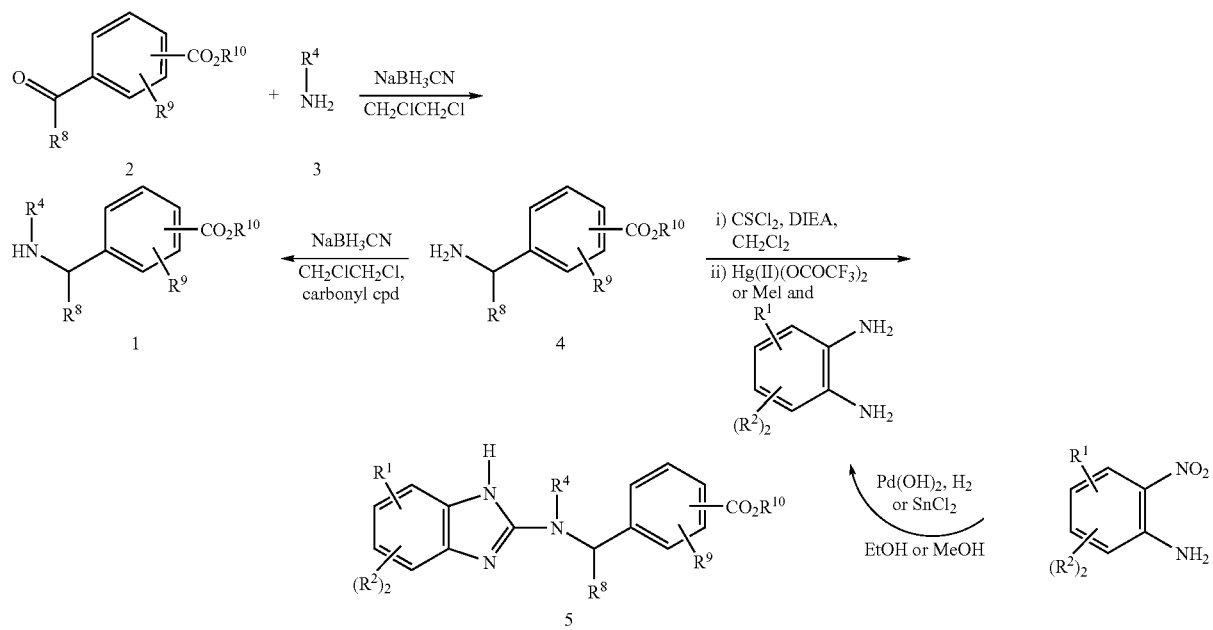

An alternative approach to synthesizing benzimidazole IIa involves reaction of amine 1 with triphosgene in the presence of a base, such as triethylamine, in a nonpolar aprotic solvent such as dichloromethane at temperatures of zero to 25° C., as shown in Scheme 2. The carbamoyl chloride 6 formed in the reaction can be readily isolated and treated with a 1,2-diaminobenzene to give the urea which is treated directly with a dehydrating agent, usually phosphorus oxychloride, at elevated temperatures for 6-24 h, followed by an aqueous work-up to yield the benzimidazole 5.

SCHEME 2

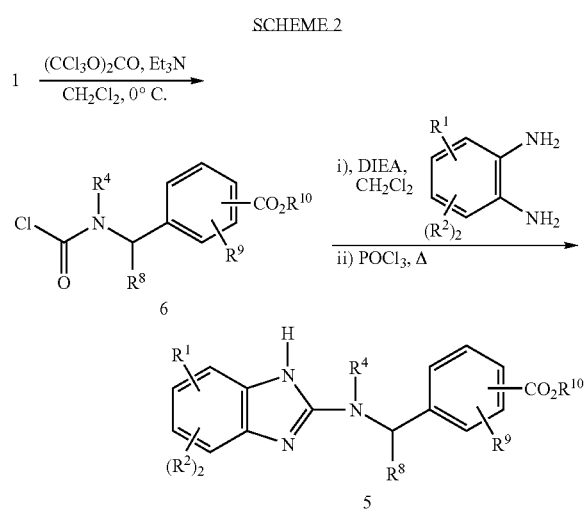

Preparation of the desired compounds 1a (which are defined as compounds of formula I wherein $R^3$ represents H) is then achieved by saponification of the ester 5 using a base such as aqueous lithium or sodium hydroxide in a polar solvent such as tetrahydrofuran, methanol, ethanol or a mixture of similar solvents, Scheme 3. Coupling of the acid with an amine, generally 5-aminotetrazole 7 or a beta alanine derivative 8 which may be substituted at the 2-position, is then achieved using 1-ethyl-3-(3-dimethylaminopropyl)-carbodiimide (EDC), 1-hydroxybenzotriazole (HOBt), and a base, generally diisopropylethylamine, in a solvent such as N,N-dimethylformamide (DMF) or methylene chloride for 3 to 48 hours at ambient temperature to yield the compounds Ia-7 and Ia-8. Other peptide coupling conditions may also be used. The product is purified from unwanted side products by recrystallization, trituration, preparative thin layer chromatography, flash chromatography on silica gel as described by W. C. Still et al, *J. Org. Chem.*, 43, 2923, (1978), or HPLC. Compounds purified by HPLC may be isolated as the corresponding salt. Purification of intermediates is achieved in the same manner. As will be understood by those skilled in the art, for the preparation of enantiomerically pure compounds, enantiomerically pure starting materials should be used.

In some cases further modification of intermediates such as 5 can be undertaken in one of several different ways. These manipulations may include, but are not limited to substitution, reduction, oxidation, alkylation, acylation, and hydrolysis reactions, which are commonly known to those skilled in the art.

SCHEME 3

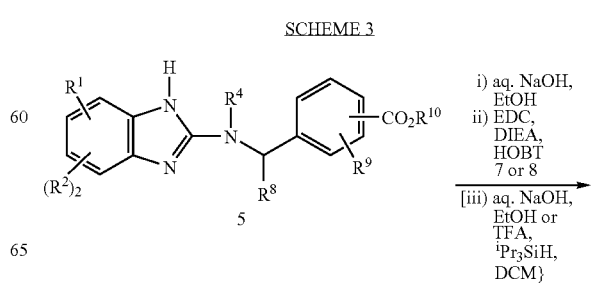

-continued

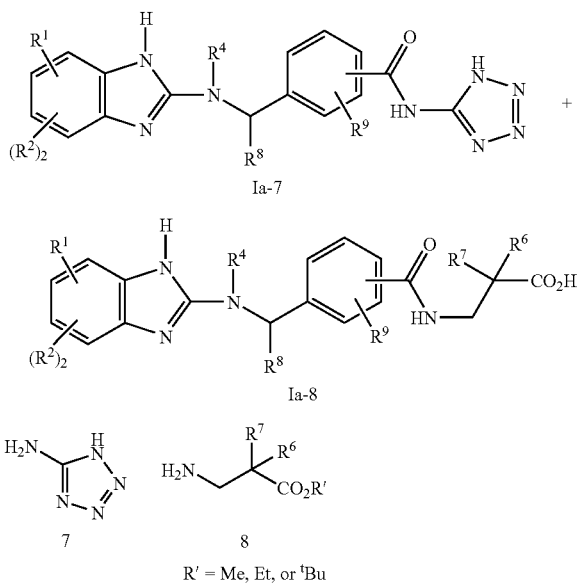

In another embodiment of the present invention, the compounds (Ib) (which are defined as compounds of formula I wherein $R^3$ is not hydrogen) may be prepared from ester IIb (vide infra),

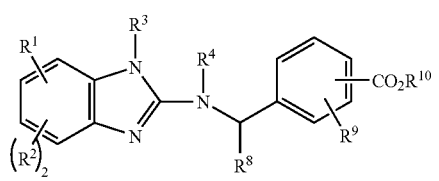

where $R^1$, $R^2$, $R^3$, $R^4$, $R^8$, and $R^9$ are as defined above and $R^{10}$ represents an alkyl or aryl group.

Compounds IIb may be conveniently prepared by a variety of methods known to those skilled in the art. One such example, shown in Scheme 4, involves alkylation of intermediate 5 by deprotonation with a base such as sodium hydride in a polar aprotic solvent such as dimethylformamide (DMF) at 0-25° C. for 15 min to 2 h, followed by addition of an electrophile such as an alkyl iodide. The reaction is stirred, with heating if necessary, for an additional 1-24 h to give intermediate 9.

SCHEME 4

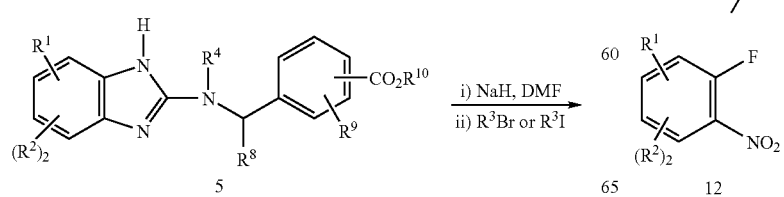

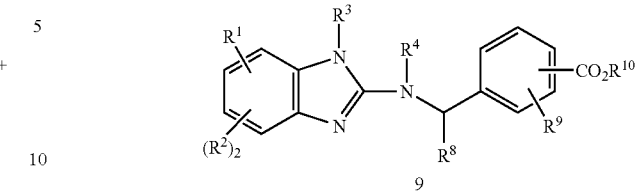

An alternative route goes via the N-alkylated 1,2-diaminobenzene 10. These are commercially available or readily prepared by those skilled in art. One such method involves alkylation of a 2-nitro aniline. This is effected by deprotonation with a base such as sodium hydride in a polar aprotic solvent such as dimethylformamide (DMF) at 0-25° C. for 15 min to 2 h, followed by addition of an electrophile such as an alkyl iodide, Scheme 5. The reaction is stirred for an additional 1-24 h to give intermediate 11, which can be reduced with, for example hydrogen and a palladium catalyst or stannous chloride in an alcoholic solvent. The alkylated 2-nitro aniline 11 can also be prepared by nucleophilic displacement of fluorine from a 2-fluoronitrobenzene 12 with an amine as described in *J. Org. Chem.*, 1999, 64, 3060. This is achieved in a solvent such as methylene chloride or DMF with a base such as DIEA, at temperatures of 25-80° C. for 1-6 h, Scheme 5. The diaminobenzene 10 can then be converted to the benzimidazole 9 using amine 1 or carbamoyl chloride 6 in an identical fashion to that described above and illustrated in Schemes 6 and 7.

SCHEME 5

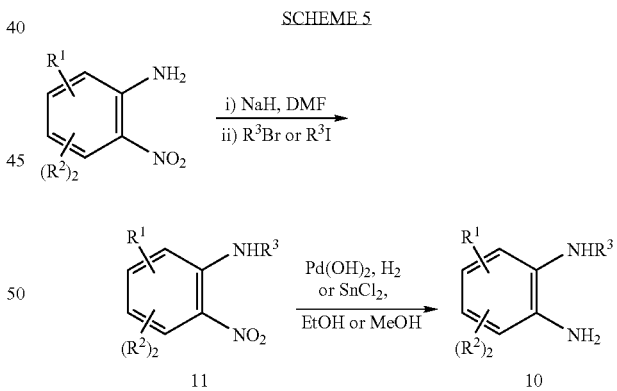

SCHEME 6

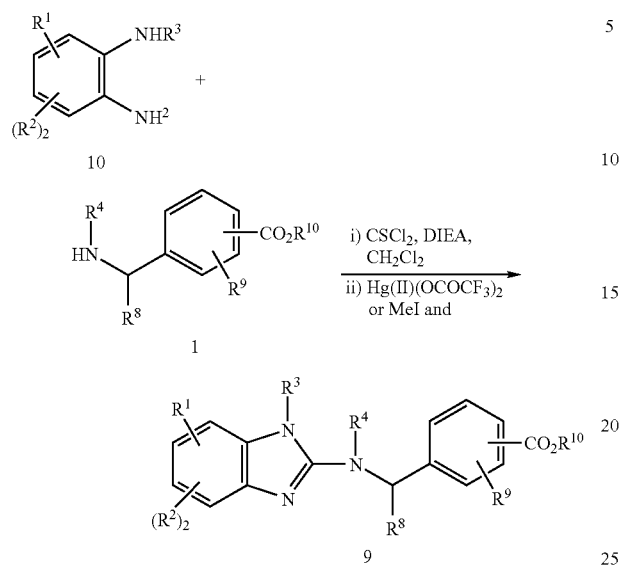

Scheme 7

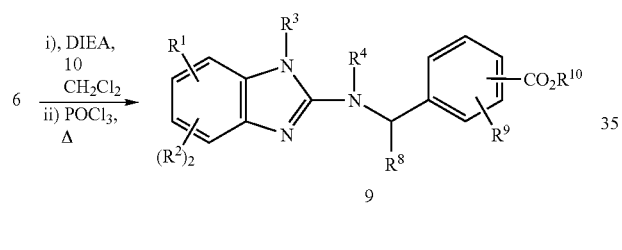

A third route to intermediates IIb involves alkylation of the 2-aminobenzimdazole 13 with a benzylic bromide, for example carbomethoxybenzyl-bromide, as illustrated in Scheme 8. Amine 3 is converted to the isothiocyanate by reaction with thiophosgene in the presence of a base such as DIEA in a nonpolar aprotic solvent such as dichloromethane at temperatures of zero to 25° C. followed by addition of diamine 10 and cyclization with an agent such as methyl iodide. This reaction is effected at 25-50° C. for 1-24 h to give amine 13. Deprotonation is achieved with a base such as sodium hydride or potassium carbonate in a nonpolar aprotic solvent such as DMF to give a mixture of the desired compound 9 and its isomer 14. These are generally separable by recrystallization, trituration, preparative thin layer chromatography, flash chromatography on silica gel or HPLC.

SCHEME 8

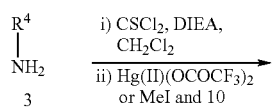

Conversion of ester 9 to the final products is achieved by saponification of the ester using a base such as aqueous lithium or sodium hydroxide in a polar solvent such as tetrahydrofuran, methanol, ethanol or a mixture of similar solvents, Scheme 9. Coupling of the acid with an amine, generally 5-aminotetrazole 7 or a beta alanine derivative 8 which may be substituted at the 2-position, is then achieved using 1-ethyl-3-(3-dimethylaminopropyl)-carbodiimide (EDC), 1-hydroxybenzotriazole (HOBt), and a base, generally diisopropylethylamine, in a solvent such as N,N-dimethylformamide (DMF) or methylene chloride for 3 to 48 hours at ambient temperature to yield the compounds Ib-7 and Ib-8. Other standard peptide coupling conditions may also be used. The product is purified from unwanted side products by recrystallization, trituration, preparative thin layer chromatography, flash chromatography on silica gel as described by W. C. Still et al, *J. Org. Chem.*, 43, 2923, (1978), or HPLC. Compounds purified by HPLC may be isolated as the corresponding salt. Purification of intermediates is achieved in the same manner.

SCHEME 9

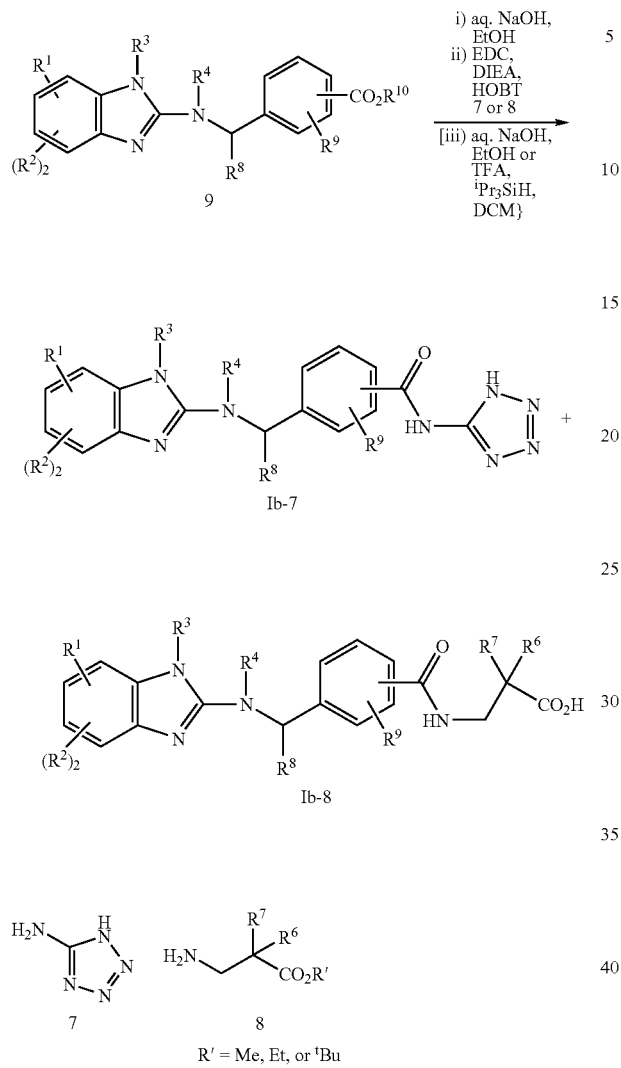

SCHEME 10

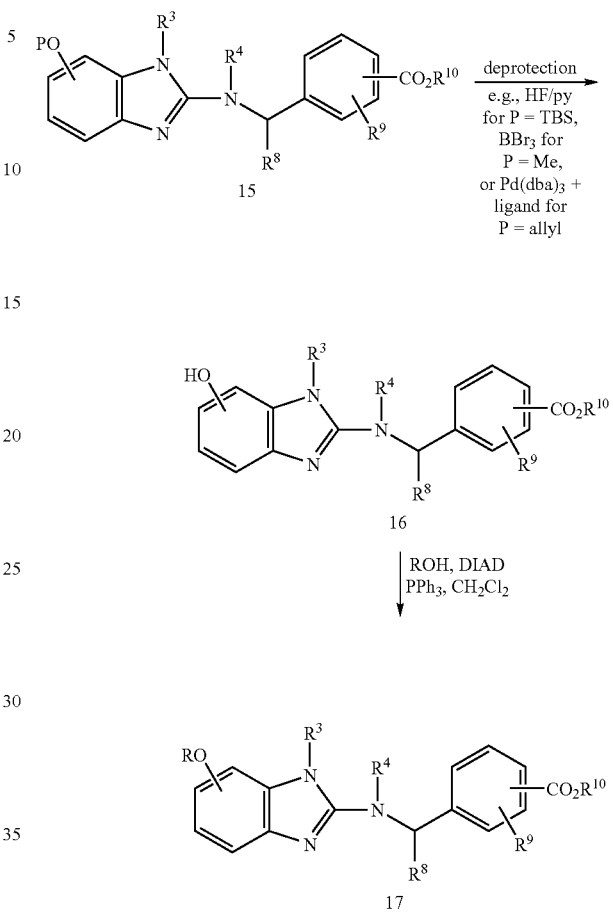

In some cases further modification of intermediates such as 9 can be undertaken in one of several different ways. These manipulations may include, but are not limited to substitution, reduction, oxidation, alkylation, acylation, and hydrolysis reactions, which are commonly known to those skilled in the art. One such modification, illustrated here when $R^1$ or $R^2$ is a protected alcohol as in 15, involves release of the alcohol and subsequent etherification. The hydroxyl group may be protected as a silyl ether, in which case a fluoride source, generally hydrofluoric acid or tetrabutylammonium fluoride is used for the reaction. Deprotection of a methoxy ether is routinely effected by treatment of the compound with boron tribromide in a solvent such as methylene chloride for a period of 1-16 h at ambient temperatures. Finally, if the alcohol is protected as an allyl ether, this is removed by treatment with dimethylbarbituric acid and a palladium catalyst, routinely tris(dibenzylideneacetone)dipalladium(0), with a ligand such as 1,4-bis-(diphenylphospino)butane in an aprotic solvent such as methylene chloride for 15 min to 2 h. See "Protective Groups in Organic Synthesis", Greene, published by Wiley and Sons.

The free hydroxyl group may then be further modified to prepare ethers using an alcohol and coupling agent, such as diisopropylazodicarboxylate, and triphenylphosphine in a non polar solvent such as methylene chloride at temperatures of 0 to 40° C. for 1 to 16 h, Scheme 10. Intermediates 16 and 17 can then be converted to the desired products as previously described, vide supra.

Another such modification, illustrated here when $R^4$ contains an aromatic halide as in 18, Scheme 11, involves coupling reactions either with a boronic acid in a Suzuki type coupling or a vinyl stannane to give products such as 19 and 20. For the former reaction, the halide is coupled with a boronic acid, exemplified here with phenyl boronic acid, using a palladium catalyst such as palladium acetate and tris-o-tolylphosphine or triphenyl phosphine. The solvent is generally DMF or ethanol, and cesium carbonate or aqueous sodium carbonate is also added to the reaction, which is performed at elevated temperatures for 12-24 h (see *Helv. Chim. Acta,* 1992, 75, 855). Preparation of intermediates 20 is carried out by reaction with a vinyl stannane in the presence of a palladium catalyst such as palladium tris-o-tolylphosphine. The solvent is generally DMF, and the reaction is performed at elevated temperatures for 1-8 h. Intermediates 19 and 20 can then be converted to the desired products as previously described, vide supra.

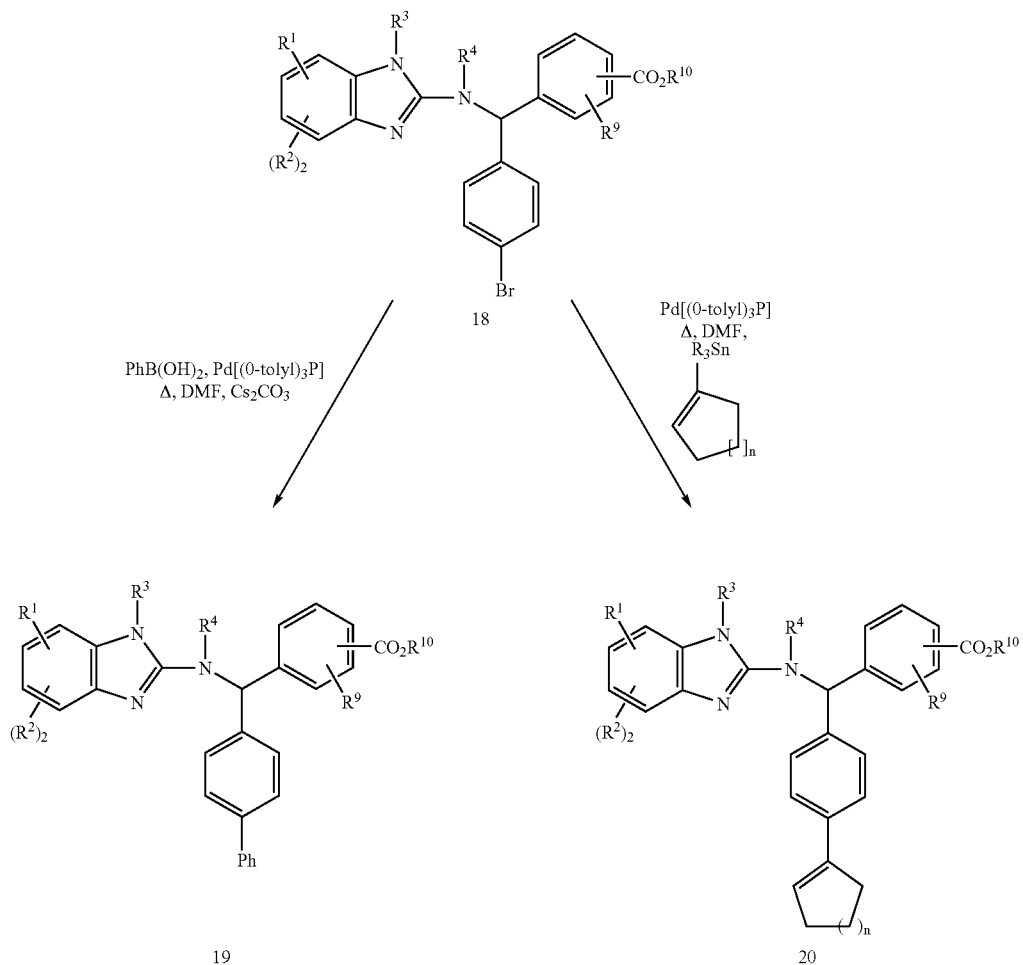

In cases where $R^8$ and $R^9$ form a 5-membered ring alternate conditions were used for the synthesis of the amine intermediate 21, Scheme 12. For example, commercially available ketone 22 was converted to amine 23 by a reductive amination sequence using a Lewis acid such as titanium isopropoxide in ethanol at ambient temperature for 6-24 h, followed by further reduction with a hydride reducing agent such as sodium borohydride (J. C. S., Perkin Trans 1, 1998, 2527-2531). Alternatively, decaborane in methanol at ambient temperature can be used for the reductive amination (J.C.S. Perkin Trans 1, 2000 145-146). The requisite ester linkage is then installed by treatment of the bromide with a base such as butyl lithium at −78° C. in a polar aprotic solvent such as THF, followed by quenching the reaction with solid carbon dioxide to give the acid. Esterification, with TMS diazomethane for example, gives amine 21. Intermediate 21 can then be converted to the desired products as previously described, vide supra.

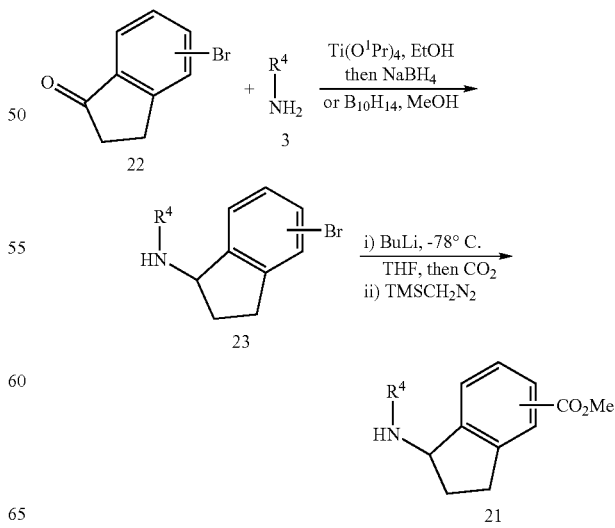

The following examples are provided so that the invention might be more fully understood. They should not be construed as limiting the invention in any way.

General experimental: Analytical HPLC analysis for examples 1-274 (HPLC A) was performed on a YMC Combiscreen ODS-A column (50×4.6 mm i.d.) at a flow rate of 4 mL/min using a gradient elution of 10-100% acetonitrile in water containing 0.1% trifluoroacetic acid. Preparative HPLC was performed on a YMC-Pack Pro C18 column (150× 20 mm i.d.) at an initial flow rate of 4 mL/min for 1.35 min, followed by 20 mL/min for 10.6 min. Various concentration gradients were used during the faster part of the run (see below), and all runs were followed with 100% organic for 0.5 min.

Condition A: 10 to 90% acetonitrile in water (each containing 0.1% trifluoroacetic acid).

Condition B: 20 to 60% acetonitrile in water (each containing 0.1% trifluoroacetic acid).

Condition C: 20 to 80% acetonitrile in water (each containing 0.1% trifluoroacetic acid).

Condition D: 20 to 100% acetonitrile in water (each containing 0.1% trifluoroacetic acid).

EXAMPLE 1

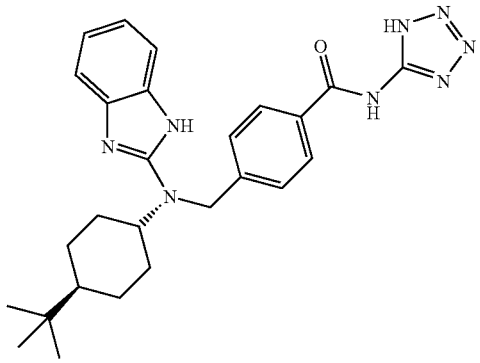

Step A. 1-Isothiocyanato-2-nitrobenzene

To a solution of 2-nitroaniline (10 mmol, 1.38 g) and DIEA (15 mmol, 2.6 mL) in 10 mL of DCM at 0° C. was added thiophosgene (15 mmol, 1.14 mL). The reaction was brought to 65° for 45 min. Purification by flash chromatography on silica eluting with 10% EtOAc/hexanes afforded the isothiocyanate as a gold solid. HPLC A: 2.24 min.

Step B. Methyl 4-{[(4-tert-butylcyclohexyl)amino]methyl}benzoate

To a solution of methyl-4-formylbenzoate (73 mmol, 12 g) in 200 mL of MeOH was added 4-tert-butylcyclohexylamine (74 mmol, 13.2 mL) via syringe. The reaction mixture was heated to reflux for 0.75 h, then was cooled in an ice bath. The resulting precipitate was filtered and the filter cake was washed with 2×20 mL of cold MeOH. The solid was dried under reduced pressure, then suspended in 224 mL of MeOH. HOAc (652 mmol, 37.4 mL) was added to the solution, followed by NaBH$_3$CN (42.7 mmol, 2.68 g) in several portions. The reaction mixture was stirred at ambient temperature for 1.5 h, then concentrated under reduced pressure to ca. 25% of the initial volume. 400 mL of EtOAc was added to the solution and the mixture was washed with 3×200 mL of 5% NaHCO$_3$ followed by brine. The organic phase was dried over MgSO$_4$ and concentrated under reduced pressure. The residue was purified by flash chromatography on silica eluting with 1:1 EtOAc/hexanes to afford the trans isomer as a white solid. $^1$H NMR (500 MHz, CDCl$_3$): δ 8.00 (d, 2H), 7.40 (d, 2H), 3.92 (s, 3H), 3.88 (s, 2H), 2.40 (m, 1H), 2.01 (m, 2H), 1.79 (m, 2H), 0.95-1.15 (overlapping m, 5H), 0.85 (s, 9H).

Step C. Methyl 4-{[1H-benzimidazol-2-yl(4-tert-butylcyclohexyl)amino]methyl}-benzoate To the title compound of Example 1 Step B (2.13 mmol, 721 mg) in 2.5 mL of DMF was added DIEA (0.8 mL), followed by the title compound of Example 1 Step A (2.5 mmol, 450 mg). The reaction mixture was concentrated under reduced pressure. The residue was taken up in 5 mL of DMF containing 0.4 mL of H$_2$O, and SnCl$_2$ (2 g) was added (exothermic). The crude thiourea was concentrated under reduced pressure and the residue was taken up in 10 mL of EtOH. MeI (400 μL) was added and the resulting mixture was heated at 60° for 1 h and concentrated under reduced pressure. The product was purified by flash chromatography on silica eluting with 30% EtOAc/hexanes affording a slightly pink solid. $^1$H NMR (500 MHz, CD$_3$OD): δ 8.00 (d, 2H), 7.43 (d, 2H), 7.29 (m, 2H), 7.14 (m, 2H), 4.86 (s, 2H), 4.04 (m, 1H), 3.89 (s, 3H), 1.82-1.95 (overlapping m, 4H), 1.57 (m, 2H), 1.29 (m, 2H), 1.05 (m, 1H), 0.89 (s, 9H). MS (ESI): m/z 420 (M+H). HPLC A: 2.30 min.

Step D. 4-{[1H-Benzimidazol-2-yl(4-tert-butylcyclohexyl)amino]methyl}benzoic acid To the title compound of Example 1 Step C (0.21 mmol, 90 mg) in 2 mL of dioxane was added a solution of LiOH (2.1 mmol, 52 mg) in 0.6 mL of H$_2$O. The reaction was stirred at 40° C. for 3 h. The product was partitioned into EtOAc/H$_2$O acidified with 2 N HCl. The aqueous phase was washed with EtOAc and the combined organic phase was dried with MgSO$_4$ and concentrated under reduced pressure affording a yellow solid. HPLC A: 1.98 min.

Step E. 4-{[1H-Benzimidazol-2-yl(4-tert-butylcyclohexyl)amino]methyl}-N-(1H-tetra-azol-5-yl)benzamide To a solution of the title compound of Example 1 Step D (0.1 mmol, 41 mg), 1H-tetraazol-5-amine monohydrate (0.2 mmol, 21 mg), HOBt (0.25 mmol, 38 mg) and EDC (0.4 mmol, 77 mg) in 1 mL of DMF was added DIEA (0.5 mmol, 90 μL). The reaction mixture was allowed to stand at ambient temperature overnight, then concentrated under reduced pressure. The residue was taken up in ca. 2:1 dioxane/H$_2$O, acidified with TFA, and purified by reverse-phase chromatography (Condition A). Lyophilization afforded the product as a white solid. MS (ESI): m/z 473 (M+H). HPLC A: 1.86 min.

EXAMPLE 2

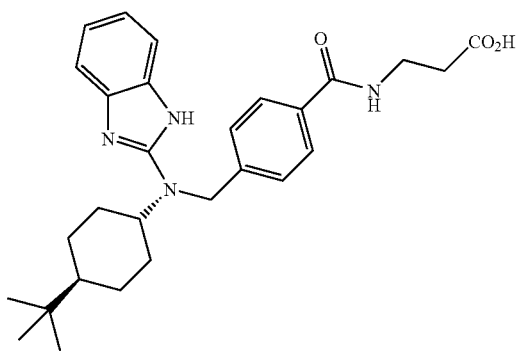

N-(4-{[1H-Benzimidazol-2-yl(4-tert-butylcyclo-hexyl)amino]methyl}benzoyl)-β-alanine To a solution of the title compound of Example 1 Step D (0.1 mmol, 41 mg), the hydrochloride salt of β-alanine tert-butyl ester (0.15 mmol, 27 mg), HOBt (0.25 mmol, 38 mg) and EDC (0.4 mmol, 77 mg) in 1 mL of DMF was added DIEA (0.5 mmol, 90 µL). The reaction mixture was allowed to stand at ambient temperature overnight, then partitioned into EtOAc/H$_2$O. The aqueous phase was washed with EtOAc, and the combined organic phase was dried with MgSO$_4$ and the solvent was removed under reduced pressure. The residue was treated with 3 mL of 2:30:68H$_2$O/TFA/DCM for 1 hr and the solution was concentrated under reduced pressure. Purification by reverse-phase chromatography (Condition A), followed by lyophilization, afforded the product as a white solid. MS (ESI): m/z 477 (M+H). HPLC A: 1.70 min.

EXAMPLE 3

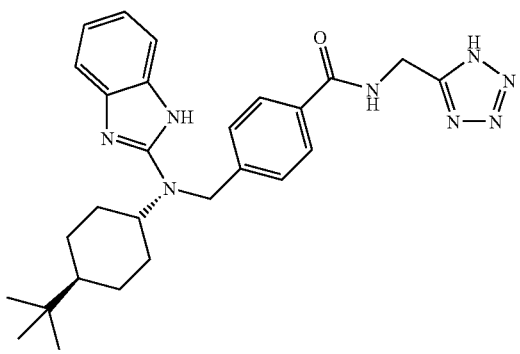

4-{[1H-Benzimidazol-2-yl(4-tert-butylcyclohexyl) amino]methyl}-N-(1H-tetraazol-5-ylmethyl)benza-mide To a solution of the title compound of Example 1 Step D (0.04 mmol, 16 mg), 1H-tetraazol-5-ylmethylamine (0.06 mmol, 8 mg), HOBt (0.1 mmol, 15 mg) and EDC (0.12 mmol, 23 mg) in 0.4 mL of DMF was added DIEA (0.2 mmol, 35 µL). After 3 h the reaction mixture was concentrated under reduced pressure. The product was purified by reverse-phase chromatography (Condition A) and lyophilized, affording the title compound as a white solid. MS (ESI): m/z 487 (M+H). HPLC A: 1.58 min.

EXAMPLE 4

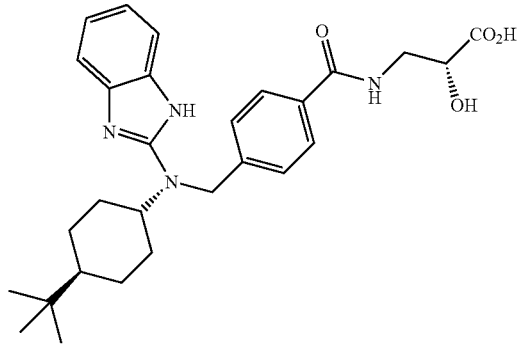

(2R)-3-[(4-{[1H-Benzimidazol-2-yl(4-tert-butylcy-clohexyl)amino]methyl}benzoyl)-amino]-2-hydrox-ypropanoic acid To a solution of the title compound of Example 1 Step D (0.04 mmol, 16 mg), the hydrochloride salt of 2-hydroxy β-alanine methyl ester (0.06 mmol, 9 mg), HOBt (0.1 mmol, 15 mg), and EDC (0.12 mmol, 23 mg) in 0.4 mL of DMF was added DIEA (0.2 mmol, 35 µL). After 3 h the reaction was partitioned into EtOAc/brine. The organic phase was dried with MgSO$_4$ and concentrated under reduced pressure. The residue was taken up in 1 mL of dioxane and a solution of LiOH (1 mmol, 24 mg) in 0.5 mL of H$_2$O was added. The reaction was stirred at ambient temperature overnight, acidified with TFA and the product was purified by reverse-phase chromatography (Condition A) and lyophilized, affording the title compound as a white solid. MS (ESI): m/z 493 (M+H). HPLC A: 1.73 min.

EXAMPLE 5

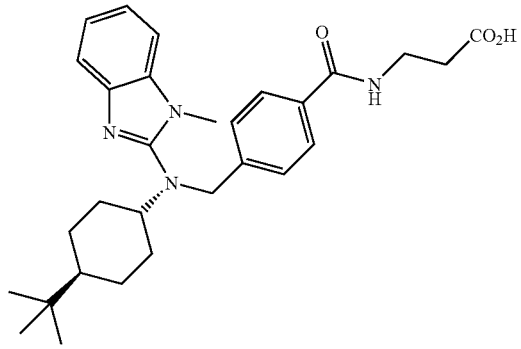

Step A. 4-{[(4-tert-Butylcyclohexyl)(1-methyl-1H-benzimidazol-2-yl)amino]methyl}-benzoic acid To the title compound from Example 1 Step C (0.72 mmol, 300 mg) in 5 mL of THF was added MeI (1 mmol, 67 µL), followed by NaH (1 mmol, 40 mg of 60% dispersion in mineral oil) (exothermic, $H_2$ evolution). After 1 h starting benzimidazole was still present, so the reaction was treated with additional MeI (1 mmol) and NaH (1 mmol). After 1 h the reaction was complete (HPLC A: 2.38). The mixture was concentrated under reduced pressure and the residue was taken up in 6 mL of dioxane. A solution of LiOH (7 mmol, 172 mg) in 2 mL of $H_2O$ was added and the resulting mixture was stirred at ambient temperature overnight. The mixture was poured into EtOAc/$H_2O$, and acidified with 2 N HCl until two clear layers formed after agitation. The organic layer was collected and the aqueous layer was washed with EtOAc. The combined organic phase was dried with $MgSO_4$ and concentrated under reduced pressure affording product as a yellow solid. MS (ESI): m/z 420 (M+H). HPLC A: 2.09 min.

Step B. N-(4-{[(4-tert-Butylcyclohexyl)(1-methyl-1H-benzimidazol-2-yl)amino]methyl}-benzoyl)-□-alanine To a solution of the title compound of Example 5 Step A (0.06 mmol, 24 mg), the hydrochloride salt of β-alanine tert-butyl ester (0.09 mmol, 16 mg), HOBt (0.15 mmol, 23 mg) and EDC (0.18 mmol, 35 mg) in 0.8 mL of DCM was added DIEA (0.3 mmol, 52 µL). The reaction mixture was allowed to stand at ambient temperature for 3 h, then partitioned into EtOAc/brine. The aqueous phase was washed with EtOAc, and the combined organic phase was dried with $MgSO_4$ and the solvent was removed under reduced pressure. The residue was treated with 3 mL of 2:30:68 $H_2O$/TFA/DCM for 1 hr and the solution was concentrated under reduced pressure. The crude product was purified by reverse-phase chromatography (Condition A), then lyophilized, affording the title compound as a white solid. MS (ESI): m/z 491 (M+H). HPLC A: 1.92 min.

EXAMPLE 6

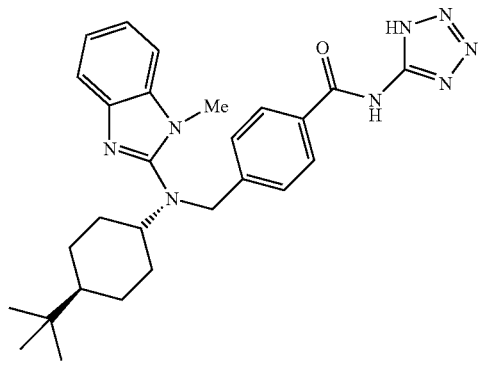

4-{[(4-tert-Butylcyclohexyl)(1-methyl-1H-benzimidazol-2-yl)amino]methyl}-N(1H-tetraazol-5-yl)benzamide To a solution of the product of Example 5 Step A (0.14 mmol, 64 mg), 1H-tetraazol-5-amine monohydrate (0.28 mmol, 29 mg), HOBt (0.35 mmol, 53 mg) and EDC (0.56 mmol, 108 mg) in 1 mL of DMF was added DIEA (0.7 mmol, 122 µL). The reaction was allowed to stand at ambient temperature for 21 h, then concentrated under reduced pressure. The residue was taken up in ca. 2:1 dioxane/$H_2O$ and acidified with TFA, then purified by reverse-phase chromatography (Condition A). The product was lyophilized, affording a white solid. $^1$H NMR (500 MHz, $CD_3OD$): δ 8.01 (d, 2H), 7.52-7.62 (overlapping m, 3H), 7.35-7.50 (overlapping m, 3H), 3.87 (s, 3H), 3.76 (m, 1H), 2.16 (m, 2H), 1.99 (m, 2H), 1.84 (m, 2H), 1.30 (m, 2H), 1.14 (m, 1H), 0.92 (s, 9H). MS (ESI): m/z 487 (M+H). HPLC A: 1.97 min.

EXAMPLE 7

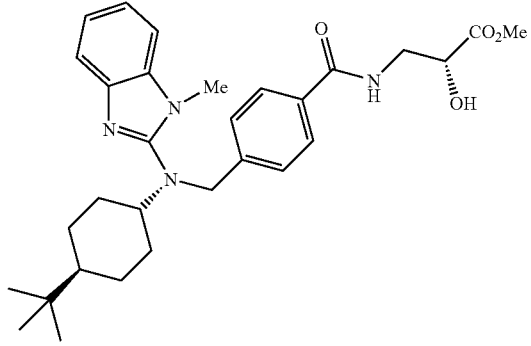

Methyl (2R)-3-[(4-{[(4-tert-butylcyclohexyl)(1-methyl-1H-benzimidazol-2-yl)amino]-methyl}benzoyl)amino]-2-hydroxypropanoate To a solution of the title compound of Example 5 Step A (0.32 mmol, 145 mg), the hydrochloride salt of 2-hydroxy β-alanine methyl ester (0.48 mmol, 74 mg), HOBt (0.8 mmol, 121 mg) and EDC (0.96 mmol, 183 mg) in 2 mL of DMF was added DIEA (1.6 mmol, 0.28 mL). After 3 h the reaction was partitioned into EtOAc/brine. The organic phase was dried with $MgSO_4$ and concentrated under reduced pressure. The product was purified by flash chromatography on silica eluting with 1:25:74 MeOH/EtOAc/DCM, affording the title compound as a foamy solid. $^1$HNMR (500 MHz, DMSO-$d_6$): δ 8.47 (t, 1H), 7.75 (d, 2H), 7.60 (m, 1H), 7.48 (m, 1H), 7.45 (d, 2H), 7.30-7.37 (overlapping m, 2H), 4.80 (s, 2H), 3.76 (s, 3H), 3.70 (m, 1H), 3.60 (s, 3H), 3.50 (m, 1H), 3.39 (m, 1H), 2.02 (m, 2H), 1.82 (m, 2H), 1.71 (m, 2H), 1.18 (m, 2H), 1.03 (m, 1H), 0.85 (s, 9H). MS (ESI): m/z 521 (M+H). HPLC A: 1.94 min.

EXAMPLE 8

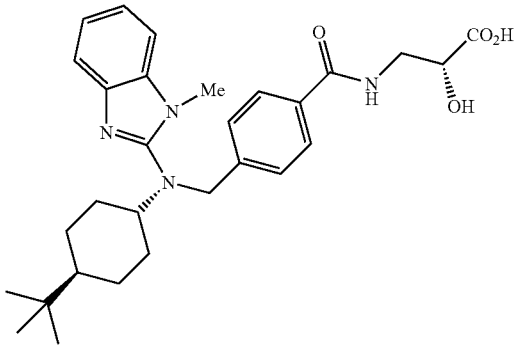

(2R)-3-[(4-{[(4-tert-Butylcyclohexyl)(1-methyl-1H-benzimidazol-2-yl)amino]methyl}-benzoyl)amino]-2-hydroxypropanoic acid To a solution of the title compound of Example 7 (0.1 mmol, 50 mg) in 2 mL of MeOH was added LiOH (0.5 mmol, 12 mg). H₂O was added dropwise until the reaction became slightly cloudy, then the mixture was sonicated to dissolve the LiOH. The reaction was stirred at 40° C. for 2 h. The reaction was concentrated under reduced pressure and the residue was taken up in dioxane/H₂O and acidified with TFA. Purification by reverse-phase HPLC (Condition A), followed by lyophilization, afforded the title compound as a white solid. ¹H NMR (500 MHz, CD3OD): δ 7.79 (d, 2H), 7.58 (m, 1H), 7.39-7.52 (overlapping m, 5H), 4.86 (s, 2H), 4.34 (m, 1H), 3.87 (s, 3H), 3.52-3.84 (overlapping m, 3H), 2.16 (m, 2H), 1.99 (m, 2H), 1.84 (m, 2H), 1.31 (m, 2H), 1.14 (m, 1H), 0.92 (s, 9H). MS (ESI): m/z 487 (M+H). MS (ESI): m/z 507 (M+H). HPLC A: 1.84 min.

EXAMPLE 9

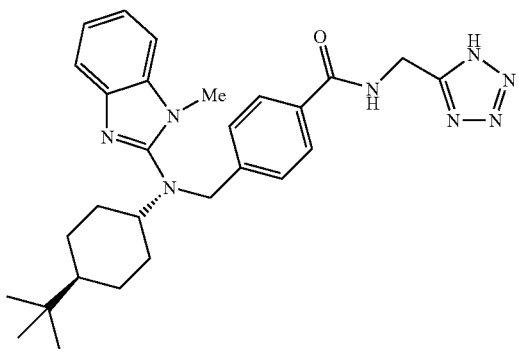

4-{[(4-tert-Butylcyclohexyl)(1-methyl-1H-benzimidazol-2-yl)amino]methyl}-N-(1H-tetraazol-5-ylmethyl)benzamide To a solution of the title compound of Example 5 Step A (0.06 mmol, 25 mg) 1H-tetraazol-5-ylmethylamine (0.09 mmol, 12 mg), HOBt (0.15 mmol, 23 mg) and EDC (0.18 mmol, 35 mg) in 0.5 mL of DMF was added DIEA (0.3 mmol, 52 µL). The reaction was allowed to proceed overnight at ambient temperature. The mixture was partitioned between EtOAc/brine. The organic phase was concentrated under reduced pressure and the residue was purified by reverse-phase chromatography (Condition A) and lyophilized, affording the title compound as a white solid. MS (ESI): m/z 517 (M+H). HPLC A: 1.94 min.

EXAMPLE 10

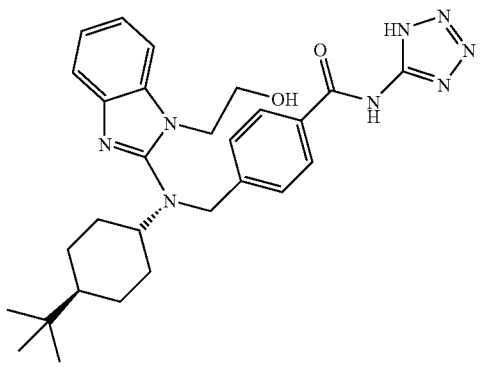

Step A. Methyl 4-{[(4-tert-butylcyclohexyl)(1-{2-[(trimethylsilyl)oxy]ethyl}-1H-benz-imidazol-2-yl)amino]methyl}benzoate To the title compound from Example 1 Step C (0.5 mmol, 210 mg) in 1 mL of THF was added a solution of NaH (1 mmol, 40 mg of 60% slurry in mineral oil) in 1 mL of DMF (exothermic, H₂ evolution). After gas evolution ceased for several minutes, (2-bromoethoxy)(trimethyl)silane was added to the solution via syringe. The reaction mixture was heated to 40° C. After 2.5 h the reaction was quenched by addition of saturated ammonium chloride. The product was extracted 3× with EtOAc and the organic phase was dried over MgSO₄ and concentrated under reduced pressure. The crude product was purified by flash chromatography on silica eluting with 5% EtOAc/hexanes. HPLC A: 3.14 min.

Step B. 4-{[(4-tert-Butylcyclohexyl)(1-{2-hydroxyethyl}-1H-benzimidazol-2-yl)-amino]methyl}benzoic acid To the title compound of Example 10 Step A (0.13 mmol, 73 mg) in 2 mL of dioxane was added a solution of LiOH (1.25 mmol, 30 mg) in 1 mL of H₂O. The resulting solution was stirred at 40° C. overnight. The reaction mixture was taken up in a pH 7 buffer solution and EtOAc. The mixture was acidified with 2 N HCl until two clear layers formed after agitation. The organic layer was collected and the aqueous layer was washed with EtOAc. The combined organic layers were dried with MgSO₄ and concentrated under reduced pressure to afford the acid as a beige solid. MS (ESI): m/z 450 (M+H). HPLC A: 2.05 min.

Step C. 4-({(4-tert-Butylcyclohexyl)[1-(2-hydroxyethyl)-1H-benzimidazol-2-yl]amino}-methyl)-N-(1H-tetraazol-5-yl)benzamide To a solution of the title compound of Example 10 Step B (0.04 mmol, 19 mg) 1H-tetraazol-5-amine monohydrate (0.13 mmol, 13 mg), HOBt (0.085 mmol, 13 mg) and EDC (0.17 mmol, 33 mg) in 0.5 mL of DMF was added DIEA (0.21 mmol, 36 µL). The reaction mixture was allowed to stand at ambient temperature overnight, then concentrated under reduced pressure. The residue was taken up in ca. 2:1 dioxane/H₂O and acidified with TFA, then purified by reverse-phase chromatography (Condition B). The product was lyophilized, affording the title compound as a white solid. MS (ESI): m/z 517 (M+H). HPLC A: 1.81 min.

EXAMPLE 11

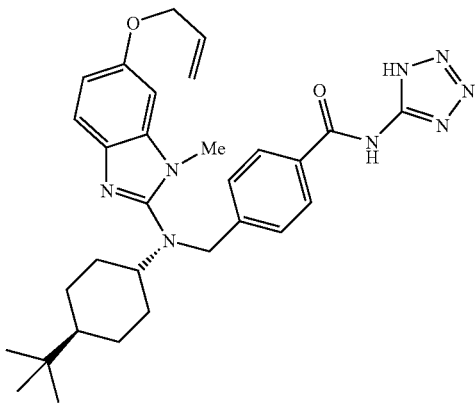

Step A. 4-Allyloxy-2-fluoro-nitrobenzene

To a solution of 3-fluoro-4-nitrophenol (17.5 mmol, 2.75 g) and allyl bromide (17.5 mmol, 1.5 mL) in 10 mL of DMF was added $K_2CO_3$ (21 mmol, 2.9 g). The slurry was stirred at ambient temperature overnight, and partitioned into $NaHCO_3$ (aq)/DCM. The organic phase was removed under reduced pressure affording the product as a brown oil. HPLC A: 2.19 min.

Step B. 5-(Allyloxy)-N-methyl-2-nitroaniline

The title compound of Example 11 Step A (15.2 mmol, 3.01 g) was stirred in 15 mL of 2 M methylamine in THF at 0° C. After the reaction was complete, the reaction mixture was concentrated under reduced pressure and the residue was partitioned into DCM/brine. The organic phase was concentrated under reduced pressure affording the product as a bright yellow solid. $^1H$ NMR (500 MHz, $d_6$-DMSO): δ 8.03 (d, 1H), 6.30-6.36 (overlapping m, 2H), 6.06 (m, 1H), 5.44 (m, 1H), 5.31 (m, 1H), 2.96 (d, 3H). MS (ESI): m/z 209 (M+H). HPLC A: 2.20 min.

Step C. 5-(Allyloxy)-N-methyl-2-aminoaniline

To a solution of the title compound in Example 11 Step B (7.2 mmol, 1.50 g) in 14.6 mL of 10:1 DMF/$H_2O$ was added $SnCl_2$ (anhydrous) (5 mmol, 8.1 g). The reaction mixture was heated at 45° C. overnight. DCM, followed by $NaHCO_3$ (aq) was added slowly to the reaction. The resulting precipitate was removed by filtration over celite. The filter cake was washed with DCM, and the combined organic phase was dried with $MgSO_4$ and concentrated under reduced pressure. The residue was purified by flash chromatography on silica eluting with 20% EtOAc/hexanes, then 30% EtOAc/hexanes, affording the desired product as a brown oil. MS (ESI): m/z 179 (M+H). HPLC A: 0.89 min.

Step D. Methyl 4-{[[6-(allyloxy)-1-methyl-1H-benzimidazol-2-yl](4-tert-butylcyclohexyl)amino]methyl}benzoate To the product of Example 1 Step A (3 mmol, 910 mg) and DIEA (3.6 mmol, 626 µL) in 12 mL of DCM was added thiophosgene (3 mmol, 229 µL). After 1 h additional DIEA (3.6 mmol) and the title compound of Example 11 Step C (2.75 mmol, 489 mg) were added. After 1.5 h $Hg(O_2CCF_3)_2$ (3 mmol, 1.27 g) was added (exothermic), and the slurry was allowed to stand overnight. HPLC analysis revealed the cyclization was incomplete, so additional $Hg(O_2CCF_3)_2$ (1.5 mmol, 650 mg) was added to the reaction. After 2 h the solution was poured into $NaHCO_3$ (aq) containing $Na_2S$, and the slurry was filtered through celite, and the filter cake was washed with DCM. The organic phase was collected and the aqueous phase was extracted with 2×DCM. The combined organic phase was dried with $MgSO_4$ and concentrated under reduced pressure. The residue was purified by flash chromatography on silica eluting with 20% EtOAc/hexanes, then 30% EtOAc/hexanes affording the product as a foamy solid. $^1H$ NMR (500 MHz, $d_6$-DMSO): δ 7.82 (d, 2H), 7.44 (d, 2H), 7.23 (d, 1H), 6.94 (d, 1H), 6.69 (dd, 1H), 6.06 (m, 1H), 5.40 (m, 1H), 5.24 (m, 1H), 4.56 (m, 2H), 4.51 (s, 2H), 3.79 (s, 3H), 3.57 (s, 3H), 3.16 (m, 1H), 1.96 (m, 2H), 1.79 (m, 2H), 1.58 (m, 2H), 0.94-1.12 (overlapping m, 3H), 0.83 (s, 9H). MS (ESI): m/z 490 (M+H). HPLC A: 2.58 min.

Step E. 4-{[[6-(Allyloxy)-1-methyl-1H-benzimidazol-2-yl](4-tert-butylcyclohexyl)amino]methyl}benzoic acid To the title compound of Example 11 Step D (0.1 mmol, 51 mg) in 800 µL of dioxane was added a solution of LiOH (0.4 mmol, 10 mg) in 400 µL of $H_2O$. The resulting solution was stirred at ambient temperature overnight. The reaction mixture was taken up in a pH 7 buffer solution and EtOAc. The mixture was acidified with 2 N HCl until two clear layers formed after agitation. The organic layer was collected and the aqueous layer was washed with EtOAc. The combined organic layers were dried with $MgSO_4$ and concentrated under reduced pressure to afford the acid as a white solid. MS (ESI): m/z 476 (M+H). HPLC A: 2.33 min.

Step F. 4-{[[6-(Allyloxy)-1-methyl-1H-benzimidazol-2-yl](4-tert-butylcyclohexyl)-amino]methyl}-N-(1H-tetraazol-5-yl)benzamide To a solution of the title compound of Example 11 Step E (0.04 mmol, 20 mg), 1H-tetraazol-5-amine monohydrate (0.12 mmol, 12 mg), HOBt (0.08 mmol, 12 mg) and EDC (0.08 mmol, 15 mg) in 1 mL of DMF was added DIEA (0.08 mmol, 14 µL). The reaction was heated at 40° C. for 2 h, then concentrated under reduced pressure. The residue was taken up in ca. 2:1 dioxane/$H_2O$ and acidified with TFA, then purified by reverse-phase chromatography (Condition B). The product was lyophilized, affording the title compound as a white solid. $^1H$ NMR (500 MHz, $d_6$-DMSO): δ 12.33 (br s, 1H), 8.01 (d, 2H), 7.52 (d, 2H), 7.35 (d, 1H), 7.23 (br unres. m, 1H), 6.91 (br unres. m, 1H), 6.06 (m, 1H), 5.41 (dd, 1H), 5.27 (dd, 1H), 4.75 (s, 2H), 4.62 (d, 2H), 3.73 (s, 3H), 2.01 (m, 2H), 1.82 (m, 2H), 1.69 (m, 2H), 1.16 (m, 2H), 1.03 (m, 1H), 0.85 (s, 9H). one proton obscured by water. MS (ESI): m/z 543 (M+H). HPLC A: 2.19 min.

EXAMPLE 12

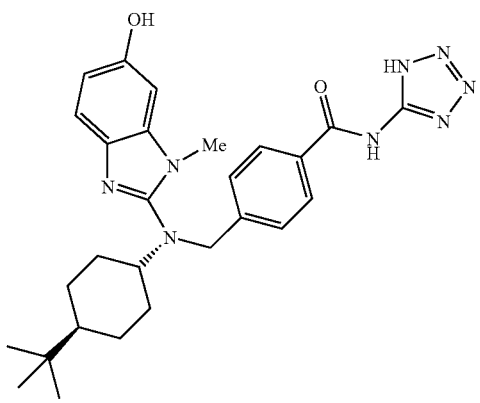

Step A. Methyl 4-{[(4-tert-butylcyclohexyl)(6-hydroxy-1-methyl-1H-benzimidazol-2-yl)amino]methyl}benzoate To a solution of the title compound of Example 11 Step D (0.6 mmol, 300 mg) and 1,3-dimethylbarbituric acid (0.72 mmol, 112 mg) in 3 mL of DCM was added under $N_2$ a solution of $Pd_2dba_3$ (0.025 mmol, 23 mg) and 1,4-bis(diphenylphosphino)-butane (0.05 mmol, 21 mg) in 0.5 mL of dry THF which had been incubated under $N_2$ for 15 min. After 30 min the reaction mixture was concentrated under reduced pressure, then purified by flash chromatography on silica eluting with a step gradient of 1% MeOH/DCM to 4% MeOH/DCM, affording the product as a white solid. MS (ESI): m/z 450 (M+H). HPLC A: 2.26 min.

Step B. 4-{[(4-tert-Butylcyclohexyl)(6-hydroxy-1-methyl-1H-benzimidazol-2-yl)amino]-methyl}benzoic acid To the title compound of Example 12 Step A (0.1 mmol, 50 mg) in 800 μL of dioxane was added LiOH (0.4 mmol, 10 mg) in 400 μL of $H_2O$. The resulting solution was stirred at 40° C. overnight. The reaction mixture was taken up in aqueous pH 7 buffer and EtOAc, and acidified with 2 N HCl until two clear layers formed after agitation. The organic layer was collected and the aqueous layer was washed with EtOAc. The combined organic layers were dried with $MgSO_4$ and concentrated under reduced pressure to afford the acid as a white solid, which was used without further purification. (HPLC A: 1.97 min).

Step C. 4-{[(4-tert-Butylcyclohexyl)(6-hydroxy-1-methyl-1H-benzimidazol-2-yl)amino]-methyl}-N-(1H-tetraazol-5-yl)benzamide To the product of Example 12 Step B (0.04 mmol), 1H-tetraazol-5-amine monohydrate (0.12 mmol, 12 mg), HOBt (0.08 mmol, 12 mg) and EDC (0.08 mmol, 15 mg) in 1 mL of DMF was added DIEA (0.08 mmol, 14 μL). The reaction was heated at 40° C. for 2.5 h, then concentrated under reduced pressure. The residue was taken up in ca. 2:1 dioxane/$H_2O$ and acidified with TFA, then purified by reverse-phase chromatography (Condition B). The product was lyophilized directly, affording the title compound as a white solid. $^1$H NMR (500 MHz, d6-DMSO): δ 12.35 (br s, 1H), 9.81 (br s, 1H), 8.01 (d, 2H), 7.52 (d, 2H), 7.28 (d, 2H), 6.91 (unres. d, 1H), 6.79 (dd, 1H), 4.75 (s, 2H), 3.69 (s, 3H), 2.01 (m, 2H), 1.83 (m, 2H), 1.69 (m, 2H), 1.16 (m, 2H), 1.04 (m, 11H), 0.85 (s, 9H). One proton obscured by $H_2O$. MS (ESI): m/z 503 (M+H). HPLC A: 1.85 min.

EXAMPLE 13

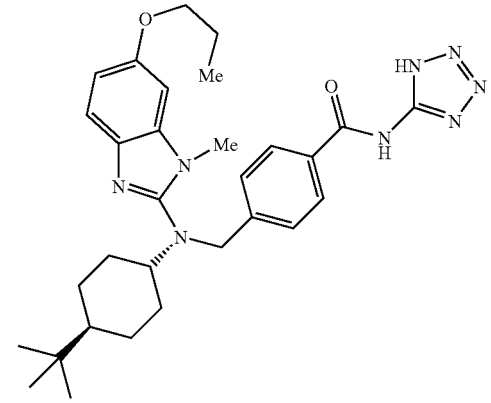

Step A. Methyl 4-{[(4-tert-butylcyclohexyl)(1-methyl-6-propoxy-1H-benzimidazol-2-yl)amino]methyl}benzoate To a solution of the title compound of Example 12 Step A (0.1 mmol, 45 mg), n-propanol (0.25 mmol, 19 μL) and diisopropyl azodicarboxylate (0.2 mmol, 37 μL) in 1 mL of DCM was added solid $Ph_3P$ (exothermic). After 20 min the reaction was complete. The product was isolated by flash chromatography on silica eluting with 10% EtOAc/hexanes, then 25% EtOAc/hexanes, affording the product as a clear oil. MS (ESI): m/z 492 (M+H). HPLC A: 2.68 min.

Step B 4-{[(4-tert-Butylcyclohexyl)(1-methyl-6-propoxy-1H-benzimidazol-2-yl)amino]-methyl}benzoate To the title compound of Example 13 Step A (0.07 mmol, 36 mg) in 0.8 mL of dioxane was added LiOH (0.3 mmol, 7 mg) in 0.4 mL of $H_2O$. The resulting solution was stirred at ambient temperature for 5 h. The reaction mixture was taken up in aqueous pH 7 buffer and EtOAc, and acidified with 2 N HCl until two clear layers formed after agitation. The organic layer was collected and the aqueous layer was washed 2× with EtOAc. The combined organic layers were dried with $MgSO_4$ and concentrated under reduced pressure to afford the acid as a white solid, which was used without further purification. (HPLC A: 2.42 min).

Step C. 4-{[(4-tert-Butylcyclohexyl)(1-methyl-6-propyloxy-1H-benzimidazol-2-yl)-amino]methyl}-N-(1H-tetraazol-5-yl)benzamide To a solution of the title compound of Example 13 Step B (0.02 mmol, 10 mg), 1H-tetraazol-5-amine monohydrate (0.06 mmol, 6 mg), HOBt (0.04 mmol, 6 mg) and DIEA (0.06 mmol, 10 μL) in 1 mL of DMF was added EDC (0.04 mmol, 8 mg). The reaction was allowed to stand at ambient temperature overnight, then concentrated under reduced pressure.

The residue was taken up in ca. 2:1 dioxane/H₂O and acidified with TFA, then purified by reverse-phase chromatography (Condition B). The product was lyophilized affording the title compound as a white solid. ¹H NMR (500 MHz, d6-DMSO): δ 12.34 (s, 1H), 8.00 (d, 2H), 7.53 (d, 2H), 7.43 (d, 1H), 7.20 (br m, 1H), 6.88 (m, 1H), 4.75 (s, 1H), 3.97 (t, 2H), 3.73 (s, 3H), 3.57 (br m, 1H), 2.01 (m, 2H), 1.82 (m, 2H), 1.62-1.78 (overlapping m, 4H), 1.16 (m, 2H), 0.95-1.08 (overlapping m, 4H), 0.85 (s, 9H). MS (ESI): m/z 545 (M+H). HPLC A: 2.28 min.

EXAMPLE 14

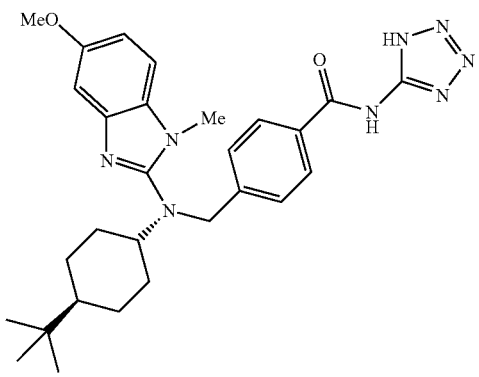

Step A. N-Methyl-4-methoxy-2-nitroaniline

To 4-methoxy-2-nitroaniline (10 mmol, 1.68 g) in 20 mL of DMF was added NaH (12 mmol, 480 mg of a 60% dispersion in mineral oil) (exothermic, H₂ evolution), affording a deep red slurry. After 15 min MeI (20 mmol, 1.2 mL) was added (exothermic). After 30 min the reaction was poured into a solution of brine and NaHCO₃, resulting in formation of a bright orange precipitate. The slurry was filtered and the filter cake was washed with H₂O. The solid was dried under reduced pressure, affording a bright orange solid. HPLC A: 1.77 min.

Step B. N-Methyl-4-methoxy-1,2-phenylenediamine

The title compound of Example 14 Step A (3 mmol, 547 mg) and 10% Pd—C (ca. 50 mg) were stirred in 10 mL of MeOH under H₂ (balloon). After 3 h the solution was nearly colorless. The reaction mixture was filtered over celite and filter cake was washed with MeOH. The combined filtrate was concentrated under reduced pressure affording a slightly orange solid. HPLC A: 0.44 min.

Step C. Methyl 4-{[(4-tert-butylcyclohexyl)(5-methoxy-1-methyl-1H-benzimidazol-2-yl)amino]methyl}benzoate To a solution of the title compound of Example 1 Step B (2.5 mmol, 759 mg) and DIEA (3 mmol, 0.52 mL) in 10 mL of DCM was added thiophosgene (2.5 mmol, 0.19 mL) (exothermic). After 15 min the title compound of Example 14 Step B (3 mmol, 456 mg) and DIEA (3 mmol, 0.52 mL) were added to the solution. After 30 min Hg(O₂CCF₃)₂ (2.5 mmol, 1.1 g) was added (exothermic), resulting in formation of an orange precipitate. After 30 min the solution was poured into NaHCO₃ (aq) containing Na₂S, and the slurry was filtered through celite, and the filter cake was washed with DCM. The organic phase was collected and the aqueous phase was extracted with 2×DCM. The combined organic phase was dried with Na₂SO₄ and concentrated under reduced pressure affording a tan solid. Purification by flash chromatography on silica eluting with 25% EtOAc/hexanes afforded the product as a white solid. ¹H NMR (500 MHz, CDCl₃) δ 7.92 (d, 2H), 7.45 (d, 2H), 7.20 (d, 1H), 7.08 (d, 1H), 6.84 (dd, 1H), 4.63 (s, 2H), 3.90 (s, 3H), 3.86 (s, 3H), 3.18 (m, 1H), 2.11 (m, 2H), 1.90 (m, 2H), 1.60 (m, 2H), 0.96-1.15 (overlapping m, 3H), 0.87 (s, 9H). MS (ESI): m/z 464 (M+H). HPLC A: 2.45 min.

Step D. 4-{[(4-tert-Butylcyclohexyl)(5-methoxy-1-methyl-1H-benzimidazol-2-yl)amino]methyl}benzoic acid To a solution of the title compound of Example 14 Step C (0.2 mmol, 93 mg) in 2 mL of dioxane was added LiOH (2 mmol, 48 mg) in 1 mL of H₂O. The reaction mixture was stirred at 40° C. for 1 h. The reaction mixture was taken up in dilute pH 7 buffer and EtOAc, and acidified with 2 N HCl until two clear layers formed after agitation. The organic layer was collected and the aqueous layer was washed 2× with EtOAc. The combined organic layers were dried with Na₂SO₄ and concentrated under reduced pressure to afford the acid as a white solid. HPLC A: 2.17 min.

Step E. 4-{[(4-tert-Butylcyclohexyl)(5-methoxy-1-methyl-1H-benzimidazol-2-yl)-amino]methyl}-N-(1H-tetraazol-5-yl)benzamide To a solution of the title compound of Example 14 Step D (0.1 mmol, 45 mg), 1H-tetraazol-5-amine monohydrate (0.2 mmol, 21 mg), HOBt (0.2 mmol, 31 mg) and DIEA (0.3 mmol, 52 μL) in 1 mL of DMF was added EDC (0.2 mmol, 38 mg). The reaction was heated to 40° C. for 3 h, then concentrated under reduced pressure. The residue was taken up in ca. 2:1 dioxane/H₂O and acidified with TFA, then purified by reverse-phase chromatography (Condition B). The product was lyophilized affording a white solid. ¹H NMR (500 MHz, d6-DMSO): δ 12.35 (s, 1H), 8.02 (d, 2H), 7.50-7.56 (overlapping m, 3H), 7.00 (d, 1H), 6.96 (m, 1H), 4.81 (s, 2H), 3.78 (s, 3H), 3.75 (s, 3H), 3.65 (m, 1H), 2.02 (m, 2H), 1.83 (m, 2H), 1.71 (m, 2H), 1.17 (m, 2H), 1.04 (m, 1H), 0.85 (s, 9H). MS (ESI): m/z 517 (M+H). HPLC A: 2.03 min.

EXAMPLE 15

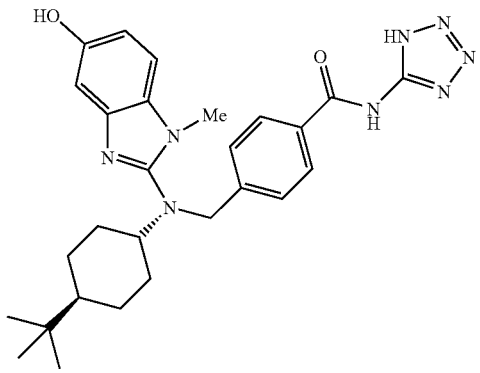

Step A. Methyl 4-{[(4-tert-butylcyclohexyl)(5-hydroxy-1-methyl-1H-benzimidazol-2-yl)amino]methyl}benzoate To a stirring solution of the title compound of Example 14 Step C (1 mmol, 464 mg) in 5 mL of DCM at −78° C. under $N_2$ was added dropwise $BBr_3$ (5 mmol, 5 mL of a 1M solution in DCM). The reaction was allowed to warm to ambient temperature. After 15 min the reaction was poured into stirring $NaHCO_3$ (gas evolution), and the product was extracted with DCM. The organic layer was dried with $Na_2SO_4$ and concentrated under reduced pressure, affording the product as a white solid. $^1$H NMR (500 MHz, $CDCl_3$): δ 7.90 (d, 2H), 7.44 (d, 2H), 7.28 (unres. m, 1H), 7.01 (d, 1H), 6.83 (dd, 1H), 4.64 (s, 2H), 3.89 (s, 3H), 3.58 (s, 3H), 3.20 (m, 1H), 2.10 (m, 2H), 1.89 (m, 2H), 1.59 (m, 2H), 0.98-1.14 (overlapping m, 3H), 0.86 (s, 9H). MS (ESI): m/z 450 (M+H). HPLC A: 2.30 min.

Step B. 4-{[(4-tert-Butylcyclohexyl)(5-hydroxy-1-methyl-1H-benzimidazol-2-yl)amino]methyl}benzoic acid To a solution of the title compound of Example 15 Step A (0.09 mmol, 40 mg) in 1 mL of dioxane was added LiOH (1 mmol, 24 mg) in 0.5 mL of $H_2O$. The reaction mixture was stirred at 40° C. for 1 h. The reaction mixture was taken up in dilute pH 7 buffer and EtOAc, and acidified with 2 N HCl until two clear layers formed after agitation. The organic layer was collected and the aqueous layer was washed 2× with EtOAc. The combined organic layers were dried with $Na_2SO_4$ and concentrated under reduced pressure to afford the acid as a beige solid. HPLC A: 2.01 min.

Step C. 4-{[(4-tert-Butylcyclohexyl)(5-hydroxy-1-methyl-1H-benzimidazol-2-yl)-amino-]methyl}1-N-(1H-tetraazol-5-yl)benzamide To a solution of the title compound of Example 15 Step B (0.02 mmol, 10 mg), 1H-tetraazol-5-amine monohydrate (0.2 mmol, 21 mg), HOBt (0.2 mmol, 31 mg) and DIEA (0.3 mmol, 52 µL) in 0.5 mL of DMF was added EDC (0.2 mmol, 38 mg). The reaction was heated to 40° C. 15 min, then allowed to stand at ambient temperature overnight. The reaction mixture was concentrated under reduced pressure. The residue was taken up in ca. 2:1 dioxane/$H_2O$ and acidified with TFA, then purified by reverse-phase chromatography (Condition B). The product was lyophilized affording the title compound as a white solid. MS (ESI): m/z 503 (M+H). HPLC A: 1.88 min.

EXAMPLE 16

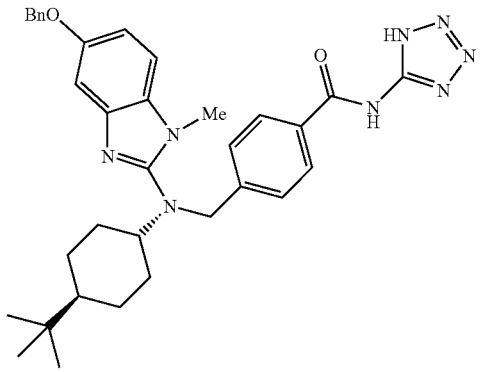

Step A. Methyl 4-{[(4-tert-butylcyclohexyl)(5-benzyloxy-1-methyl-1H-benzimidazol-2-yl)amino]methyl}benzoate To a solution of the title compound of Example 15 Step A (0.2 mmol, 90 mg), benzyl alcohol (0.5 mmol, 52 µL) and diisopropyl azodicarboxylate (0.4 mmol, 78 µL) in 1 mL of DCM was added solid $Ph_3P$ (0.4 mmol, 104 mg) (exothermic). After 1 h the product was isolated by flash chromatography on silica eluting with 10% EtOAc/hexanes, then 25% EtOAc/hexanes, affording the product as a waxy solid. HPLC A: 2.76 min.

Step B. 4-{[(4-tert-Butylcyclohexyl)(5-benzyloxy-1-methyl-1H-benzimidazol-2-yl)-amino]methyl}benzoic acid To a solution of the title compound of Example 16 Step A (0.2 mmol, 123 mg) in 2 mL of dioxane was added LiOH (2 mmol, 48 mg) in 1 mL of $H_2O$. The reaction mixture was stirred at 40° C. for 1.5 h. The reaction mixture was taken up in dilute pH 7 buffer and EtOAc, and acidified with 2 N HCl until two clear layers formed after agitation. The organic layer was collected and the aqueous layer was washed 2× with EtOAc. The combined organic layers were dried with $Na_2SO_4$ and concentrated under reduced pressure to afford the acid as a white solid. (HPLC A: 2.49 min).

Step C. 4-{[(4-tert-Butylcyclohexyl)(5-benzyloxy-1-methyl-1H-benzimidazol-2-yl)-amino]methyl}1-N-(1H-tetraazol-5-yl)benzamide To a solution of the title compound of Example 16 Step B (0.07 mmol, 37 mg), 1H-tetraazol-5-amine monohydrate (0.4 mmol, 41 mg), HOBt (0.4 mmol, 62 mg) and DIEA (0.6 mmol, 104 µL) in 1 mL of DMF was added EDC (0.4 mmol, 76 mg). The reaction was heated to 40° C. for 1 h, then allowed to stand at ambient temperature overnight. The reaction mixture was concentrated under reduced pressure. The residue was taken up in ca. 2:1 dioxane/$H_2O$ and acidified with TFA, then purified by reverse-phase chromatography (Condition B). The product was lyophilized affording the title compound as a white solid. $^1$H NMR (500 MHz, d6-DMSO): δ 12.35 (s, 1H), 8.01 (d, 2H), 7.53 (d, 2H), 7.51 (unres m, 1H), 7.43 (dd, 2H), 7.38 (dd, 2H), 7.32 (tt, 1H), 7.0-7.6 (overlapping m, 2H), 5.16 (s, 2H), 4.79 (s, 2H), 3.73 (s, 3H), 3.63 (m, 1H), 2.01 (m, 2H), 1.82 (m, 2H), 1.69 (m, 2H), 1.16 (m, 2H), 1.03 (m, 1H), 0.85 (s, 9H). MS (ESI): m/z 593 (M+H). HPLC A: 2.38 min.

Following the procedures outlined for Examples 1-16 the compounds listed in Tables 1-9 were prepared

TABLE 1

| Example | R¹ | R² | LCMS data: retention time(min)/M + H |
|---|---|---|---|
| 17 | Et | HN-tetrazol-5-ylamino | 2.02/501.2 |
| 18 | Et | HN-CH₂CH₂-CO₂H | 1.97/505.3 |
| 19 | Et | HN-CH₂-(1H-tetrazol-5-yl) | 1.98/515.3 |
| 20 | Et | HN-CH₂-CH(OH)-CO₂H | 1.88/521.3 |
| 21 | Pr | HN-tetrazol-5-ylamino | 2.15/515.3 |
| 22 | Pr | HN-CH₂CH₂-CO₂H | 2.1/519.3 |
| 23 | Pr | HN-CH₂-(1H-tetrazol-5-yl) | 2.06/529.3 |
| 24 | Pr | HN-CH₂-CH(OH)-CO₂H | 2.01/535.3 |
| 25 | cyclopentyl-C(CH₃)- | HN-tetrazol-5-ylamino | 2.30/541.3 |
| 26 | cyclopentyl-C(CH₃)- | HN-CH₂CH₂-CO₂H | 2.24/545.3 |
| 27 | cyclopentyl-C(CH₃)- | HN-CH₂-CH(OH)-CO₂H | 2.16/561.3 |

TABLE 1-continued

| Example | R¹ | R² | LCMS data: retention time(min)/M + H |
|---|---|---|---|
| 28 | benzyl | HN-tetrazole (5-amino-1H-tetrazole) | 2.34/563.3 |
| 29 | benzyl | HN-CH₂CH₂-CO₂H | 2.28/567.3 |
| 30 | benzyl | HN-CH₂-tetrazole | 2.27/577.3 |
| 31 | benzyl | HN-CH₂-CH(OH)-CO₂H | 2.2/583.3 |
| 32 | isobutyl | HN-tetrazole | 2.25/529.3 |
| 33 | isobutyl | HN-CH₂CH₂-CO₂H | 2.19/533.4 |
| 34 | isobutyl | HN-CH₂-tetrazole | 2.18/543.3 |
| 35 | isobutyl | HN-CH₂-CH(OH)-CO₂H | 2.11/549.3 |

TABLE 1-continued

| Example | R¹ | R² | LCMS data: retention time(min)/M + H |
|---|---|---|---|
| 36 | F-CH2CH2-C(CH3)- | HN-tetrazol-5-yl-NH | 1.99/519.3 |
| 37 | F-CH2CH2-C(CH3)- | HN-CH2-CO2H | 1.94/523.3 |
| 38 | F-CH2CH2-C(CH3)- | HN-CH2-tetrazol-5-yl | 1.92/533.3 |
| 39 | F-CH2CH2-C(CH3)- | HN-CH2-CH(OH)-CO2H | 1.86/539.3 |
| 40 | CH2=CH-CH2-C(CH3)- | HN-tetrazol-5-yl-NH | 2.13/513.4 |
| 41 | CH2=CH-CH2-C(CH3)- | HN-CH2-CO2H | 2.08/517.4 |
| 42 | CH2=CH-CH2-C(CH3)- | HN-CH2-CH(OH)-CO2H | 1.99/533.4 |
| 43 | HO-CH2CH2-C(CH3)- | HN-CH2-CO2H | 1.75/521.3 |
| 44 | HO-CH2CH2-C(CH3)- | HN-CH2-CH(OH)-CO2H | 1.68/537.3 |
| 45 | HO-CH2CH2CH2-C(CH3)- | HN-tetrazol-5-yl-NH | 1.84/531.4 |

TABLE 1-continued

| Example | R¹ | R² | LCMS data: retention time(min)/M + H |
|---|---|---|---|
| 46 | HO-(CH2)3-C(CH3)- | HN-CH2-CH(OH)-CO2H | 1.70/551.5 |
| 47 | (CH3)2N-CH2-CH2-C(CH3)- | HN-(tetrazole) | 1.54/544.5 |
| 48 | 4-F3CO-C6H4-CH2-C(CH3)- | HN-(tetrazole) | 2.59/657.4 |
| 49 | 4-F3CO-C6H4-CH2-C(CH3)- | HN-CH2-CH2-CO2H | 2.53/651.4 |
| 50 | 4-F3CO-C6H4-CH2-C(CH3)- | HN-CH2-CH(OH)-CO2H | 2.46/667.4 |
| 51 | Ph | HN-(tetrazole) | 2.30/549.3 |
| 52 | Ph | HN-CH2-CH2-CO2H | 2.24/553.4 |
| 53 | Ph | HN-CH2-(tetrazole) | 2.223/563.4 |

TABLE 1-continued

| Example | R¹ | R² | LCMS data: retention time(min)/M + H |
|---|---|---|---|
| 54 | Ph | HN–CH₂–C*H(OH)–CO₂H | 2.15/569.4 |
| 55 | 4-Cl-benzyl-C(CH₃)₂- | HN-tetrazol-5-yl | 2.48/597.3 |
| 56 | 4-Cl-benzyl-C(CH₃)₂- | HN–CH₂–CH₂–CO₂H | 2.43/601.3 |
| 57 | 4-Cl-benzyl-C(CH₃)₂- | HN–CH₂–C*H(OH)–CO₂H | 2.46/617.3 |
| 58 | 3-Cl-benzyl-C(CH₃)₂- | HN-tetrazol-5-yl | 2.44/597.3 |
| 59 | 3-Cl-benzyl-C(CH₃)₂- | HN–CH₂–CH₂–CO₂H | 2.38/601.3 |

TABLE 1-continued
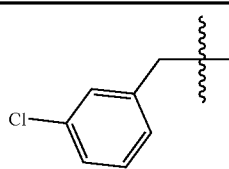
| Example | R¹ | R² | LCMS data: retention time(min)/M + H |
|---|---|---|---|
| 60 | 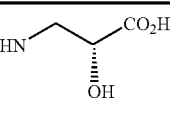 | 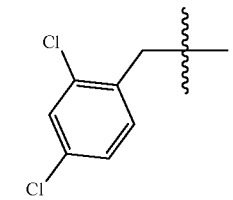 | 2.31/617.3 |
| 61 | 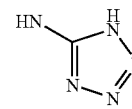 | 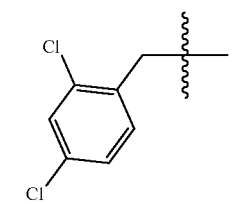 | 2.6/631.2 |
| 62 | 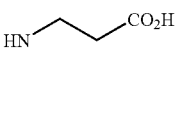 | 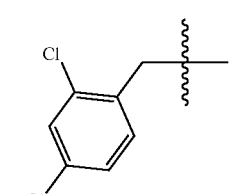 | 2.53/635.3 |
| 63 | 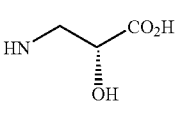 | 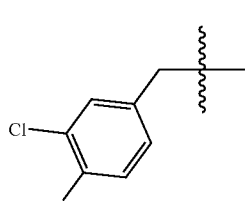 | 2.45/651.3 |
| 64 | 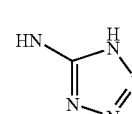 | 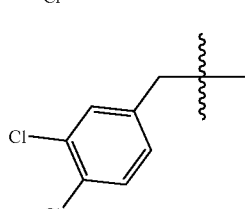 | 2.58/631.2 |
| 65 | 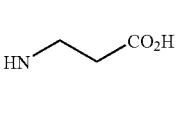 | HN⌒CO₂H | 2.54/635.2 |

TABLE 1-continued
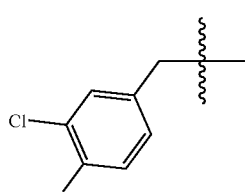
| Example | R¹ | R² | LCMS data: retention time(min)/M + H |
|---|---|---|---|
| 66 | 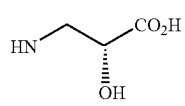 | 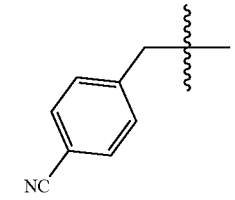 | 2.08/588.3 |
| 67 | 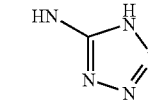 | 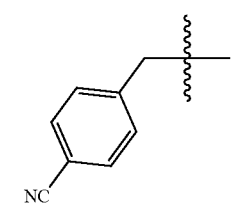 | 2.04/588.3 |
| 68 | 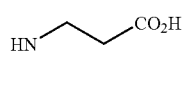 | 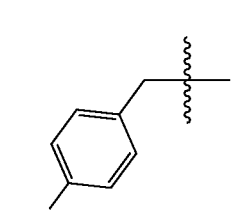 | 2.08/592.3 |
| 69 | 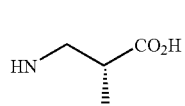 | 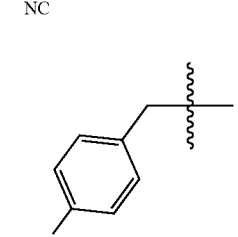 | 2.00/608.2 |
| 70 |  | | 2.24/608.3 |

TABLE 1-continued

| Example | R¹ | R² | LCMS data: retention time(min)/M + H |
|---|---|---|---|
| 71 | 4-O₂N-C₆H₄-CH₂- | -HN-CH₂CH₂-CO₂H | 2.19/612.3 |
| 72 | 4-O₂N-C₆H₄-CH₂- | -HN-CH₂-CH(OH)-CO₂H | 2.11/628.3 |
| 73 | 4-MeO-C₆H₄-CH₂- | -HN-(1H-tetrazol-5-yl) | 2.32/593.3 |
| 74 | 4-MeO-C₆H₄-CH₂- | -HN-CH₂CH₂-CO₂H | 2.26/597.4 |
| 75 | 4-MeO-C₆H₄-CH₂- | -HN-CH₂-CH(OH)-CO₂H | 2.18/613.3 |

TABLE 2

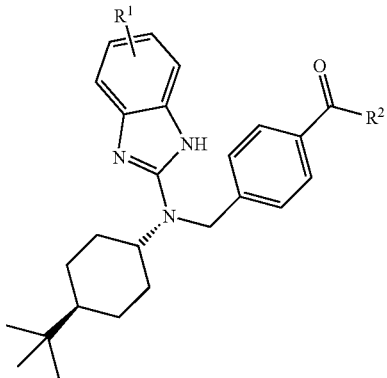

| Example | R¹ | R² | LCMS data: retention time (min)/M + H |
|---|---|---|---|
| 76 | 5-Me | HN-CH₂CH₂-CO₂H | 1.91/491.3 |
| 77 | 5-Me | HN-tetrazole | 1.96/487.3 |
| 78 | 5-CF₃O | HN-tetrazole | 2.09/557.2 |
| 79 | 5-CF₃O | HN-CH₂CH₂-CO₂H | 2.03/561.3 |
| 80 | 5-Cl | HN-tetrazole | 1.93/507.2 |
| 81 | 5-Cl | HN-CH₂CH₂-CO₂H | 1.88/511.2 |
| 82 | 5-Me | HN-CH₂-CH(OH)-CO₂H | 1.79/507.1 |
| 83 | 5-Me | HN-CH₂-tetrazole | 1.87/501.3 |
| 84 | 5,6-diCl | HN-tetrazole | 2.06/541.3 |
| 85 | 5,6-diCl | HN-CH₂CH₂-CO₂H | 2.01/545.3 |
| 86 | 5,6-diCl | HN-CH₂-CH(OH)-CO₂H | 1.92/561.3 |

TABLE 2-continued

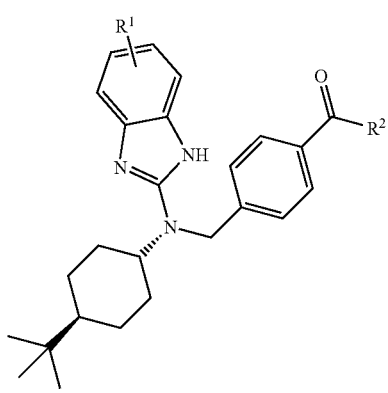

| Example | R¹ | R² | LCMS data: retention time (min)/M + H |
|---|---|---|---|
| 87 | 5,6-diCl | HN-CH₂-tetrazole | 2.00/555.3 |
| 88 | 5,6-diMe | HN-tetrazole | 2.03/501 |
| 89 | 5,6-diMe | HN-CH₂CH₂-CO₂H | 1.96/505 |
| 90 | 5,6-diMe | HN-CH₂-CH(OH)-CO₂H | 1.89/521 |
| 91 | 5,6-diMe | HN-CH₂-tetrazole | 1.96/515 |
| 92 | 5,6-diF | HN-tetrazole | 1.93/509 |
| 93 | 5,6-diF | HN-CH₂CH₂-CO₂H | 1.88/513 |
| 94 | 5,6-diF | HN-CH₂-CH(OH)-CO₂H | 1.79/529 |
| 95 | 5,6-diF | HN-CH₂-tetrazole | 1.87/523 |

TABLE 3

| Example | R¹ | R² | LCMS data: retention time (min)/M + H |
|---|---|---|---|
| 96 | 6-Me | HN–CH₂CH₂–CO₂H | 1.99/505.3 |
| 97 | 6-Me | HN-tetrazole | 2.04/501.3 |
| 98 | 6-Me | HN–CH₂CH(OH)–CO₂H | 1.911/521.4 |
| 99 | 5-CF₃ | HN–CH₂CH₂–CO₂H | 2.13/559.3 |
| 100 | 5-CF₃ | HN-tetrazole | 2.21/555.3 |
| 101 | 5,6-diCl | HN-tetrazole | 2.35/555.3 |
| 102 | 5,6-diCl | HN–CH₂CH₂–CO₂H | 2.24/5593 |
| 103 | 5,6-diCl | HN–CH₂CH(OH)–CO₂H | 2.14/575.3 |
| 104 | 5,6-diMe | HN-tetrazole | 2.13/515 |
| 105 | 5,6-diMe | HN–CH₂CH₂–CO₂H | 2.08/519 |
| 106 | 5,6-diMe | HN–CH₂CH(OH)–CO₂H | 2.00/535 |
| 107 | 5,6-diMe | HN–CH₂-tetrazole | 2.08/529 |
| 108 | 5,6-diF | HN-tetrazole | 2.08/523 |
| 109 | 5,6-diF | HN–CH₂CH₂–CO₂H | 2.01/527 |
| 110 | 5,6-diF | HN–CH₂CH(OH)–CO₂H | 1.93/543 |
| 110 | 5-OMe | HN–CH₂CH₂–CO₂H | 1.99/521.4 |
| 111 | 5-OMe | HN–CH₂CH(OH)–CO₂H | 1.91/537.4 |
| 112 | 5-OH | HN–CH₂CH₂–CO₂H | 1.83/507.3 |
| 113 | 5-OH | HN–CH₂CH(OH)–CO₂H | 1.74/523.3 |
| 114 | 5-OAllyl | HN-tetrazole | 2.37/593.3 |
| 115 | 5-OAllyl | HN–CH₂CH₂–CO₂H | 2.14/547.3 |
| 116 | 5-OBn | HN–CH₂CH₂–CO₂H | 2.32/597.3 |
| 117 | 6-OAllyl | HN–CH₂CH₂–CO₂H | 2.14/547 |
| 118 | 6-OAllyl | HN–CH₂CH(OH)–CO₂H | 2.07/563 |

TABLE 3-continued

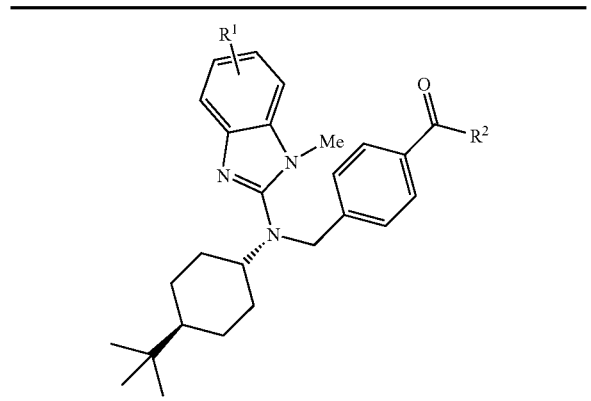

| Example | R[1] | R[2] | LCMS data: retention time (min)/M + H |
|---|---|---|---|
| 119 | 6-OAllyl | HN-CH2-tetrazole | 2.14/557 |
| 120 | 6-OH | HN-CH2CH2-CO2H | 1.8/503 |
| 121 | 6-OH | HN-CH2-CH(OH)-CO2H | 1.72/523 |
| 122 | 6-OH | HN-CH2-tetrazole | 1.79/517 |
| 123 | 5-OPr | HN-tetrazole | 2.27/545.3 |
| 124 | 5-OPr | HN-CH2CH2-CO2H | 2.22/549.3 |
| 125 | 5-OPr | HN-CH2-CH(OH)-CO2H | 2.14/565.3 |
| 126 | 5-OPr | HN-CH2-tetrazole | 2.21/559.3 |
| 127 | 5-O$^i$Pr | HN-tetrazole | 2.22/545.3 |
| 128 | 5-O$^i$Pr | HN-CH2CH2-CO2H | 2.17/549.3 |
| 129 | 5-O$^i$Pr | HN-CH2-CH(OH)-CO2H | 2.08/565.3 |

TABLE 3-continued

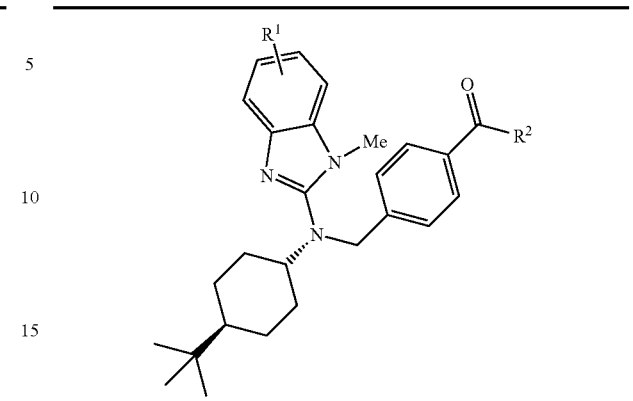

| Example | R[1] | R[2] | LCMS data: retention time (min)/M + H |
|---|---|---|---|
| 130 | 5-O$^i$Pr | HN-CH2-tetrazole | 2.16/559.3 |
| 131 | 6-OPr | HN-CH2CH2-CO2H | 2.23/549 |
| 132 | 6-OPr | HN-CH2-CH(OH)-CO2H | 2.14/565 |
| 133 | 5-OMe | HN-CH2-tetrazole | 1.97/531.3 |
| 134 | 5-O$^c$Pentyl | HN-tetrazole | 2.4/571.3 |
| 135 | 5-O$^c$Pentyl | HN-CH2CH2-CO2H | 2.36/575.3 |
| 136 | 5-O$^c$Pentyl | HN-CH2-CH(OH)-CO2H | 2.28/591.4 |
| 137 | 5-O$^c$Pentyl | HN-CH2-tetrazole | 2.34/585.3 |
| 138 | 5-O$^i$Bu | HN-tetrazole | 2.40/559.3 |
| 139 | 5-O$^i$Bu | HN-CH2CH2-CO2H | 2.35/563.4 |
| 140 | 5-O$^i$Bu | HN-CH2-CH(OH)-CO2H | 2.28/579.4 |

TABLE 3-continued

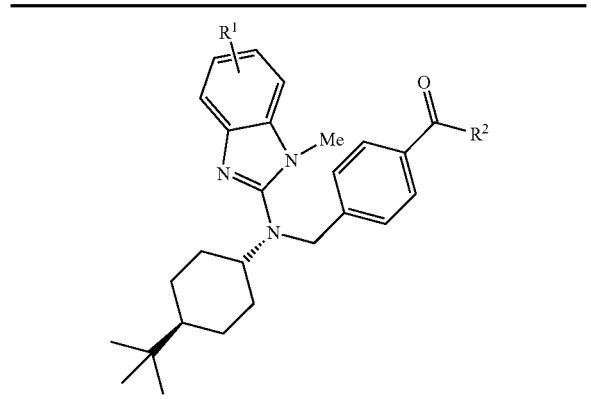

| Example | R¹ | R² | LCMS data: retention time (min)/M + H |
|---|---|---|---|
| 141 | 5-O$^i$Bu | HN-CH₂-tetrazole | 2.34/573.3 |
| 142 | 6-OBn | HN-tetrazole | 2.38/593 |
| 143 | 6-OBn | HN-CH₂CH₂-CO₂H | 2.33/597 |
| 144 | 6-OBn | HN-CH₂-CH(OH)-CO₂H | 2.27/613 |
| 145 | 6-O$^i$Pr | HN-tetrazole | 2.22/545 |
| 146 | 6-O$^i$Pr | HN-CH₂CH₂-CO₂H | 2.17/549 |
| 147 | 6-O$^i$Pr | HN-CH₂-CH(OH)-CO₂H | 2.10/565 |
| 148 | 6-OMe | HN-tetrazole | 2.02/517 |
| 149 | 6-OMe | HN-CH₂CH₂-CO₂H | 1.97/521 |
| 150 | 6-OMe | HN-CH₂-CH(OH)-CO₂H | 1.89/537 |
| 151 | 5-OBn | HN-CH₂-CH(OH)-CO₂H | 2.27/613.4 |

TABLE 3-continued

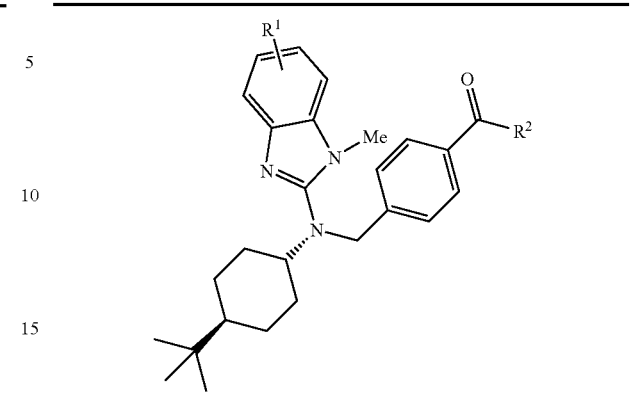

| Example | R¹ | R² | LCMS data: retention time (min)/M + H |
|---|---|---|---|
| 152 | 6-O$^c$Pentyl | HN-tetrazole | 2.42/571 |
| 153 | 6-O$^c$Pentyl | HN-CH₂CH₂-CO₂H | 2.37/575 |
| 154 | 6-O$^c$Pentyl | HN-CH₂-CH(OH)-CO₂H | 2.29/591 |
| 155 | 5-OEt | HN-tetrazole | 2.14/531.3 |
| 156 | 5-OEt | HN-CH₂CH₂-CO₂H | 2.008/535.4 |
| 157 | 5-O$^c$Bu | HN-tetrazole | 2.28/557.4 |
| 158 | 5-O$^c$Bu | HN-CH₂CH₂-CO₂H | 2.23/561.4 |
| 159 | 5-OCH₂$^c$Pr | HN-tetrazole | 2.24/557 |
| 160 | 5-OCH₂$^c$Pr | HN-CH₂CH₂-CO₂H | 2.19/561 |
| 161 | 5-OCH₂$^c$Hex | HN-tetrazole | 2.67/599 |
| 162 | 5-OCH₂$^c$Hex | HN-CH₂CH₂-CO₂H | 2.62/603 |
| 163 | 5-OCH₂CHF₂ | HN-tetrazole | 2.12/567.3 |

TABLE 3-continued

[Structure: benzimidazole with R¹ on benzene ring, N-Me, connected via N to (4-tert-butylcyclohexyl) and CH₂-phenyl-C(O)R²]

| Example | R¹ | R² | LCMS data: retention time (min)/M + H |
|---|---|---|---|
| 164 | 5-OCH₂CHF₂ | HN-CH₂CH₂-CO₂H | 2.08/571.3 |
| 165 | 5-OCH₂$^c$Bu | HN-(1H-tetrazol-5-yl) | 2.42/571 |
| 166 | 5-OCH₂$^c$Bu | HN-CH₂CH₂-CO₂H | 2.38/575 |
| 167 | 5-OCH₂$^c$Pent | HN-(1H-tetrazol-5-yl) | 2.54/585 |
| 168 | 5-OCH₂$^c$Pent | HN-CH₂CH₂-CO₂H | 2.49/589 |
| 169 | 6-OEt | HN-(1H-tetrazol-5-yl) | 2.15/531 |
| 170 | 6-OEt | HN-CH₂CH₂-CO₂H | 2.10/535 |
| 171 | 6-OCH₂$^c$Pr | HN-(1H-tetrazol-5-yl) | 2.27/557 |
| 172 | 6-OCH₂$^c$Pr | HN-CH₂CH₂-CO₂H | 2.22/561 |
| 173 | 6-O$^i$Bu | HN-(1H-tetrazol-5-yl) | 2.42/559 |
| 174 | 6-O$^i$Bu | HN-CH₂CH₂-CO₂H | 2.37/563 |

TABLE 4

[Structure: benzimidazole with R¹ on benzene ring, N-Et, connected via N to (4-tert-butylcyclohexyl) and CH₂-phenyl-C(O)R²]

| Example | R¹ | R² | LCMS data: retention time (min)/M + H |
|---|---|---|---|
| 175 | 5,6-diCl | HN-(1H-tetrazol-5-yl) | 2.51/569.2 |
| 176 | 6-OAllyl | HN-(1H-tetrazol-5-yl) | 2.32/557 |
| 177 | 6-OAllyl | HN-CH₂CH₂-CO₂H | 2.26/561 |
| 178 | 6-OAllyl | HN-CH₂-CH(OH)-CO₂H | 2.20/577 |
| 179 | 6-OAllyl | HN-CH₂-(1H-tetrazol-5-yl) | 2.27/571 |
| 180 | 5,6-diF | HN-(1H-tetrazol-5-yl) | 2.24/537.3 |
| 181 | 5,6-diF | HN-CH₂CH₂-CO₂H | 2.15/541.3 |
| 182 | 5,6-diF | HN-CH₂-CH(OH)-CO₂H | 2.06/577.3 |
| 183 | 6-OH | HN-(1H-tetrazol-5-yl) | 1.95/517 |
| 184 | 6-OH | HN-CH₂CH₂-CO₂H | 1.90/521 |
| 185 | 6-OH | HN-CH₂-CH(OH)-CO₂H | 1.82/537 |

TABLE 4-continued

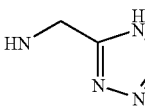

| Example | R¹ | R² | LCMS data: retention time (min)/M + H |
|---|---|---|---|
| 186 | 6-OH | HN-CH₂-tetrazole | 1.89/531 |

TABLE 5

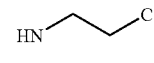

| Example | R¹ | R² | R³ | LCMS data: retention time(min)/M + H |
|---|---|---|---|---|
| 187 | Me | H | HN-CH₂CH₂-CO₂H | 1.97/589.1 |
| 188 | Me | H | HN-tetrazole | 2.01/585.2 |
| 189 | CF₃O | H | HN-CH₂CH₂-CO₂H | 2.11/659.1 |
| 190 | Cl | H | HN-tetrazole | 2.01/605.0 |
| 191 | Cl | H | HN-CH₂CH₂-CO₂H | 1.96/609 |

TABLE 5-continued

| Example | R¹ | R² | R³ | LCMS data: retention time(min)/M + H |
|---|---|---|---|---|
| 192 | Me | Me | HN-tetrazole | 2.17/599.2 |
| 193 | Me | Me | HN-CH₂CH₂-CO₂H | 2.10/603.2 |

TABLE 6

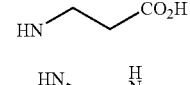

| Example | R¹ | R² | R³ | LCMS data: retention time(min)/M + H |
|---|---|---|---|---|
| 194 | H | H | HN-tetrazole | 1.89/493.3 |
| 195 | H | H | HN-CH₂CH₂-CO₂H | 1.83/497.3 |

TABLE 6-continued
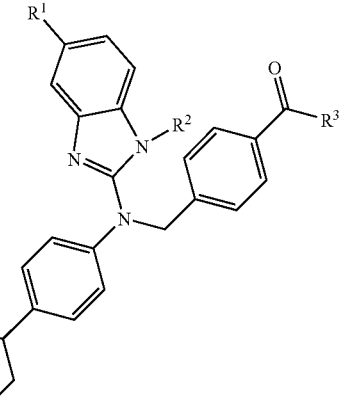
| Example | R¹ | R² | R³ | LCMS data: retention time(min)/M + H |
|---|---|---|---|---|
| 196 | H | H | 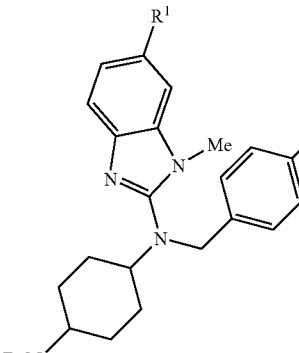 | 1.74/513.3 |
| 197 | H | Me | 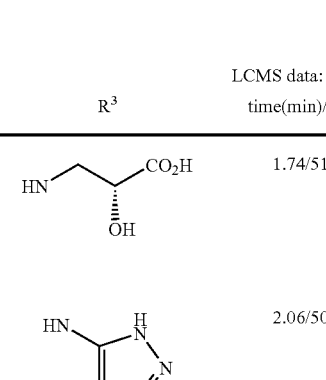 | 2.06/507.3 |
| 198 | H | Me | 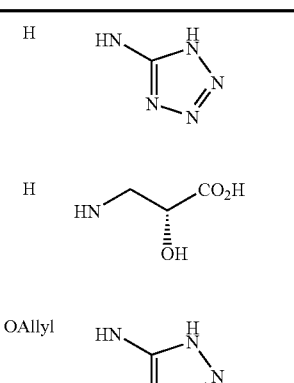 | 2.00/511.3 |
| 199 | H | Me | 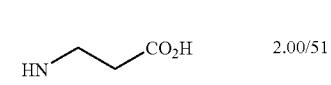 | 1.91/527.3 |
| 200 | OMe | Me | 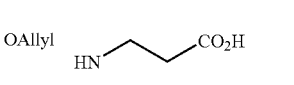 | 2.12/537.2 |
| 201 | OMe | Me | 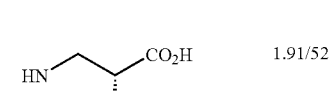 | 2.06/541.3 |
| 202 | OPr | Me | 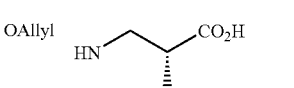 | 2.35/565.2 |
TABLE 7
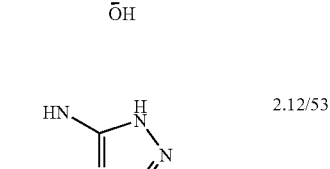
| Example | R¹ | R³ | LCMS data: retention time(min)/M + H |
|---|---|---|---|
| 203 | H | 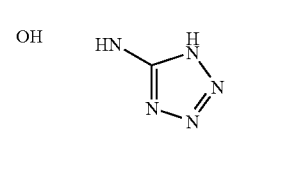 | 1.63/509 |
| 204 | H | 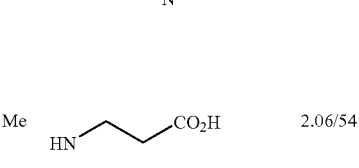 | 1.47/529 |
| 205 | OAllyl | 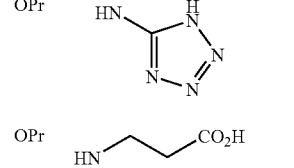 | 1.91/565 |
| 206 | OAllyl | 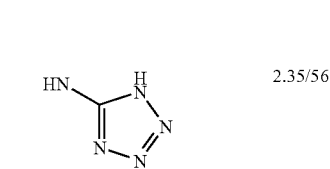 | 1.84/569 |
| 207 | OAllyl | 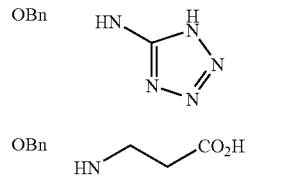 | 1.76/585 |
| 208 | OH | 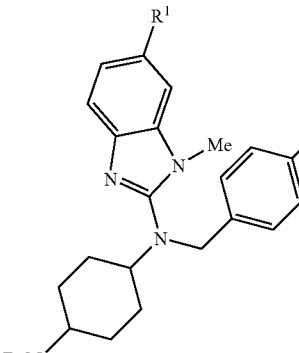 | 1.49/525 |
| 209 | OPr | 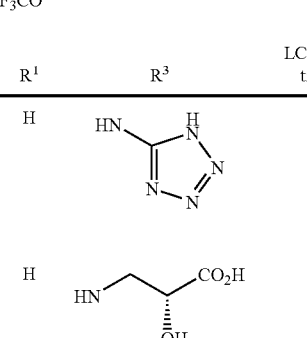 | 2.00/567 |
| 210 | OPr | 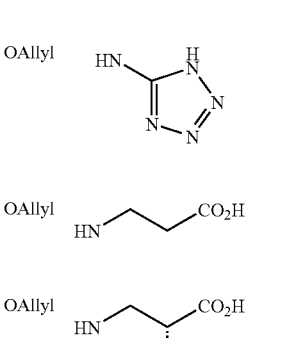 | 1.94/571 |
| 211 | OBn | 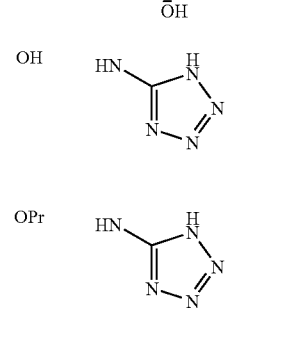 | 2.15/615 |
| 212 | OBn | 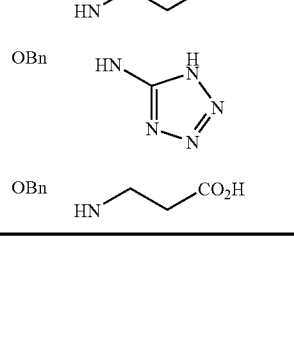 | 2.08/619 |

TABLE 8

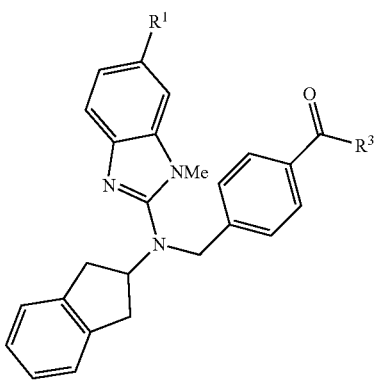

| Example | R[1] | R[3] | LCMS data: retention time(min)/M + H |
|---|---|---|---|
| 213 | H | HN-tetrazole | 1.46/465.2 |
| 214 | OAllyl | HN-tetrazole | 1.74/521 |
| 215 | OAllyl | HN-CH2CH2-CO2H | 1.68/525 |
| 216 | OAllyl | HN-CH2-CH(OH)-CO2H | 1.61/541 |

TABLE 9

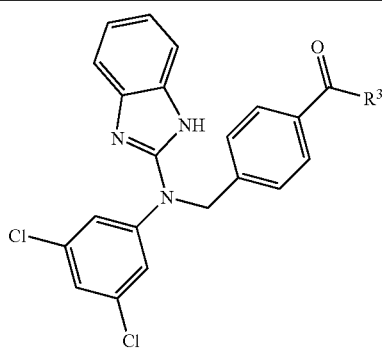

| Example | R[1] | R[3] | LCMS data: retention time(min)/M + H |
|---|---|---|---|
| 217 | H | HN-tetrazole | 1.38/479 |
| 218 | H | HN-CH2CH2-CO2H | 1.33/483 |
| 219 | H | HN-CH2-CH(OH)-CO2H | 1.23/499 |

TABLE 9-continued

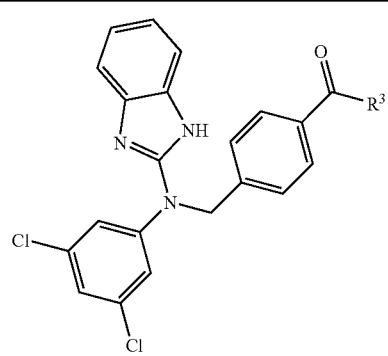

| Example | R[1] | R[3] | LCMS data: retention time(min)/M + H |
|---|---|---|---|
| 220 | H | HN-CH2-tetrazole | 1.305/493 |

EXAMPLE 221

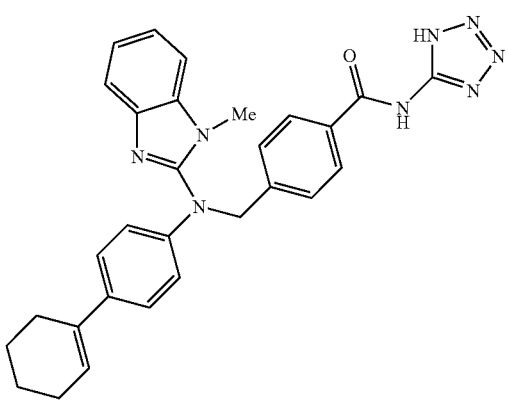

Step A. (1E)-1-(4-Bromophenyl)-3-cyclopentyltriaz-1-ene

Synthesis of 4-cyclohex-1-en-1-ylphenylamine described below followed the procedure in J. Org. Chem., 1993, 58, 2104.

To a suspension of 4-bromoaniline (58 mmol, 10 g) in 12 mL of conc. HCl at 0° C. was added dropwise an icecold solution of $NaNO_2$ (58 mmol, 4 g) in 5 mL of $H_2O$. The resulting mixture was stirred at 0° C. for 10 min, then poured into a solution of pyrrolidine (64 mmol, 5.33 mL) in 50 mL of 1N KOH in an icebath, and the reaction mixture was stirred for 30 min. The resulting brown precipitate was filtered, washed with $H_2O$, then recrystallized from 50 mL of EtOH, affording the product as a brown crystalline solid.

HPLC A: 2.41 min.

Step B. 1-{4-[(1E)-3-Cyclopentyltriaz-1-enyl] phenyl}cyclohexanol

To a stirring solution of the title compound in Example 221 Step A (3.9 mmol, 1 g) in 30 mL of ether cooled to −78° C. was added dropwise sec-butyllithium (7.8 mmol, 6.6 mL of a 1.3 M solution in hexanes). The resulting dark red solution was stirred for 30 min at −78° C. Cyclohexanone (7.9 mmol, 820 µL) was added dropwise, and the reaction mixture was allowed to warm to ambient temperature. The reaction was quenched by the addition of 30 mL of $H_2O$, and the reaction mixture was extracted with 2×30 mL of ether. The combined extracts were dried over $MgSO_4$ and concentrated under reduced pressure, affording a brown oil, which was taken on to Step C without further purification.

Step C. 4-Cyclohex-1-en-1-ylphenylamine

The title compound from Example 221 Step B was taken up in a solution of 150 mL of MeOH and 150 mL of 1N KOH and cooled in an ice bath. To the stirring solution was added in portions Al—Ni catalyst (10 g) (gas evolution). The reaction mixture was allowed to warm to ambient temperature and stirred for 5 h, after which time a grey precipitate formed. The slurry was filtered over celite and the filtrate was concentrated under reduced pressure to remove most of the MeOH. The remaining solution was extracted with 2×100 mL of ether. The organic phase was concentrated under reduced pressure affording a green oil. The oil was dissolved in 100 mL of benzene, and 50 mg of TsOH, followed by 1 mL of conc. HCl were added to the solution. The resulting reaction mixture was heated to reflux for 30 min, then allowed to cool to ambient temperature. The solution was washed with 100 mL of saturated $NaHCO_3$, and the organic layer was dried over $MgSO_4$ and concentrated under reduced pressure. The residue was purified by flash chromatography on silica eluting with 10% EtOAc/hexanes, then 15% EtOAc/hexanes, affording the product as a light amber oil. MS (ESI): m/z 174 (M+H). HPLC A: 1.30 min.

Step D. N-(4-Cyclohex-1-en-1-ylphenyl)-1-methyl-1H-benzimidazol-2-amine

To a solution of the title compound from Example 221 Step C (0.59 mmol, 102 mg) and DIEA (0.65 mmol, 1130 □L) in 1 mL of DCM was added thiophosgene (0.62 mmol, 43 µL). After 30 min, N-methyl-1,2-phenylenediamine (0.9 mmol, 100 µL) was added and the reaction was stirred overnight at ambient temperature. The reaction mixture was concentrated under reduced pressure and the residue was taken up in 1 mL of DMF. MeI (5.9 mmol, 360 µL) was added, and the solution was warmed to 50° C. for 30 min. The reaction mixture was concentrated under reduced pressure, and crude product was purified by flash chromatography on silica eluting with 0.5:1:98.5 $Et_3$N/MeOH/DCM, affording the product as a white solid. MS (ESI): m/z 304 (M+H). HPLC A: 1.90 min.

Step E. Methyl 4-{[(4-cyclohex-1-en-1-ylphenyl)(1-methyl-1H-benzimidazol-2-yl)-amino]methyl}benzoate To the title compound from Example 221 Step D (0.53 mmol, 161 mg) and NaH (0.80 mmol, 32 mg of a 60% dispersion in mineral oil) was added 1 mL of DMF (gas evolution). The mixture was stirred for 30 min at ambient temperature, then methyl 4-(bromomethyl)benzoate (0.80 mmol, 182 mg) was added. After 30 min the reaction mixture was concentrated under reduced pressure, and the residue was purified by flash chromatography on silica eluting with a step gradient of 10% EtOAc/hexanes, 15% EtOAc/hexanes, and 20% EtOAc/hexanes, affording the product as a white solid. $^1$H NMR (500 MHz, $CDCl_3$) □ 8.02 (d, 2H), 7.77 (m, 1H), 7.58 (d, 2H), 7.36 (d, 2H), 7.20-7.36 (overlapping m, 4H), 6.93 (d, 2H) 6.16 (m, 1H), 5.44 (s, 2H), 3.93 (s, 3H), 3.31 (s, 3H), 2.40 (m, 2H), 2.25 (m, 2H), 1.82 (m, 2H), 1.69 (m, 2H). MS (ESI): m/z 452 (M+H). HPLC A: 2.42 min.

Step F. 4-{[(4-Cyclohex-1-en-1-ylphenyl)(1-methyl-1H-benzimidazol-2-yl)amino]-methyl}benzoic acid To the title compound of Example 221 Step E (0.26 mmol, 117 mg) in 2 mL of dioxane was added a solution of LiOH (2.6 mmol, 62 mg) in 1 mL of $H_2O$. The reaction was stirred at 50° C. for 30 min. The dioxane was removed under reduced pressure and the remaining aqueous solution was acidified with 2 N HCl. The resulting precipitate was filtered, washed with $H_2O$ and dried under reduced pressure, affording the product as a white solid. HPLC A: 2.11 min.

Step G. 4-{[(4-Cyclohex-1-en-1-ylphenyl)(1-methyl-1H-benzimidazol-2-yl)amino]-methyl}-N-(1H-tetraazol-5-yl)benzamide To a solution of the title compound of Example 221 Step F (0.11 mmol, 50 mg), 1H-tetraazol-5-amine monohydrate (0.23 mmol, 24 mg), HOBt (0.29 mmol, 43 mg) and EDC (0.46 mmol, 88 mg) in 1 mL of DMF was added DIEA (0.57 mmol, 100 µL). The reaction mixture was allowed to stand at ambient temperature overnight, then poured into a mixture of dilute pH 7 buffer/EtOAc, which was acidified with 2 N HCl until two clear layers formed after agitation. The organic phase was concentrated under reduced pressure and the residue was purified by reverse-phase chromatography (Condition B) and lyophilized, affording a white solid. $^1$H NMR (500 MHz, DMSO) δ 8.06 (d, 2H), 7.68 (d, 2H), 7.55 (m, 2H), 7.42 (d, 2H), 7.34 (m, 2H), 7.20 (d, 2H), 6.18 (m, 1H), 5.38 (s, 2H), 3.31 (s, 3H), 2.35 (m, 2H), 2.18 (m, 2H), 1.73 (m, 2H), 1.60 (m, 2H). MS (ESI): m/z 505 (M+H). HPLC A: 1.99 min.

EXAMPLE 222

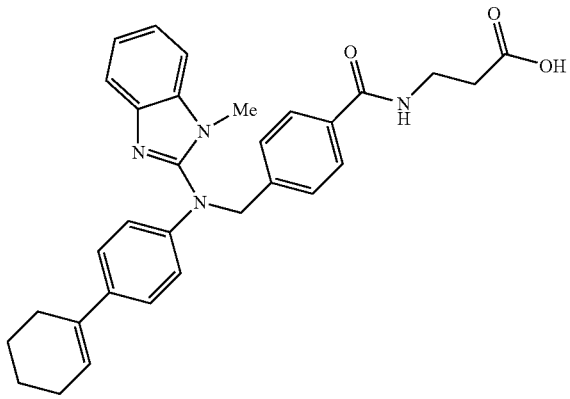

N-(4-{[(4-Cyclohex-1-en-1-ylphenyl)(1-methyl-1H-benzimidazol-2-yl)amino]methyl}-benzoyl)-□-alanine To a solution of the title compound of Example 1 Step F (0.01 mmol, 5 mg), the hydrochloride salt of β-alanine tert-butyl ester (0.02 mmol, 4 mg), HOBt (0.03 mmol, 4 mg) and EDC (0.05 mmol, 9 mg) in 0.1 mL of DMF was added DIEA (0.06 mmol, 10 µL). The reaction mixture was allowed to stand at ambient temperature for 4 h, then partitioned between EtOAc/brine. The organic layer was collected and the aqueous phase was extracted twice with EtOAc. The combined organic phase was concentrated under reduced pressure. The residue was treated with 0.5 mL of 2:30:68H$_2$O/TFA/DCM for 30 min and the solution was concentrated under reduced pressure. The residue was purified by reverse-phase chromatography (Condition B) and then lyophilized, affording a white solid. $^1$H NMR (500 MHz, CD$_3$OD) δ 7.82 (d, 2H), 7.58-7.43 (n, 8H), 7.32 (d, 2H), 6.21 (m, 1H), 5.38 (s, 2H), 3.61 (2H, t), 3.37 (s, 3H), 2.63 (2H, t), 2.40 (m, 2H), 2.23 (m, 2H), 1.81 (m, 2H), 1.70 (m, 2H). MS (ESI): m/z 509 (M+H). HPLC A: 1.92 min.

EXAMPLE 223

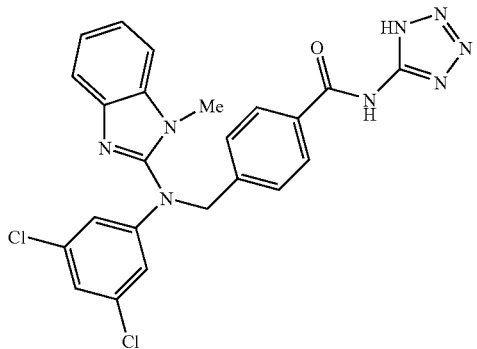

Step A. N-(3,5-Dichlorophenyl)-1-methyl-1H-benzimidazol-2-amine

To a solution of 3,5-dichloroaniline (6.2 mmol, 1.0 g) and DIEA (6.8 mmol, 1.2 mL) in 10 mL of DCM was slowly added thiophosgene (6.2 mmol, 472 µL) (exothermic). After 30 min, N-methyl-1,2-phenylenediamine (6.2 mmol, 704 µL) was added and the reaction mixture was allowed to stand at ambient temperature for 1 h. MeI (6.2 mmol, 386 µL), followed by DIEA (6.8 mmol, 1.2 mL) were then added, and the reaction mixture was allowed to stand at ambient temperature overnight. The crude reaction was partitioned between DCM/brine. The organic layer was collected and the aqueous phase was extracted twice with DCM. The combined organic layer was concentrated under reduced pressure, and the residue was purified by flash chromatography on silica eluting with 2% MeOH/DCM and 4% MeOH/DCM, affording the product as a tan solid. $^1$H NMR (500 MHz, d6-DMSO) δ 9.35 (s, 1H), 8.04 (s, 2H), 7.48 (m, 2H), 7.36 (m, 2H), 7.08-7.14 (overlapping m, 2H), 3.73 (s, 3H). MS (ESI): m/z 292 (M+H). HPLC A: 1.38 min.

Step B. Methyl 4-{[(3,5-dichlorophenyl)(1-methyl-1H-benzimidazol-2-yl)amino]-methyl}benzoate To the title compound from Example 223 Step A (0.21 mmol, 60 mg) and NaH (0.24 mmol, 6 mg of a 60% slurry in mineral oil) was added 0.5 mL of DMF (gas evolution). After 15 min, methyl-4-(bromomethyl)benzoate (0.24 mmol, 55 mg) was added and the reaction mixture was allowed to stand at ambient temperature overnight. The mixture was partitioned between DCM and NaHCO$_3$. The organic phase was collected and the aqueous phase was extracted 2× with DCM. After 30 min the reaction mixture was concentrated under reduced pressure, and the residue was purified by flash chromatography on silica eluting with 2% MeOH/DCM. The product was further purified by reverse phase HPLC (Condition B). The combined HPLC fractions were neutralized with saturated NaHCO$_3$ and extracted with DCM. The organic phase was dried over MgSO$_4$ and concentrated under reduced pressure to afford the product as a white solid. $^1$H NMR (500 MHz, d6-DMSO) δ 7.94 (d, 2H), 7.68 (d, 2H), 7.61 (d, 1H), 7.52 (d, 1H), 7.21-7.29 (overlapping m, 2H), 7.10 (t, 1H), 6.79 (d, 2H), 5.27 (s, 2H), 3.83 (s, 3H), 3.50 (s, 3H). MS (ESI): m/z 440 (M+H). HPLC A: 2.16 min.

Step C. 4-{[(3,5-Dichlorophenyl)(1-methyl-1H-benzimidazol-2-yl)amino]methyl}-benzoic acid To the title compound of Example 223 Step B (0.2 mmol, 85 mg) in 1.6 mL of dioxane was added a solution of LiOH (0.8 mmol, 19 mg) in 0.8 mL of H$_2$O. The reaction was allowed to stir at ambient temperature overnight. The crude reaction mixture was poured into pH 7 buffer/EtOAc, which was acidified with 2 N HCl until two clear layers formed after agitation. The organic phase was collected and the aqueous phase was extracted twice with EtOAc. The combined organic phase was dried over MgSO$_4$, then concentrated under reduced pressure to afford the product as a white foam. MS (ESI): m/z 426 (M+H). HPLC A: 1.79 min.

Step D. 4-{[(3,5-Dichlorophenyl)(1-methyl-1H-benzimidazol-2-yl)amino]methyl}-N-(1H-tetraazol-5-yl)benzamide To a solution of the title compound of Example 223 Step C (0.16 mmol, 68 mg), 1H-tetraazol-5-amine monohydrate (0.48 mmol, 49 mg), HOBt (0.32 mmol, 49 mg) and EDC (0.32 mmol, 61 mg) in 1 mL of DMF was added DIEA (0.48 mmol, 83 µL). The reaction mixture was warmed to 40° C. for 2 h, then concentrated under reduced pressure. The residue was purified by reverse-phase chromatography (Condition B). The product was lyophilized, affording a white solid. $^1$H NMR (500 MHz, d6-DMSO) δ 12.38 (s, 1H), 8.07 (d, 2H), 7.73 (d, 2H), 7.63 (m, 1H), 7.56 (m, 1H), 7.24-7.33 (overlapping m, 2H), 7.15 (t, 1H), 6.90 (d, 2H), 5.31 (s, 2H), 3.53 (s, 3H). MS (ESI): m/z 493 (M+H). HPLC A: 1.69 min.

EXAMPLE 224

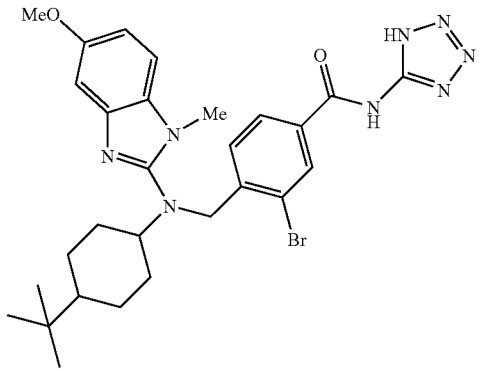

Step A. Methyl 3-bromo-4-methylbenzoate

To a solution of 2.0 g (9.3 mmol) of 3-bromo-4-methylbenzoic acid in 25 mL of dichloromethane was added 5.6 mL (11.2 mmol) of oxalyl chloride and 100 µL of N,N-dimethylformamide. The resultant mixture was stirred at ambient temperature for 2 hours, concentrated in vacuo, and the residue suspended in methanol. The solution was concentrated in vacuo and the residue purified by flash column chromatography (biotage) using 5% ethyl acetate/hexanes as eluent to provide the title compound. $^1$H NMR (500 MHz, CDCl$_3$) δ 8.23 (s, 1H), 7.90 (d, 1H, J=8 Hz), 7.33 (d, 1H, J=8 Hz), 3.94 (s, 3H), 2.48 (s, 3H). HPLC/MS (ESI) m/z (M+H)=231.0 (3.63 min).

Step B. Methyl 3-bromo-4-bromomethylbenzoate

To a solution of 1.09 g (4.76 mmol) of the product from Example 224 Step A in 7 mL of carbon tetrachloride was added 847 mg (4.76 mmol) of N-bromosuccinimide and 78 mg (0.48 mmol) of 2,2'-azobisisobutyronitrile. The resultant mixture was heated at reflux for 2 5 hours, cooled to ambient temperature, diluted with carbon tetrachloride and filtered through celite. The filtrate was concentrated in vacuo and carried on without purification assuming 100% conversion. HPLC/MS (ESI) m/z (M+H)=310.9 (3.68 min).

Step C. Methyl 3-bromo-4-{[(4-tert-butylcyclohexyl)amino]methyl}benzoate

To a solution of the product from Example 224 Step B (assume 4.76 mmol) in 5 mL of N,N-dimethylformamide was added 1.02 mL (5.71 mmol) of 4-tert-butylcyclohexylamine and 1.7 mL (9.76 mmol) of N,N-diisopropylethylamine. The resultant mixture was stirred at ambient temperature for 3 hours, diluted with ethyl acetate and the organic layer washed sequentially with three portions of water and one portion of saturated sodium chloride solution. The organic layer was dried over magnesium sulfate, filtered, and concentrated in vacuo. The residue was purified by flash column chromatography (biotage) using 5% ethyl acetate/hexanes as eluent to provide both the cis isomer and the desired trans isomer. $^1$H NMR (500 MHz, CD$_3$OD) δ 8.18 (s, 1H), 7.97 (d, 1H, J=8 Hz), 7.58 (d, 1H, J=8 Hz), 3.93 (s, 2H), 3.91 (s, 3H), 2.43-2.37 (m, 1H), 2.08-2.01 (m, 2H), 1.85-1.79 (s, 2H), 1.19-4.99 (m, 5H), 0.86 (s, 9H). HPLC/MS (ESI) m/z (M+H)=384.2 (2.47 min.).

Step D. Methyl 3-bromo-4-{[(4-tert-butylcyclohexyl)(5-methoxy-1-methyl-1H-benz-imidazol-2-yl)amino]methyl}benzoate To a solution of the title compound from Example 224 Step C (0.5 mmol, 191 mg) and DIEA (0.6 mmol, 104 µL) in 2 mL of DCM was added thiophosgene (0.5 mmol, 38 µL) (exothermic). After 15 min, the title compound from Example 14 Step B (0.6 mmol, 91 mg) was added to the reaction, followed by DIEA (0.6 mmol, 104 µL). The reaction mixture was allowed to stand at ambient temperature for 1 h, then Hg(O$_2$CCF$_3$)$_2$ (0.6 mmol, 256 mg) was added (exothermic), affording a pinkish precipitate. After 30 min the solution was poured into saturated NaHCO$_3$ containing Na$_2$S, and the slurry was filtered through celite. The filter cake was washed with DCM. The organic layer of the filtrate and washings was collected and the aqueous phase was extracted with 2×DCM. The combined organic phase was dried with Na$_2$SO$_4$ and concentrated under reduced pressure affording a brown residue. Purification by flash chromatography on silica eluting with 20% EtOAc/hexanes afforded the product as a slightly green foam. MS (ESI): m/z 542 (M+H), 544. HPLC A: 2.67 min.

Step E. 3-Bromo-4-{[(4-tert-butylcyclohexyl)(5-methoxy-1-methyl-1H-benzimidazol-2-yl)amino]methyl}benzoic acid To the title compound of Example 224 Step D (0.07 mmol, 40 mg) in 2 mL of dioxane was added a solution of LiOH (1 mmol, 24 mg) in 1 mL of H$_2$O. The reaction was allowed to stir at 40° C. for 1.5 h. The crude reaction mixture was poured into pH 7 buffer/EtOAc, which was acidified with 2 N HCl until two clear layers formed after agitation. The organic phase was collected and the aqueous phase was extracted twice with EtOAc. The combined organic phase was dried over Na$_2$SO$_4$, then concentrated under reduced pressure to afford the product as a slightly yellow-green foam. HPLC A: 2.32 min.

Step F. 3-Bromo-4-{[(4-tert-butylcyclohexyl)(5-methoxy-1-methyl-1H-benzimidazol-2-yl)amino]methyl}-N-(1H-tetraazol-5-yl)benzamide To a solution of the title compound of Example 223 Step E (0.07 mmol, 40 mg), 1H-tetraazol-5-amine monohydrate (0.2 mmol, 21 mg), HOBt (0.2 mmol, 31 mg) and EDC (0.2 mmol, 38 mg) in 1 mL of DMF was added DIEA (0.3 mmol, 52 µL). The reaction mixture was warmed to 40° C. for 2 h, then concentrated under reduced pressure. The residue was purified by reverse-phase chromatography (Condition C). The product was lyophilized, affording a white solid. $^1$H NMR (500 MHz, d6-DMSO) δ 12.50 (s, 1H), 8.36 (d, 1H), 7.98 (dd, 2H), 7.60 (d, 2H), 7.51 (dd, 1H), 7.01 (d, 1H), 6.95 (d, 1H), 4.78 (s, 2H), 3.79 (s, 3H), 3.76 (s, 3H), 1.98 (m, 2H), 1.80 (m, 2H), 1.61 (m, 2H), 1.15 (m, 2H), 1.03 (m, 1H), 0.84 (s, 9H). MS (ESI): m/z 595 (M+H), 597. HPLC A: 2.17 min.

EXAMPLE 225

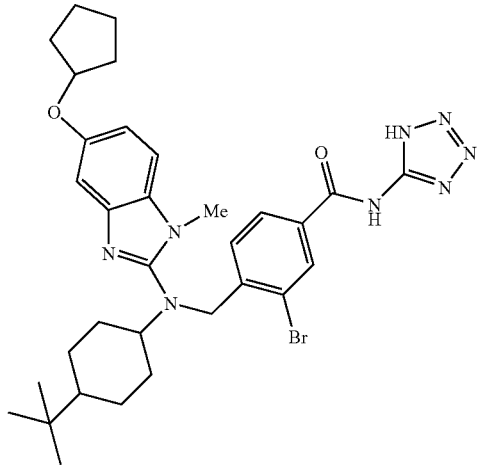

Step A. Methyl 3-bromo-4-{[(4-tert-butylcyclohexyl)(5-hydroxy-1-methyl-1H-benz-imidazol-2-yl)amino]methyl}benzoate To a stirring solution of the title compound of Example 224 Step D (0.1 mmol, 54 mg) in 1 mL of DCM cooled to −78° C. under N$_2$ was added dropwise BBr$_3$ (0.3 mmol, 0.3 mL of a 1M solution in DCM). The reaction was allowed to warm to ambient temperature. After 1 h the reaction was taken up in 10 mL of MeOH and then concentrated under reduced pressure. The residue was purified by flash chromatography on silica eluting with 50% EtOAc/hexanes, affording the product as a white solid. HPLC A: 2.54 min.

Step B. Methyl 3-bromo-4-{[(4-tert-butylcyclohexyl)(5-cyclopentyloxy-1-methyl-1H-benz-imidazol-2-yl)amino]methyl}benzoate To a solution of the title compound of Example 225 Step A (0.08 mmol, 43 mg), cyclopentyl alcohol (0.25 mmol, 23 μL) and diisopropyl azodicarboxylate (0.25 mmol, 49 μL) in 0.7 mL of DCM was added Ph₃P (0.25 mmol, 66 mg) (exothermic). After 2 h the product was isolated by flash chromatography on silica eluting with 10% EtOAc/hexanes, then 20% EtOAc/hexanes, affording a waxy yellow solid. HPLC A: 2.97 min.

Step C. 3-Bromo-4-{[(4-tert-butylcyclohexyl)(5-cyclopentyloxy-1-methyl-1H-benz-imidazol-2-yl)amino]methyl}benzoic acid To the title compound of Example 225 Step B (0.07 mmol, 57 mg) in 2 mL of dioxane was added a solution of LiOH (1 mmol, 24 mg) in 1 mL of H₂O. The reaction was allowed to stir at 40° C. for 10 min, then stirred at ambient temperature overnight. The crude reaction mixture was poured into pH 7 buffer/EtOAc, then was acidified with 2 N HCl until two clear layers formed after agitation. The organic phase was collected and the aqueous phase was extracted twice with EtOAc. The combined organic phase was dried over $Na_2SO_4$, then concentrated under reduced pressure to afford an oily residue. The residue was triturated in hexanes to afford a beige solid. MS (ESI): m/z 582 (M+H), 584. HPLC A: 2.66 min.

Step D. 3-Bromo-4-{[(4-tert-butylcyclohexyl)(5-cyclopentyloxy-1-methyl-1H-benzimidazol-2-yl)amino]methyl}-N-(1H-tetraazol-5-yl)benzamide To a solution of the title compound of Example 225 Step C (0.06 mmol, 36 mg), 1H-tetrazol-5-amine monohydrate (0.2 mmol, 21 mg), HOBt (0.2 mmol, 31 mg) and EDC (0.2 mmol, 38 mg) in 1 mL of DMF was added DIEA (0.3 mmol, 52 μL). The reaction mixture was warmed to 40° C. for 1 h, then concentrated under reduced pressure. The residue was purified by reverse-phase chromatography (Condition D). Lyophilization afforded the product as a white solid. $^1$H NMR (500 MHz, d6-DMSO) δ 12.49 (s, 1H), 8.35 (d, 2H), 7.97 (dd, 2H), 7.59 (d, 1H), 7.49 (d, 1H), 6.96 (d, 1H), 6.91 (dd, 1H), 4.83 (m, 1H), 4.77 (s, 2H), 3.74 (s, 3H), 3.64 (m, 1H), 1.96 (m, 2H), 1.88 (m, 2H), 1.64-1.74 (overlapping m, 4H), 1.52-1.64 (overlapping m, 4H), 1.13 (m, 2H), 1.01 (m, 1H), 0.82 (s, 9H). MS (ESI): m/z 649 (M+H), 651. HPLC A: 2.51 min.

Following the procedures outlined for Examples 1-16 and 221-225, the compounds listed in Tables 10-12 were prepared

TABLE 10

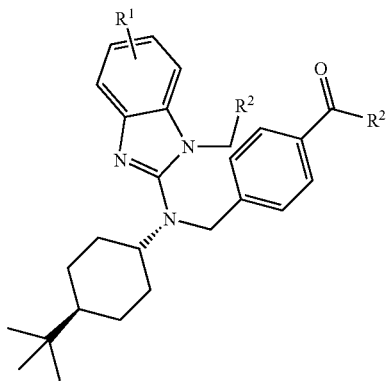

| Example | R¹ | R² | R³ | LCMS data: retention time(min)/ M + H |
|---|---|---|---|---|
| 226 | H | Me | HN⌒CO₂H | 2.99/491.3 |
| 227 | H | Me | HN⌒⌒CO₂H | 3.00/519.3 |
| 228 | 5-Br | H | HN-tetrazole | 2.12/565, 567 |
| 229 | 5-Br | H | HN⌒CO₂H | 2.05/569, 571 |
| 230 | 6-F₂CHCH₂O | H | HN-tetrazole | 2.15/567.2 |

TABLE 10-continued
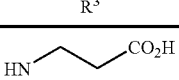
| Example | R¹ | R² | R³ | LCMS data: retention time(min)/ M + H |
|---|---|---|---|---|
| 231 | 6-F₂CHCH₂O | H | 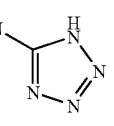 | 2.10/571.3 |
| 232 | 6-ᶜHexylO | H | 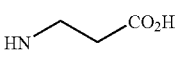 | 2.52/585.3 |
| 233 | 6-ᶜHexylO | H | 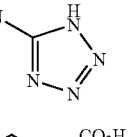 | 2.47/589.3 |
| 234 | 6-ᶜHexylCH₂O | H | 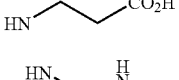 | 2.70/599.3 |
| 235 | 6-ᶜHexylCH₂O | H |  | 2.66/603.3 |
| 236 | 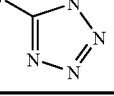 | H | 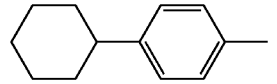 | 1.65/600.3 |
TABLE 11
| Example | R¹ | R² | LCMS data: retention time(min)/ M + H |
|---|---|---|---|
| 237 | 5-OMe | Ph₂CH— | 1.67/515.2 |
| 238 | 5-OᶜPent | (cyclohexyl-p-tolyl) | 2.49/591.3 |
TABLE 11-continued
| Example | R¹ | R² | LCMS data: retention time(min)/ M + H |
|---|---|---|---|
| 239 | 5-OMe | (3-chloro-ethylphenyl) | 1.55/503.1 |

TABLE 11-continued

General structure: benzimidazole (with R¹) bearing N-Me, connected via N(R²)CH₂ to a para-substituted benzamide linked to N-H tetrazole.

| Example | R¹ | R² | LCMS data: retention time(min)/ M + H |
|---|---|---|---|
| 240 | H | 4-methyl-1-(trifluoromethyl)cyclohexyl | 2.65/499.2 |
| 241 | H | 4-BrPh | 1.48/505.1 |
| 242 | H | 4-ᵗBuPh | 1.81/481.2 |
| 243 | 5-MeO | 3,5-diClPh | 1.72/523.1 |
| 245 | 5-OMe | 4-Cl-phenethyl | 1.58/503.1 |
| 246 | 5-OMe | 2-Cl-phenethyl | 1.50/503.1 |
| 247 | H | 4-phenylcyclohexyl-methyl | 2.87/507.3 |
| 248 | H | 6-fluoro-1,2,3,4-tetrahydronaphthalen-2-yl-methyl | 2.72/497.2 |
| 249 | H | 4-biphenyl-methyl | 1.75/501.3 |
| 250 | H | 4-ⁱPrPh | 1.70/467.3 |
| 251 | H | PhCH₂CH₂ | 1.39/453.2 |
| 252 | H | PhCH₂CH₂CH₂ | 1.55/467.2 |
| 253 | H | PhCH₂CH₂CH₂CH₂ | 1.68/481.2 |
| 254 | H | 4-ClPhCH₂CH₂ | 1.57/487.1 |
| 255 | 5-OPr | 3,5-diClPh | 2.02/551.2 |
| 256 | 5-OᶜPent | 3,5-diClPh | 2.17/577.2 |
| 257 | H | 6-bromo-1,2,3,4-tetrahydronaphthalen-2-yl-methyl | 2.89/559.1 |
| 258 | 5-CF₃O | 4-CF₃OPh | 2.22/593.1 |
| 259 | 5-CF₃ | 4-CF₃OPh | 2.26/577.2 |
| 260 | 5-Cl | 4-CF₃OPh | 1.97/543.1 |
| 261 | 5-MeO | 4-CF₃OPh | 1.68/539.2 |
| 262 | 5-PrO | 4-CF₃OPh | 1.94/567.3 |
| 263 | 5-ᶜPentO | 4-CF₃OPh | 2.08/593.3 |

TABLE 12

General structure: benzimidazole (with R¹) bearing N-Me, connected via N(R²)CH₂ to a para-substituted benzamide linked to NHCH₂CH₂CO₂H.

| Example | R¹ | R² | LCMS data: retention time(min)/ M + H |
|---|---|---|---|
| 264 | 5-OᶜPent | 4-cyclohexylphenyl-methyl | 2.43/595.3 |
| 265 | 5-OPr | 4-cyclohexylphenyl-methyl | 2.30/569.3 |
| 266 | H | adamantyl-methyl | 1.66/487.3 |
| 267 | H | 4-ᵗBuPh | 1.75/485.2 |
| 268 | H | 4-phenylcyclohexyl-methyl | 2.82/511.3 |
| 269 | H | 6-fluoro-1,2,3,4-tetrahydronaphthalen-2-yl-methyl | 2.66/501.2 |

TABLE 12-continued

[Structure with R¹ on benzimidazole, N-Me, N-R², and benzamide-NHCH₂CH₂CO₂H]

| Example | R¹ | R² | LCMS data: retention time(min)/ M + H |
|---|---|---|---|
| 270 | H | 4-PhPh (biphenyl) | 1.70/505.3 |
| 271 | H | 4-$^i$PrPh | 1.65/471.3 |
| 272 | H | 4-ClPhCH₂CH₂ | 1.35/457.2 |
| 273 | H | (bromotetrahydronaphthyl) | 2.89/559.1 |
| 274 | 5-MeO | 4-CF₃OPh | 1.62/543.2 |

EXAMPLE 275/276

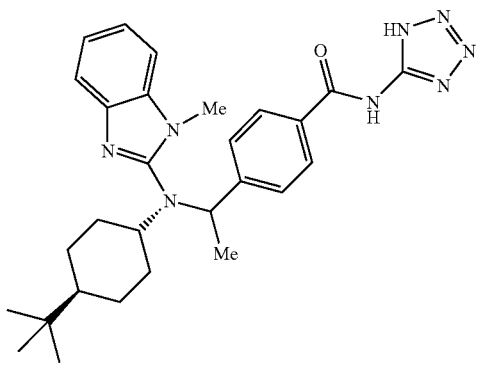

Step A. Ethyl 4-{1-[(trans-4-tert-butylcyclohexyl)amino]ethyl}benzoate

A mixture of ethyl 4-acetylbenzoate (3.00 g, 15.6 mmol), titanium (IV) isopropoxide (9.30 mL, 31.2 mmol), 4-tert-butylcyclohexyl amine (4.85 g, 31.2 mmol) in absolute ethanol (100 mL) was stirred under nitrogen at room temperature for 10 h. Sodium borohydride (0.88 g, 23.4 mmol) was then added and the resulting mixture was stirred for an additional 8 h at room temperature. The reaction was quenched by pouring into aqueous ammonia (2N, 225 mL). The resulting inorganic precipitate was filtered off and washed with dichloromethane (100 mL). The organic layer was separated and the remaining aqueous layer was extracted once with dichloromethane (100 mL). The combined organic extracts were dried over Na₂SO₄, filtered and concentrated. Chromatography (20% EtOAc in Hexane) afforded ethyl 4-{1-[(trans-4-tert-butylcyclohexyl)amino]ethyl}benzoate. HPLC/MS: m/z=332.3 (M+1), $R_t$=2.74 min. ¹HNMR (500 MHz, CDCl₃): δ 8.01 (2H, d, J=8.1 Hz), 7.38 (2H, d, J=8.0 Hz), 4.37 (2H, q, J=7.1 Hz), 4.02 (1H, q, J=6.6 Hz), 2.18-2.06 (2H, m), 1.77-1.67 (4H, m), 1.39 (3H, t, J=7.1 Hz), 1.32 (3H, d, J=6.5 Hz), 1.22 (1H, br s), 1.09-0.85 (4H, m), 0.79 (9H, s).

Step B. Ethyl 4-{1-[(trans-4-tert-butylcyclohexyl)(1-methyl-1H-benzimidazol-2-yl)amino]ethyl}benzoate To a 0° C. solution of ethyl 4-{1-[(trans-4-tert-butylcyclohexyl)amino]ethyl}benzoate (0.55 g, 1.66 mmol) and DIEA (0.35 mL, 1.99 mmol) in dry dichloromethane (15 mL) was slowly added thiophosgene (0.13 mL, 1.66 mmol). After stirring at 0° C. for 10 min and then at room temperature for 45 min, a solution of N-methylbenzene-1,2-diamine (0.22 g, 1.83 mmol) and DIEA (0.35 mL, 1.99 mmol) in dry dichloromethane (5 mL) was added. The reaction mixture was stirred for 1 h at ambient temperature and then diluted with dichloromethane (20 mL) and poured into aqueous HCl (1N, 20 mL). The organic layer was separated and washed with aqueous HCl (1N, 20 mL), saturated aqueous NaHCO₃ (20 mL), brine (20 mL), dried over Na₂SO₄ and then concentrated to dryness. The residue was dissolved in dichloromethane (20 mL) and mercury (II) trifluoroacetate (0.80 g, 1.86 mmol) was added. The reaction mixture was stirred for 30 min at room temperature and then filtered through Celite. The organic solution was washed with saturated NaHCO₃ (20 mL), dried over Na₂SO₄ and concentrated. Chromatography (15% EtOAc in Hexane) afforded ethyl 4-{1-[(trans-4-tert-butylcyclohexyl)(1-methyl-1H-benzimidazol-2-yl)amino]ethyl}benzoate. HPLC/MS: m/z=462.4 (M+1), $R_t$=3.46 min. ¹H NMR (500 MHz, CDCl₃): ☐ 8.03 (2H, d, J=8.2 Hz), 7.78 (1H, m), 7.52 (2H, d, J=8.2 Hz), 7.28 (3H, m), 4.80 (1H, q, J=6.5 Hz), 4.39 (2H, q, J=7.5 Hz), 3.72 (3H, s), 2.86 (1H, m), 2.14 (1H, m), 1.94 (1H, m), 1.72-1.64 (2H, m), 1.48 (1H, m), 1.41 (3H, t, J=7.5 Hz), 1.17 (3H, d, J=6.5 Hz), 0.95-0.75 (4H, m), 0.73 (9H, s).

Step C. 4-{1-[(trans-4-tert-Butylcyclohexyl)(1-methyl-1H-benzimidazol-2-yl)amino]ethyl}-N-1H-tetrazol-5-ylbenzamide, Isomer A and B Ethyl 4-{1-[(trans-4-tert-butylcyclohexyl)(1-methyl-1H-benzimidazol-2-yl)amino]ethyl}benzoate (0.22 g, 0.48 mmol) was dissolved in EtOH/n-Heptane (1:1, 9 mL) and eluted with 5% isopropanol in n-Heptane on ChiralPak AD column. The fast moving component was collected as isomer A and the slow moving component as isomer B.

Ethyl 4-{1-[(trans-4-tert-butylcyclohexyl)(1-methyl-1H-benzimidazol-2-yl)amino]ethyl}benzoate, isomer A (0.10 g, 0.22 mmol) was dissolved in THF/MeOH (1:1, 6 mL) and aq. LiOH (1.0 M, 3 mL) was added. After stirred at room temperature for 16 h, the reaction was neutralized with aqueous HCl (1N, 3.5 mL) until white precipitate started to appear. The resulting mixture was poured into brine (10 mL) and extracted with EtOAc (3×10 mL). The organic extracts were combined, dried over Na₂SO₄ and then concentrated. The residue was dissolved in dry DMF (6 mL) and divided into 3 portions for amide coupling reaction under standard conditions (EDC/HOBt/DIEA in DMF) with 5-amino tetrazole, β-alanine methyl ester and β-hydroxyl β-alanine methyl ester, respectively. For the tetrazole coupling, reaction mixture was loaded directly on HPLC (Xterra C₁₈ column from Waters) and eluted with CH₃CN in H₂O containing 0.1% TFA (20% to 95% over 12 min). Product was freeze-dried from dioxane as a white powder. For coupling reactions with, β-alanine methyl ester and β-hydroxyl β-alanine methyl ester, products were purified on silica gel (35% to 45% EtOAc in Hexane). Methyl ester was subsequently removed with 1.0 M aq. LiOH in THF/MeOH. The resulting carboxylic acids were obtained without further purification.

Isomer A. HPLC/MS: m/z=501.4 (M+1), R_t=3.01 min. ¹H NMR (DMSO-d₆): δ 12.40 (1H, s), 8.07 (2H, d, J=8.3 Hz), 7.70-7.67 (2H, m), 7.66 (2H, d, J=8.5 Hz), 7.47-7.42 (2H, m), 4.90 (1H, q, J=6.5 Hz), 3.14 (1H, t, J=11.5 Hz), 2.53 (3H, s), 2.02 (2H, m), 1.68 (2H, m), 1.35 (3H, d, J=6.4 Hz), 1.32-1.24 (1H, m), 1.13-1.06 (1H, m), 0.96-0.78 (3H, m), 0.73 (9H, s).

Isomer B. HPLC/MS: m/z=501.4 (M+1), R_t=3.02 min. ¹H NMR (DMSO-d₆): δ 12.40 (1H, s), 8.07 (2H, d, J=8.3 Hz), 7.70-7.67 (2H, m), 7.66 (2H, d, J=8.5 Hz), 7.47-7.42 (2H, m), 4.90 (1H, q, J=6.5 Hz), 3.14 (1H, t, J=11.5 Hz), 2.53 (3H, s), 2.02 (2H, m), 1.68 (2H, m), 1.35 (3H, d, J=6.4 Hz), 1.32-1.24 (1H, m), 1.13-1.06 (1H, m), 0.96-0.78 (3H, m), 0.73 (9H, s).

EXAMPLE 277/278

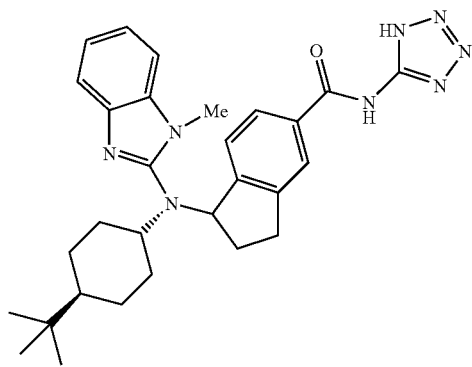

Step A. (5-Bromo-2,3-dihydro-1H-inden-1-yl)(trans-4-tert-butylcyclohexyl)amine A mixture of 5-bromoindan-1-one (6.33 g, 30.0 mmol), titanium (IV) isopropoxide (17.8 mL, 60.0 mmol), 4-tert-butylcyclohexyl amine (9.32 g, 60.0 mmol) in absolute ethanol (200 mL) was stirred under nitrogen at room temperature for 12 h. Sodium borohydride (1.70 g, 45.0 mmol) was then added and the resulting mixture was stirred for an additional 8 h at room temperature. The reaction was quenched by pouring into aqueous ammonia (2N, 300 mL). The resulting inorganic precipitate was filtered off and washed with dichloromethane (150 mL). The organic layer was separated and the remaining aqueous layer was extracted once with dichloromethane (150 mL). The combined organic extracts were dried over Na₂SO₄, filtered and concentrated. Chromatography (10% to 20% EtOAc in Hexane) afforded (5-Bromo-2,3-dihydro-1H-inden-1-yl)(trans-4-tert-butylcyclohexyl)amine and the corresponding cis product (less polar). HPLC/MS: m/z=350.1 (M+1), R_t=3.01 min.

Step B. Methyl 1-[(trans-4-tert-butylcyclohexyl)amino]indane-5-carboxylate (5-Bromo-2,3-dihydro-1H-inden-1-yl)(trans-4-tert-butylcyclohexyl)amine (1.20 g, 3.42 mmol) was dried azeotropically from dry THF in toluene (3×) and kept under high vacuum for 2 h before use. It was then dissolved in anhydrous THF (20 mL) and cooled to −78° C. n-Butyl lithium (1.6 M solution in Hexane, 8.40 mL, 13.68 mmol) was added over 15 min. After stirring at −78° C. for 30 min, excess dry ice cubes were then added. The reaction mixture was allowed to warm up slowly and then quenched at −20° C. with saturated aqueous NH₄Cl (20 mL). Extractions with EtOAc (3×15 mL), drying (Na₂SO₄), filtration and removal of solvent gave the crude carboxylic acid. The crude carboxylic acid was dissolved in MeOH/DCM (1:2, 10 mL) and then (trimethylsilyl)diazomethane (2.0 M solution in Hexane) was added until gas bubbling ceased and the yellow color sustained. Concentration and chromatography (35% EtOAc in Hexane) afforded methyl 1-[(trans-4-tert-butylcyclohexyl)amino]indane-5-carboxylate. HPLC/MS: m/z=330.3 (M+1), R_t=2.85 min.

Step C. Methyl 1-[(trans-4-tert-butylcyclohexyl)(1-methyl-1H-benzimidazol-2-yl)amino]indane-5-carboxylate To a 0° C. solution of methyl 1-[(trans-4-tert-butylcyclohexyl)amino]indane-5-carboxylate (0.43 g, 1.30 mmol) and DIEA (0.27 mL, 1.56 mmol) in dry dichloromethane (20 mL) was added thiophosgene (0.11 mL, 1.36 mmol) slowly. After stirring at 0° C. for 10 min and then at room temperature for 45 min, a solution of N-methylbenzene-1,2-diamine (0.38 g, 3.12 mmol) and DIEA (0.53 mL, 3.12 mmol) in dry dichloromethane (5 mL) was added. The reaction mixture was stirred for 1 h at room temperature, then diluted with dichloromethane (30 mL) and poured into aqueous HCl (1N, 30 mL). The organic layer was separated and washed with aqueous HCl (1N, 30 mL), saturated aqueous NaHCO₃ (30 mL), brine (30 mL), dried over Na₂SO₄ and then concentrated to dryness. The residue was dissolved in dichloromethane (30 mL) and mercury (II) trifluoroacetate (0.61 g, 1.43 mmol) was added. The reaction mixture was stirred for 30 min at room temperature and then filtered through Celite. The organic solution was washed once with saturated NaHCO₃ (30 mL), dried over Na₂SO₄ and concentrated. Chromatography (15% EtOAc in Hexane) afforded methyl 1-[(trans-4-tert-butylcyclohexyl)(1-methyl-1H-benzimidazol-2-yl)amino]indane-5-carboxylate. HPLC/MS: m/z=460.3 (M+1), R_t=3.46 min. ¹H NMR (CDCl₃): δ 7.85 (1H, s), 7.78 (1H, d, J=8.0 Hz), 7.71 (1H, m), 7.27 (1H, d, J=8.5 Hz), 7.25-7.18 (3H, m), 5.04 (1H, dd, J=7.5, 5.0 Hz), 3.90 (3H, s), 3.48 (3H, s), 3.24 (1H, m), 3.10 (1H, m), 2.83 (1H, m), 2.66 (1H, m), 2.39 (1H, m), 2.21 (1H, m), 1.94 (1H, m), 1.85-1.75 (2H, m), 1.50 (1H, m), 1.36 (1H, m), 1.10-0.94 (2H, m), 0.84 (9H, s).

Step D. 1-[(trans-4-tert-Butylcyclohexyl)(1-methyl-1H-benzimidazol-2-yl)amino]-N-1H-tetrazol-5-ylindane-5-carboxamide Methyl 1-[(trans-4-tert-butylcyclohexyl)(1-methyl-1H-benzimidazol-2-yl)amino] indane-5-carboxylate (0.43 g, 0.48 mmol) was dissolved in EtOH/n-Heptane (1:1, 9 mL) and eluted with 5% isopropanol in n-Heptane on ChiralPak AD column. The fast moving component was collected as isomer A and the slow moving component as isomer B.

Methyl 1-[(trans-4-tert-butylcyclohexyl)(1-methyl-1H-benzimidazol-2-yl)amino]indane-5-carboxylate, isomer A (0.10 g, 0.22 mmol) was dissolved in THF/MeOH (1:1, 6 mL) and aq. LiOH (1.0 M, 3 mL) was added. After stirred at room temperature for 16 h, the reaction was neutralized with aqueous HCl (1N, 3.5 mL) until white precipitate started to appear.

The resulting mixture was poured into brine (10 mL) and extracted with EtOAc (3×10 mL). The organic extracts were combined, dried over $Na_2SO_4$ and then concentrated. The residue was dissolved in dry DMF (6 mL) and divided into 3 portions for amide coupling reaction under standard conditions (EDC/HOBt/DIEA in DMF) with 5-amino tetrazole, β-alanine methyl ester and β-hydroxyl β-alanine methyl ester, respectively. For the tetrazole coupling, reaction mixture was loaded directly on HPLC (Xterra $C_{18}$ column from Waters) and eluted with $CH_3CN$ in $H_2O$ containing 0.1% TFA (5% to 70% over 12 min). Product was freeze-dried from dioxane as a white powder. For coupling reactions with β-alanine methyl ester and β-hydroxyl β-alanine methyl ester, products were purified on silica gel (50% to 60% EtOAc in Hexane). Methyl ester was subsequently removed with 1.0 M aq. LiOH in THF/MeOH. The resulting carboxylic acids were obtained without further purification.

Isomer A: HPLC/MS: m/z=513.3 (M+1), $R_t$=3.09 min. $^1$H NMR (DMSO-$d_6$): δ 10.97 (1H, br s), 7.92 (1H, s), 7.78 (H, d, J=7.7 Hz), 7.60 (1H, d, J=8.0 Hz), 7.48 (1H, d, J=8.0 Hz), 7.42 (1H, d, J=8.0 Hz), 7.40-7.33 (2H, m), 5.35 (1H, t, J=7.8 Hz), 3.72 (3H, s), 3.74-3.52 (2H, m), 3.24-3.18 (1H, m), 3.01-2.94 (1H, m), 2.64-2.58 (2H, m), 2.09 (2H, m), 1.87 (2H, m), 1.68 (2H, m), 1.65 (2H, m), 1.05 (1H, m), 0.87 (9H, s).

Isomer B: HPLC/MS: m/z=513.3 (M+1), $R_t$=3.10 min. $^1$H NMR (DMSO-$d_6$): δ 10.97 (1H, br s), 7.92 (1H, s), 7.78 (H, d, J=7.7 Hz), 7.60 (1H, d, J=8.0 Hz), 7.48 (1H, d, J=8.0 Hz), 7.42 (1H, d, J=8.0 Hz), 7.40-7.33 (2H, m), 5.35 (1H, t, J=7.8 Hz), 3.72 (3H, s), 3.74-3.52 (2H, m), 3.24-3.18 (1H, m), 3.01-2.94 (1H, m), 2.64-2.58 (2H, m), 2.09 (2H, m), 1.87 (2H, m), 1.68 (2H, m), 1.65 (2H, m), 1.05 (1H, m), 0.87 (9H, s).

Following the procedures outlined above the compounds listed in Tables 13-14 were prepared.

TABLE 13

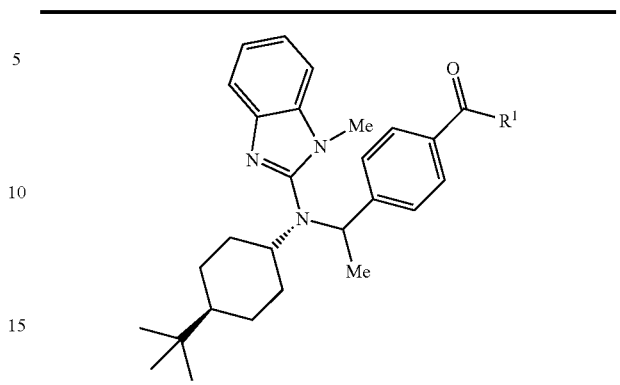

| Example | isomer | $R^2$ | LCMS data: retention time(min)/M + H |
|---|---|---|---|
| 279 | A | HN~~CO2H | HPLC/MS: m/z = 505.3 (M + 1), $R_t$ = 3.06 min. |
| 280 | B | HN~~CO2H | HPLC/MS: m/z = 505.3 (M + 1), $R_t$ = 3.06 min. |
| 281 | A | HN~~CO2H, OH | HPLC/MS: m/z = 521.3 (M + 1), $R_t$ = 2.98 min. |

TABLE 13-continued

| Example | isomer | $R^2$ | LCMS data: retention time(min)/M + H |
|---|---|---|---|
| 282 | B | HN~~CO2H, OH | HPLC/MS: m/z = 521.3 (M + 1), $R_t$ = 2.98 min. |

TABLE 14

| Example | isomer | $R^2$ | LCMS data: retention time (min)/M + H |
|---|---|---|---|
| 283 | A | HN~~CO2H | HPLC/MS: m/z = 517.3 (M + 1), $R_t$ = 3.04 min |
| 284 | B | HN~~CO2H | HPLC/MS: m/z = 517.3 (M + 1), $R_t$ = 3.04 min. |
| 285 | A | HN~~CO2H, OH | HPLC/MS: m/z = 533.3 (M + 1), $R_t$ = 2.93 min. |
| 286 | B | HN~~CO2H, OH | HPLC/MS: m/z = 533.3 (M + 1), $R_t$ = 2.93 min. |

EXAMPLE 287

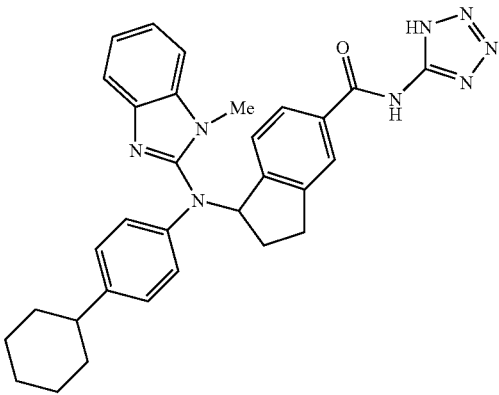

Step A. Butyl 1-[(4-cyclohexylphenyl)amino]indane-5-carboxylate

To a solution of butyl 1-oxoindane-5-carboxylate (2.0 g, 8.60 mmol) and 4-cyclohexylaniline (2.28 g, 20.64 mmol) in 30 mL of anhydrous MeOH was added decaborane $B_{10}H_{14}$ (0.32 g, 2.6 mmol) at room temperature under nitrogen. The resulting solution was stirred at room temperature for 1648 h. Product butyl 1-[(4-cyclohexylphenyl)amino]indane-5-carboxylate was collected by filtration as a white solid. HPLC/MS: m/z=392.3 (M+1), $R_t$=4.97 min. $^1$H NMR (CDCl$_3$): δ 7.80 (1H, s), 7.97 (1H, d, J=8.0 Hz), 7.48 (1H, d, J=8.0 Hz), 7.14 (2H, d, J=8.5 Hz), 6.74 (2H, d, J=8.5 Hz), 5.07 (1H, t, J=7.1 Hz), 4.39 (2H, t, J=6.7 Hz), 3.92 (1H, br s), 3.10 (1H, m), 2.97 (1H, m), 2.69 (1H, m), 2.49 (1H, m), 2.02-1.80 (8H, m), 1.60-1.31 (7H, m), 1.08 (3H, t, J=7.3 Hz).

Step B. Butyl 1-[(4-cyclohexylphenyl)(1-methyl-1H-benzimidazol-2-yl)amino]indane-5-carboxylate To a 0° C. solution of butyl 1-[(4-cyclohexylphenyl)amino]indane-5-carboxylate (0.50 g, 1.27 mmol) and DIEA (0.33 mL, 1.90 mmol) in dry dichloromethane (15 mL) was added thiophosgene (0.10 mL, 1.34 mmol) slowly. After stirring at 0° C. for 10 min and then at room temperature for 1 h, a solution of N-methylbenzene-1,2-diamine (0.23 g, 1.90 mmol) and DIEA (0.33 mL, 1.90 mmol) in dry dichloromethane (5 mL) was added. The reaction mixture was stirred for 1 h at room temperature and then diluted with dichloromethane (30 mL) and poured into aqueous HCl (1N, 30 mL). The organic layer was separated and washed with aqueous HCl (1N, 30 mL), saturated aqueous NaHCO$_3$ (30 mL), brine (30 mL), dried over Na$_2$SO$_4$ and then concentrated to dryness. The residue was dissolved in dichloromethane (30 mL) and excess of mercury (II) trifluoroacetate was added. The reaction mixture was stirred for 30 min at ambient temperature and then filtered through Celite. The organic solution was washed with saturated NaHCO$_3$ (30 mL), dried over Na$_2$SO$_4$ and concentrated. Chromatography (8% to 15% EtOAc in Hexane) afforded butyl 1-[(4-cyclohexylphenyl)(1-methyl-1H-benzimidazol-2-yl)amino]indane-5-carboxylate. HPLC/MS: m/z=552.4 (M+1), $R_t$=2.58 min. $^1$H NMR (CDCl$_3$): δ 7.96 (1H, d, J=7.8 Hz), 7.91 (1H, s), 7.70 (1H, d, J=7.5 Hz), 7.55 (1H, d, J=7.5 Hz), 7.27-7.20 (2H, m), 7.18 (1H, d, J=7.5 Hz), 7.01 (2H, d, J=8.5 Hz), 6.67 (2H, d, J=8.5 Hz), 6.20 (1H, t, J=7.5 Hz), 4.37 (1H, t, J=6.5 Hz), 3.21 (3H, s), 2.91-2.85 (1H, m), 2.77-2.64 (2H, m), 2.46-2.34 (2H, m), 1.86-1.75 (8H, m), 1.54 (2H, m), 1.41-1.24 (6H, m), 1.04 (3H, t, J=7.5 Hz).

Step C. 1-[(4-Cyclohexylphenyl)(1-methyl-1H-benzimidazol-2-yl)amino]-N-1H-tetrazol-5-ylindane-5-carboxamide, Isomer B Butyl 1-[(4-cyclohexylphenyl)(1-methyl-1H-benzimidazol-2-yl)amino]indane-5-carboxylate (0.10 g, 0.18 mmol) was dissolved in EtOH/n-Heptane (1:1, 4 mL) and eluted with 10% isopropanol in n-Heptane on ChiralPak AD column. The fast moving component was collected as isomer A and the slow moving component as isomer B.

Butyl 1-[(4-cyclohexylphenyl)(1-methyl-1H-benzimidazol-2-yl)amino] indane-5-carboxylate, isomer B (44.0 mg, 0.07 mmol) was dissolved in THF/MeOH (1:1, 6 mL) and aq. LiOH (1.0 M, 3 mL) was added. After stirred at room temperature for 16 h, the reaction was neutralized with aqueous HCl (1N, 3.5 mL) until white precipitate started to appear. The resulting mixture was poured into brine (10 mL) and extracted with EtOAc (3×10 mL). The organic extracts were combined, dried over Na$_2$SO$_4$ and then concentrated. The residue was dissolved in dry DMF (2 mL) and coupled with 5-amino tetrazole. Product was purified on HPLC (Xterra C$_{18}$ column from Waters) with CH$_3$CN in H$_2$O containing 0.1% TFA (5% to 80% over 12 min) and freeze-dried from dioxane to yield 1-[(4-cyclohexylphenyl)(1-methyl-1H-benzimidazol-2-yl)amino]-N-1H-tetrazol-5-ylindane-5-carboxamide, isomer B. HPLC/MS: m/z=533.4 (M+1), $R_t$=2.05 min. $^1$H NMR (DMSO d6): δ 12.38 (1H, s), 7.97 (1H, d, J=8.0 Hz), 7.96 (1H, s), 7.77 (1H, d, J=7.5 Hz), 7.56 (1H, dd, J=6.0, 3.5 Hz), 7.51 (1H, m), 7.31 (2H, m), 7.17 (2H, d, J=8.5 Hz), 6.92 (2H, d, J=8.0 Hz), 5.98 (1H, t, J=7.5 Hz), 3.17 (3H, s), 2.91-2.84 (1H, m), 2.72 (1H, m), 2.61 (1H, m), 2.46 (1H, m), 2.33 (1H, m), 1.77-1.18 (11H, m).

EXAMPLE 288

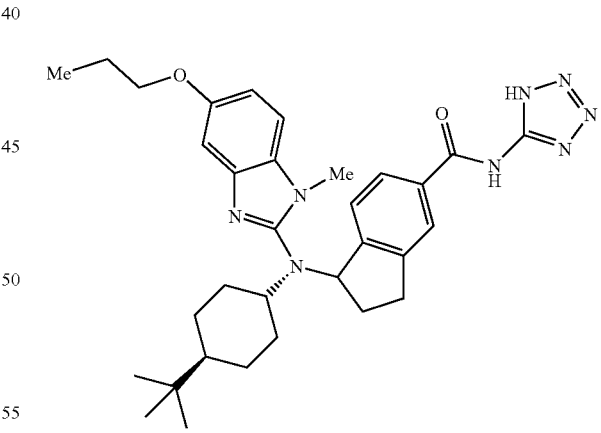

Step A. Butyl 1-[(trans-4-tert-butylcyclohexyl)(5-methoxy-1-methyl-1H-benzimidazol-2-yl)amino]indane-5-carboxylate To a 0° C. solution of butyl 1-[(trans-4-tert-butylcyclohexyl)amino]indane-5-carboxylate (0.93 g, 2.5 mmol) and DIEA (0.52 mL, 3.00 mmol) in anhydrous dichloromethane (20 mL) was added thiophosgene (0.20 mL, 2.60 mmol) slowly. After stirring at 0° C. for 30 min, a solution of 4-methoxy-N$^1$-methylbenzene-1,2-diamine (0.46 g, 3.00 mmol) and DIEA (0.52 mL, 3.00 mmol) in dry dichloromethane (5 mL) was added. The reaction mixture was stirred for 30 min at room temperature and then diluted with dichloromethane (30 mL) and poured into saturated aqueous NaHCO$_3$ (30 mL). The organic layer was separated, dried over Na$_2$SO$_4$ and then concentrated to dryness. Chromatography afforded 0.94 g (66%) of a mixture of two thiourea intermediates. The mixture of two thioureas was dissolved in dichloromethane (50 mL) and mercury (II) trifluoroacetate (0.78 g, 1.82 mmol) was added. The reaction mixture was stirred for 1 h at room temperature and then filtered through Celite. The filtrate was washed once with saturated NaHCO$_3$ (30 mL), dried over Na$_2$SO$_4$ and concentrated. Chromatography (15% to 20% EtOAc in Hexane) afforded butyl 1-[(trans-4-tert-butylcyclohexyl)(5-methoxy-1-methyl-1H-benzimidazol-2-yl)amino] indane-5-carboxylate. HPLC/MS: m/z=532.4 (M+1), R$_t$=3.92 min.

Step B. Butyl 1-[(trans-4-tert-butylcyclohexyl)(5-hydroxy-1-methyl-1H-benzimidazol-2-yl)amino]indane-5-carboxylate To a solution of butyl 1-[(trans-4-tert-butylcyclohexyl)(5-methoxy-1-methyl-1H-benzimidazol-2-yl)amino]indane-5-carboxylate (0.40 g, 0.75 mmol) in 20 mL of anhydrous dichloromethane at −78° C. was slowly added BBr$_3$ (1.0 M solution in CH$_2$Cl$_2$, 3.8 mL, 3.8 mmol) over 10 min. The reaction mixture was stirred at −78° C. for 30 min and then the cold bath was removed. The reaction was quenched after 20 min with saturated aqueous NaHCO$_3$ (20 mL) and extracted with EtOAc (3×15 mL). The organic layers were combined, dried over Na$_2$SO$_4$ and concentrated. Chromatography afforded butyl 1-[(trans-4-tert-butylcyclohexyl)(5-hydroxy-1-methyl-1H-benzimidazol-2-yl)amino]indane-5-carboxylate. HPLC/MS: m/z=518.4 (M+1), R$_t$=2.45 min.

Step C. Butyl 1-[(trans-4-tert-butylcyclohexyl)(1-methyl-5-propoxy-1H-benzimidazol-2-yl)amino]indane-5-carboxylate To a solution of butyl 1-[(trans-4-tert-butylcyclohexyl)(5-hydroxy-1-methyl-1H-benzimidazol-2-yl)amino]indane-5-carboxylate (49.0 mg, 0.095 mmol) in dry dichloromethane was added 1-propanol (18.0 □L, 0.24 mmol), diisopropyl azodicarboxylate (37.0 µL, 0.19 mmol) and Ph$_3$P (50.0 mg, 0.19 mmol). After stirring at room temperature for 2 h, solvent was removed. Chromatography (15% EtOAc in Hexane) afforded butyl 1-[(trans-4-tert-butylcyclohexyl)(1-methyl-5-propoxy-1H-benzimidazol-2-yl)amino]indane-5-carboxylate. HPLC/MS: m/z=560.5 (M+1), R$_t$=2.43 min.

Step D. 1-[(trans-4-tert-Butylcyclohexyl)(1-methyl-5-propoxy-1H-benzimidazol-2-yl)amino]-N-1H-tetrazol-5-ylindane-5-carboxamide Butyl 1-[(trans-4-tert-butylcyclohexyl)(1-methyl-5-propoxy-1H-benzimidazol-2-yl)amino]indane-5-carboxylate (36.0 mg, 0.06 mmol) was dissolved in THF/MeOH (1:1, 6 mL) and aq. LiOH (1.0 M, 3 mL) was added. After stirred at room temperature for 16 h, the reaction was neutralized with aqueous HCl (1N, 3.5 mL) until white precipitate started to appear. The resulting mixture was poured into brine (10 mL) and extracted with EtOAc (3×10 mL). The organic extracts were combined, dried over Na$_2$SO$_4$ and then concentrated. The residue was dissolved in dry DMF (2 mL) and coupled with 5-amino tetrazole (EDC/HOBt/DIEA). Product was purified on HPLC (Xterra C$_{18}$ column from Waters) with CH$_3$CN in H$_2$O containing 0.1% TFA (20% to 95% over 12 min) and freeze-dried from dioxane to yield 1-[(trans-4-tert-Butylcyclohexyl)(1-methyl-5-propoxy-1H-benzimidazol-2-yl)amino]-N-1H-tetrazol-5-ylindane-5-carboxamide.
HPLC/MS: m/z=571.5 (M+1), R$_t$=2.16 min. $^1$H NMR (DMSO-d$_6$): δ 12.34 (1H, s), 7.98 (1H, s), 7.86 (1H, d, J=8.5 Hz), 7.52 (1H, m), 7.42 (1H, d, J=8.0 Hz), 7.03 (1H, d, J=2.0 Hz), 6.98 (1H, d, J=7.5 Hz), 5.30 (1H, m), 3.67-3.45 (2H, m), 3.95 (2H, t, J=7.0 Hz), 3.71 (3H, s), 3.36 (1H, m), 3.16-3.11 (1H, m), 2.95-2.88 (1H, m), 2.56 (2H, m), 2.00 (2H, m), 1.79-1.70 (4H, m), 1.66-1.51 (2H, m), 1.12-1.05 (2H, m), 0.98 (3H, t, J=7.5 Hz), 0.82 (9H, s).

Biological Assays

The ability of the compounds of the present invention to inhibit the binding of glucagon and their utility in treating or preventing type 2 diabetes mellitus and the related conditions can be demonstrated by the following in vitro assays.

Glucagon Receptor Binding Assay

A stable CHO (Chinese hamster ovary) cell line expressing cloned human glucagon receptor was maintained as described (Chicchi et al. *J Biol Chem* 272, 7765-9(1997); Cascieri et al. *J Biol Chem* 274, 8694-7(1999)). To determine antagonistic binding affinity of compounds 0.002 mg of cell membranes from these cells were incubated with $^{125}$I-Glucagon (New England Nuclear, Mass.) in a buffer containing 50 mM Tris-HCl (pH 7.5), 5 mM MgCl$_2$, 2 mM EDTA, 12% Glycerol, and 0.200 mg WGA coated PVT SPA beads (Amersham), +/− compounds or 0.001 mM unlabeled glucagon. After 3 hours incubation at room temperature, the radioactivity bound to the cell membranes was determined in a radioactive emission detection counter (Wallac-Microbeta). Data were analyzed using the software program Prism® from GraphPad. The IC$_{50}$ were calculated using non-linear regression analysis assuming single site competition.

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was setup as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in presence of compounds or DMSO controls for 30 minutes, and then stimulated with glucagon (250 pM) for an additional 30 minutes. The cell stimulation was stopped by addition of equal amount of a detection buffer containing lysis buffer as well as $^{125}$I-labeled cAMP tracer (NEN). After 3 hours of incubation at room temperature the bound radioactivity was determined in a liquid scintillation counter (TopCount-Packard Instruments). Basal activity (100% inhibition) was determined using the DMSO control while 0% inhibition was defined at the amount of pmol cAMP produced by 250 pM glucagon.

Certain embodiments of the invention has been described in detail; however, numerous other embodiments are contemplated as falling within the invention. Thus, the claims are not limited to the specific embodiments described herein. All patents, patent applications and publications of any kind that are cited herein are hereby incorporated by reference in their entirety.

What is claimed is:

1. A compound represented by formula I:

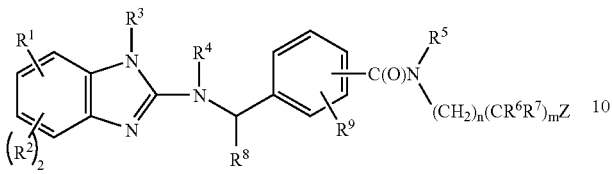

or a pharmaceutically acceptable salt or solvate thereof, wherein:

$R^1$ represents H or is independently selected from the group consisting of:
- a) OH, halo, $CO_2R^a$, $C(O)NR^bR^c$, $NR^bR^c$, CN or $S(O)_pR^d$;
- b) $C_{1-10}$alkyl, $C_{2-10}$alkenyl, $C_{2-10}$alkynyl, $OC_{1-10}$alkyl, $OC_{3-10}$alkenyl and $OC_{3-10}$alkynyl, said groups being optionally substituted with: (1) 1-5 halo groups up to a perhaloalkyl group; (2) 1 oxo group; (3) 1-2 OH groups; (4) 1-2 $C_{1-10}$alkoxy groups, each optionally substituted with: up to five halo or a perhaloalkoxy, 1 OH or $CO_2R^a$ group; (5) 1 $CO_2R^a$ or $S(O)_pR^d$; (6) 1-2 Aryl, Hetcy or HAR groups, each optionally substituted as follows: (a) 1-5 halo groups, (b) 1 OH, $CO_2R^a$, CN, $S(O)_pR^d$, $NO_2$ or $C(O)NR^bR^c$ group, (c) 1-2 $C_{1-10}$alkyl or alkoxy groups, each optionally substituted with: 1-5 halo, up to perhaloalkyl, and 1-2 OH or $CO_2R^a$ groups; and (d) 1-2 phenyl rings, each of which is optionally substituted as follows: 1-5 halo groups up to perhalo, 1-3 $C_{1-10}$alkyl or alkoxy groups, each being further optionally substituted with 1-5 halo up to perhalo, or 1-2 hydroxy or $CO_2R^a$ groups; (e) $-NR^a-C(O)-NR^bR^c$; (f) $-NR^a-CO_2R^c$; (g) $-NR^a-C(O)R^c$; (h) $-NR^bR^c$; (i) $-NR^aSO_2R^c$; (j) $-SO_2-NR^bR^c$; (k) $-C(O)NR^bR^c$ and (1) $-OC(O)-NR^bR^c$;
- c) Aryl, HAR, Hetcy, $-O$-Aryl, $-O$-HAR and $-O$-Hetcy, each optionally substituted as set forth below: (1) 1-3 $C_{1-10}$alkyl, $C_{2-10}$alkenyl or $C_{2-10}$alkynyl groups optionally substituted with 1-5 halo groups; 1-2 OH groups; phenyl optionally substituted with 1-3 halo, $C_{1-6}$ alkyl or $C_{1-6}$ alkoxy groups, the alkyl and alkoxy groups being further optionally substituted with 1-3 halo groups; $CO_2R^a$; CN or $S(O)_pR^d$ groups; and (2) 1-3 $C_{1-10}$alkoxy groups, the alkyl portion of which is optionally substituted with 1-5 halo groups, 1-2 OH; phenyl optionally substituted with 1-3 halo, $C_{1-6}$ alkyl or $C_{1-6}$ alkoxy groups, the alkyl and alkoxy groups being further optionally substituted with 1-3 halo groups; $CO_2R^a$; CN or $S(O)_pR^d$ groups;

said Aryl, HAR, Hetcy $-O$-Aryl, $-O$-HAR and $-O$-Hetcy group c) being further optionally substituted on carbon by a group selected from the group consisting of: (3) 1-5 halo groups; (4) 1-2 OH groups; (5) 1 $S(O)_pR^d$, $NO_2$ or CN group; (6) 1-2 $CO_2R^a$; (7) $-NR^a-C(O)-NR^bR^c$; (8) $-NR^a-CO_2R^c$; (9) $-NR^a-C(O)R^c$; (10) $-NR^bR^c$; (11) $-NR^aSO_2R^c$; (12) $-SO_2-NR^bR^c$; and (13) $-C(O)NR^bR^c$; and when $R^1$ represents Hetcy containing a nitrogen atom, said nitrogen atom can be optionally substituted with a member selected from the group consisting of: (a) $-C(O)NR^bR^c$; (b) $-CO_2R^c$; (c) $-C(O)R^c$; and (d) $-SO_{2R}{}^c$;

each $R^2$ represents H or is independently selected from the group consisting of:
- a) OH, halo, $CO_2R^a$, $C(O)NR^bR^c$, $NR^bR^c$, CN or $S(O)_pR^d$;
- b) $C_{1-10}$alkyl, $C_{2-10}$alkenyl, $C_{2-10}$alkynyl, $OC_{1-10}$alkyl, $OC_{3-10}$alkenyl and $OC_{3-10}$alkynyl, said groups being optionally substituted with: (1) 1-5 halo groups up to a perhaloalkyl group; (2) 1 oxo group; (3) 1 OH group; (4) 1 $C_{1-10}$alkoxy group, each optionally substituted with: up to five halo or a perhaloalkoxy, 1 OH or $CO_2R^a$ group; (5) 1 $CO_2R^a$ or $S(O)_pR_d$; (6) 1 Aryl, Hetcy or HAR group, each optionally substituted as follows: (a) 1-5 halo groups, (b) 1 OH, $CO_2R^a$, CN, $S(O)_pR^d$, $NO_2$ or $C(O)NR^bR^c$ group, (c) 1-2 $C_{1-10}$alkyl or alkoxy groups, each optionally substituted with: 1-5 halo, up to perhaloalkyl, and 1-2 OH or $CO_2R^a$ groups; and (d) 1-2 phenyl rings, each of which is optionally substituted as follows: 1-5 halo groups up to perhalo; 1-3 $C_{1-10}$alkyl or alkoxy groups, each being further optionally substituted with 1-5 halo up to perhalo; and 1-2 hydroxy or $CO_2R^a$ groups;
- c) Aryl, HAR, Hetcy, $-O$-Aryl, $-O$-HAR and $-O$-Hetcy, each optionally substituted as set forth below: (1) 1-3 $C_{1-10}$alkyl, $C_{2-10}$alkenyl or $C_{2-10}$alkynyl groups optionally substituted with 1-5 halo groups, 1-2 OH, phenyl, $CO_2R^a$, CN or $S(O)_pR^d$ groups; (2) 1-3 $C_{1-10}$alkoxy groups, the alkyl portion of which is optionally substituted with 1-5 halo groups, 1-2 OH, phenyl, $CO_2R^a$, CN or $S(O)_pR^d$ groups;

said Aryl, HAR or Hetcy group c) being further optionally substituted on carbon by a group selected from the group consisting of, (3) 1-5 halo groups up to perhalo; (4) 1 OH group; (5) 1 $S(O)_pR_d$, $NO_2$ or CN group; (6) 1 $CO_2R^a$;

$R^3$ represents H or is selected from the group consisting of: a) $C_{1-10}$alkyl or $C_{2-10}$alkenyl, each optionally substituted with 1-5 halo groups up to perhalo; 1-2 OH, $C_{1-3}$alkoxy or haloC$_{1-3}$alkoxy groups; 1-2 $NR^cR^d$ groups; and 1-2 Aryl, HAR or Hetcy groups, each optionally substituted with 1-3 halo groups and 1-2 groups selected from CN, $NO_2$, $C_{1-3}$alkyl, haloC$_{1-3}$alkyl, $C_{1-3}$alkoxy and haloC$_{1-3}$ alkoxy groups; and b) Aryl, HAR or Hetcy, each optionally substituted with 1-3 halo groups and 1-2 groups selected from CN, $NO_2$, $C_{1-3}$alkyl, haloC$_{1-3}$alkyl, $C_{1-3}$alkoxy and haloC$_{1-3}$ alkoxy groups;

$R^4$ is independently selected from the group consisting of:
- a) $C_{1-14}$alkyl, $C_{2-10}$alkenyl and $C_{2-10}$alkynyl, said groups being optionally substituted with: (1) 1-5 halo groups up to perhaloalkyl; (2) 1 oxo group; (3) 1-2 OH groups; (4) 1-2 $C_{1-10}$alkoxy groups, each optionally substituted with up to five halo or a perhaloalkoxy, 1 OH or $CO_2R^a$ group; (5) 1 $CO_2R^a$ or $S(O)_pR^d$; (6) 1-2 Aryl, Hetcy or HAR groups, each optionally substituted as follows: (i) 1-5 halo groups, (ii) 1 OH, $CO_2R^a$, CN, $S(O)_pR^d$, $NO_2$ or $C(O)NR^bR^c$ group, (iii) 1-2 $C_{1-10}$alkyl or alkoxy groups, each optionally substituted with: 1-5 halo, up to perhaloalkyl, and 1-2 OH or $CO_2R^a$ groups; and (iv) 1-2 phenyl rings, each of which is optionally substituted as follows: 1-5 halo groups up to perhalo; 1-3 $C_{1-10}$alkyl or alkoxy groups, each being further optionally substituted with 1-5 halo up to perhalo, or 1-2 hydroxy or $CO_2R^a$ groups;

b) Aryl, HAR or Hetcy, each optionally substituted as follows: (1) 1-3 $C_{1-14}$alkyl, $C_{2-10}$alkenyl or $C_{2-10}$alkynyl groups optionally substituted with 1-5 halo groups, 1-2 OH, $CO_2R^a$, CN or $S(O)_pR^d$ groups or phenyl optionally substituted as follows: 1-5 halo groups up to perhalo; 1-3 $C_{1-10}$alkyl or alkoxy groups, each being further optionally substituted with 1-5 halo up to perhalo, or 1-2 hydroxy or $CO_2R^a$ groups; (2) 1-3 $C_{1-10}$alkoxy groups, the alkyl portion of which is optionally substituted with 1-5 halo groups, 1-2 OH, $CO_2R^a$, CN, $S(O)_pR^d$, and phenyl optionally substituted as follows: 1-5 halo groups up to perhalo; 1-3 $C_{1-10}$alkyl or alkoxy groups, each being further optionally substituted with 1-5 halo up to perhalo, or 1-2 hydroxy or $CO_2R^a$ groups; (3) 1-2 Aryl, HAR or Hetcy, OAryl, OHAR or OHetcy groups, each optionally substituted as follows: (i) 1-3 halo groups; (ii) 1-2 $C_{1-10}$alkyl, $C_{2-10}$alkenyl or $C_{2-10}$alkynyl groups each optionally substituted with 1-5 halo groups, 1-2 OH, phenyl, $CO_2R^a$, CN or $S(O)_pR^d$ groups; (iii) 1-2 $C_{1-10}$alkoxy groups the alkyl portion of which being optionally substituted with 1-5 halo groups, 1-2 OH, phenyl, $CO_2R^a$, CN or $S(O)_pR^d$ groups; and (iv) 1-2 $CO_2R^a$, $S(O)_pR^d$, CN, $NR^bR^c$, $NO_2$ or OH groups;

said Aryl, HAR or Hetcy group b) being further optionally substituted on carbon by a group selected from the group consisting of: (4) 1-5 halo groups; (5) 1-2 OH groups; (6) 1 $S(O)_pR^d$, $NO_2$ or CN group; (7) 1-2 $CO_2R^a$; (8) —$NR^a$—C(O)—$NR^bR^c$; (9) —$NR^a$—$CO_2R^c$; (10) —$NR^a$—C(O)$R^c$; (11) —$NR^bR^c$; (12) —$NR^aSO_2R^c$; (13) —$SO_2NR^bR^c$; (14) —C(O)$NR^bR^c$ and —OC(O)—$NR^bR^c$;

and when $R^4$ represents Hetcy containing a nitrogen atom, said nitrogen atom can be optionally substituted with a member selected from the group consisting of: (a) —C(O) $NR^bR^c$; (b) —$CO_2R^c$; (c) —C(O)$R^c$; and (d) —$SO_2R^c$;

$R^5$ represents H or $C_{1-6}$alkyl;

$R^6$ is selected from the group consisting of H, OH, F or $C_{1-3}$alkyl;

$R^7$ is H or F, or $R^6$ and $R^7$ are taken in combination and represent oxo;

$R^8$ represents H or $C_{1-6}$alkyl, optionally substituted with OH and 1-5 halo groups up to perhalo;

$R^9$ represents H, halo, OH, $C_{1-6}$alkyl, optionally substituted with 1-5 halo groups up to perhalo, or $C_{1-6}$alkoxy, optionally substituted with 1-3 halo groups up to perhalo, or when $R^9$ is ortho to the benzylic group, $R^8$ and $R^9$ can be taken together and represent a —$(CH_2)_{2-4}$— or a —O—$(CH_2)_{1-3}$— group;

$R^a$ is H or $C_{1-10}$alkyl, optionally substituted with phenyl, OH, $OC_{1-6}$alkyl, $CO_2H$, $CO_2C_{1-6}$alkyl and 1-3 halo groups;

$R^b$ is H or $C_{1-10}$alkyl;

$R^c$ is H or is independently selected from: (a) $C_{1-10}$alkyl, optionally substituted with OH, $OC_{1-6}$alkyl, $CO_2H$, $CO_2C_{1-6}$alkyl, and 1-3 halo groups; (b) Aryl or Ar—$C_{1-6}$alkyl, each optionally substituted with 1-5 halos and 1-3 members selected from the group consisting of: CN, OH, $C_{1-10}$alkyl and $OC_{1-10}$alkyl, said alkyl and alkoxy being further optionally substituted with 1-5 halo groups up to perhalo; (c) Hetcy or Hetcy-$C_{1-6}$alkyl, optionally substituted with 1-5 halo groups and 1-3 groups selected from: oxo, $C_{1-10}$alkyl and $OC_{1-10}$alkyl, said alkyl and alkoxy being further optionally substituted with 1-5 halo groups up to perhalo; and (d) HAR or HAR-$C_{1-6}$alkyl, optionally substituted with 1-5 halo groups and 1-3 groups selected from: $C_{1-10}$alkyl and $OC_{1-10}$alkyl, said alkyl and alkoxy being further optionally substituted with 1-5 halo groups up to perhalo;

$R^d$ is $C_{1-10}$alkyl, Aryl or Ar—$C_{1-10}$alkyl;

m is an integer selected from 0, 1 and 2;

n is an integer selected from 0 to 6;

p is an integer selected from 0, 1 and 2, and when at least one of m and n is other than 0, Z is selected from $CO_2R^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl).

2. A compound in accordance with claim 1 wherein $R^1$ represents H.

3. A compound in accordance with claim 1 wherein one $R^2$ represents H, halo or $C_{1-6}$alkyl, and the other is selected from the group consisting of: H, halo, OH, $C_{1-6}$alkyl optionally substituted with 1-3 halo groups, $C_{1-6}$alkoxy optionally substituted with 1-3 halo groups or 1 phenyl or heterocyclic ring, $C_{2-4}$alkenyl or $OC_{2-4}$alkenyl.

4. A compound in accordance with claim 1 wherein R3 is selected from the group consisting of: H, C2-4alkenyl and C1-6alkyl optionally substituted as follows: a) up to 3 halo groups; b) NRcRd wherein Rc and Rd are H or C1-4 alkyl; c) OH; and d) Aryl optionally substituted with 1-3 halo groups, C1-3 alkyl, OC1-3alkyl, CN, NO2, haloC1-3alkyl or O-haloC1-3alkyl.

5. A compound in accordance with claim 1 wherein $R^4$ is independently selected from the group consisting of:

(a) $C_{1-14}$alkyl, optionally substituted with: (1) 1-5 halo groups up to perhaloalkyl; (2) 1-2 $C_{1-10}$alkoxy groups, each optionally substituted with 1-5 halo groups up to perhaloalkoxy; (3) 1-2 Aryl groups, each optionally substituted as follows: (i) 1-5 halo groups, (ii) CN or $NO_2$, (iii) 1-2 $C_{1-10}$alkyl or alkoxy groups, each optionally substituted with: 1-5 halo, up to perhaloalkyl; and (b) Aryl, HAR or Hetcy, each optionally substituted as follows: (1) 1-2 $C_{1-10}$alkyl or $C_{2-10}$alkenyl groups, optionally substituted with 1-5 halo groups, phenyl or $CO_2R^a$ groups; (2) 1-2 $C_{1-10}$alkoxy groups, the alkyl portion of which is optionally substituted with 1-5 halo groups; (3) 1-2 Aryl, HAR or Hetcy, OAryl, OHAR or OHetcy groups, each optionally substituted as follows: (i) 1-3 halo groups; (ii) 1-2 $C_{1-10}$alkyl or $C_{2-10}$alkenyl, each optionally substituted with 1-3 halo groups; (iii) 1-2 $C_{1-10}$alkoxy groups the alkyl portion of which being optionally substituted with 1-3 halo groups, and (iv) 1-2 $CO_2R^a$, $S(O)_pR^d$, CN, $NR^bR^c$, $NO_2$ or OH groups;

said Aryl, HAR or Hetcy group b) being further optionally substituted on carbon by a group selected from the group consisting of: (4) 1-5 halo groups; (5) 1-2 OH groups; (6) 1 $S(O)_pR^d$, $NO_2$ or CN group; (7) 1-2 $CO_2R^a$; (8) —$NR^a$—C(O)—$NR^bR^c$; (9) —$NR^a$—$CO_2R^c$; (10) —$NR^a$—C(O)$R^c$; (11) —$NR^bR^c$; (12) —$NR^aSO_2R^c$; (13) —$SO_2$—$NR^bR^c$; (14) —C(O) $NR^bR^c$ and (15) —OC(O)$NR^bR^c$;

and when $R^4$ represents Hetcy containing a nitrogen atom, said nitrogen atom can be optionally substituted with a member selected from the group consisting of: (a) —C(O) $NR^bR^c$; (b) —$CO_2R^c$; (c) —C(O)$R^c$; and (d) —$SO_2R^c$.

6. A compound represented by formula I:

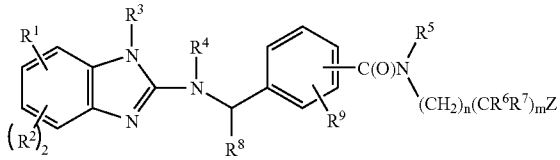

or a pharmaceutically acceptable salt thereof, wherein:
R$^1$ represents H;
one R$^2$ represents H, halo or C$_{1-6}$alkyl, and the other is selected from the group consisting of: H, halo, OH, C$_{1-6}$alkyl optionally substituted with 1-3 halo groups, C$_{1-6}$alkoxy optionally substituted with 1-3 halo groups or 1 phenyl or heterocyclic ring, C$_{2-4}$aalkenyl or OC$_{2-4}$alkenyl;
R$^3$ is selected from the group consisting of: H, C$_{2-4}$alkenyl and C$_{1-6}$alkyl optionally substituted as follows: a) up to 3 halo groups; b) NR$^c$R$^d$ wherein R$^c$ and R$^d$ are H or C$_{1-4}$alkyl; c) OH; and d) Aryl optionally substituted with 1-3 halo groups, C$_{1-3}$ alkyl, OC$_{1-3}$alkyl, CN, NO$_2$, haloC$_{1-3}$alkyl or O-haloC$_{1-3}$alkyl;
R$^4$ is independently selected from the group consisting of:
(a) C$_{1-14}$alkyl, optionally substituted with: (1) 1-5 halo groups up to perhaloalkyl; (2) 1-2 C$_{1-10}$alkoxy groups, each optionally substituted with 1-5 halo groups up to perhaloalkoxy; (3) 1-2 Aryl groups, each optionally substituted as follows: (i) 1-5 halo groups, (ii) CN or NO$_2$, (iii) 1-2 C$_{1-10}$alkyl or alkoxy groups, each optionally substituted with: 1-5 halo, up to perhaloalkyl; and
(b) Aryl, HAR or Hetcy, each optionally substituted as follows: (1) 1-2 C$_{1-10}$alkyl or C$_{2-10}$alkenyl, optionally substituted with 1-5 halo groups, phenyl or C$_2$R$^a$ groups; (2) 1-2 C$_{1-10}$alkoxy groups, the alkyl portion of which is optionally substituted with 1-5 halo groups; (3) 1-2 Aryl, HAR or Hetcy, OAryl, OHAR or OHetcy groups, each optionally substituted as follows: (i) 1-3 halo groups; (ii) 1-2 C$_{1-10}$alkyl or C$_{2-10}$alkenyl, each optionally substituted with 1-3 halo groups; (iii) 1-2 C$_{1-10}$alkoxy groups the alkyl portion of which being optionally substituted with 1-3 halo groups, and (iv) 1-2 CO$_2$R$^a$, S(O)$_p$R$^d$, CN, NR$^b$R$^c$, NO$_2$ or OH groups;
said Aryl, HAR or Hetcy group b) being further optionally substituted on carbon by a group selected from the group consisting of: (4) 1-5 halo groups; (5) 1-2 OH groups; (6) 1 S(O)$_p$R$^d$, NO$_2$ or CN group; (7) 1-2 CO$_2$R$^a$; (8) —NR$^a$, —C(O)—NR$^b$R$^c$; (9) —NR$^a$—CO$_2$R$^c$; (10) —NR$^a$—C(O)R$^c$; (11) —NR$^b$R$^c$; (12) —NR$^a$SO$_2$R$^c$; (13) —SO$_2$—NR$^b$R$^c$; (14) —C(O) NR$^b$R$^c$ and (15) —OC(O)—NR$^b$R$^c$;
and when R$^4$ represents Hetcy containing a nitrogen atom, said nitrogen atom can be optionally substituted with a member selected from the group consisting of: —C(O)NR$^b$R$^c$; (b) —CO$_2$R$^c$; (c) —C(O)R$^c$; and (d) —SO$_2$R$^c$;
R$^8$ represents H or C$_{1-6}$ alkyl;
R$^9$ represents H or halo;
R$^5$ represents H or C$_{1-6}$ alkyl;
R$^6$ is selected from the group consisting of H, OH, F or C$_{1-3}$alkyl;
R$^7$ is H or F, or R$^6$ and R$^7$ are taken in combination and represent oxo;

R$^a$ is H or C$_{1-10}$alkyl, optionally substituted with phenyl, OH, OC$_{1-6}$alkyl, CO$_2$H, CO$_2$C$_{1-6}$alkyl and 1-3 halo groups;
R$^b$ is H or C$_{1-10}$alkyl;
R$^c$ is H or is independently selected from: (a) C$_{1-10}$alkyl, optionally substituted with OH, OC$_{1-6}$alkyl, CO$_2$H, CO$_2$C$_{1-6}$alkyl, and 1-3 halo groups; (b) Aryl or Ar—C$_{1-6}$alkyl, each optionally substituted with 1-5 halos and 1-3 members selected from the group consisting of: CN, OH, C$_{1-10}$alkyl and OC$_{1-10}$ alkyl, said alkyl and alkoxy being further optionally substituted with 1-5 halo groups up to perhalo; (c) Hetcy or Hetcy-C$_{1-6}$alkyl, optionally substituted with 1-5 halo groups and 1-3 groups selected from: oxo, C$_{1-10}$alkyl and OC$_{1-10}$ alkyl, said alkyl and alkoxy being further optionally substituted with 1-5 halo groups up to perhalo; and (d) HAR or HAR-C$_{1-6}$alkyl, optionally substituted with 1-5 halo groups and 1-3 groups selected from: C$_{1-10}$alkyl and OC$_{1-10}$alkyl, said alkyl and alkoxy being further optionally substituted with 1-5 halo groups up to perhalo;
R$^d$ is C$_{1-10}$alkyl, Aryl or Ar—C$_{1-10}$alkyl;
m is an integer selected from 0, 1 and 2;
n is an integer selected from 0 to 6;
p is an integer selected from 0, 1 and 2, and
when at least one of m and n is other than 0, Z is selected from CO$_2$R$^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl).

7. A compound represented by formula I:

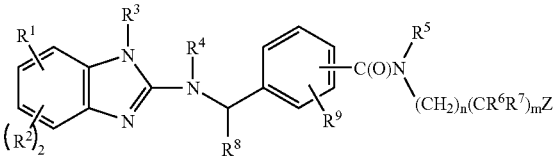

or a pharmaceutically acceptable salt thereof, wherein:
R$^1$ represents H;
one R$^2$ represents H, halo or C$_{1-6}$alkyl, and the other is selected from the group consisting of: H, halo, OH, C$_{1-6}$alkyl optionally substituted with 1-3 halo groups, C$_{1-6}$alkoxy optionally substituted with 1-3 halo groups or 1 phenyl or heterocyclic ring, C$_{2-4}$alkenyl or OC$_{2-4}$alkenyl;
R$^3$ is selected from the group consisting of: H, C$_{2-4}$alkenyl and C$_{1-6}$alkyl optionally substituted as follows: a) up to 3 halo groups; b) NR$^c$R$^d$ wherein R$^c$ and R$^d$ are H or C$_{1-4}$alkyl; c) OH; and d) Aryl optionally substituted with 1-3 halo groups, C$_{1-3}$alkyl, OC$_{1-3}$alkyl, CN, NO$_2$, haloC$_{1-3}$alkyl or O-haloC$_{1-3}$alkyl;
R$^4$ is independently selected from the group consisting of:
a) C$_{1-14}$alkyl, optionally substituted with: (1) 1-5 halo groups up to perhaloalkyl; (2) 1-2 C$_{1-10}$alkoxy groups, each optionally substituted with 1-5 halo groups up to perhaloalkoxy; (3) 1-2 Aryl groups, each optionally substituted as follows: (i) 1-5 halo groups, (ii) CN or NO$_2$, and (iii) 1-2 C$_{1-10}$alkyl or alkoxy groups, each optionally substituted with: 1-5 halo, up to perhaloalkyl; and
b) Aryl, HAR or Hetcy, each optionally substituted as follows: (1) 1-2 C$_{1-10}$alkyl or C$_{2-10}$alkenyl, optionally substituted with 1-5 halo groups, phenyl or CO$_2$R$^a$ groups; (2) 1-2 C$_{1-10}$alkoxy groups, the alkyl portion of which is optionally substituted with 1-5 halo groups; (3)

1-2 Aryl, HAR or Hetcy, OAryl, OHAR or OHetcy groups, each optionally substituted as follows: (a) 1-3 halo groups; (b) 1-2 $C_{1-10}$alkyl or $C_{2-10}$alkenyl, each optionally substituted with 1-3 halo groups; (c) 1-2 $C_{1-10}$alkoxy groups the alkyl portion of which being optionally substituted with 1-3 halo groups, and (d) 1-2 $CO_2R^a$, $S(O)_pR^d$, CN, $NR^bR^c$, $NO_2$ or OH groups; said Aryl, HAR or Hetcy group b) being further optionally substituted on carbon by a group selected from the group consisting of: (4) 1-5 halo groups; (5) 1-2 OH groups; (6) 1 $S(O)_pR^d$, $NO_2$ or CN group; (7) 1-2 $CO_2R^a$; (8) $-NR^a-C(O)-NR^bR^c$; (9) $-NR^a-CO_2R^c$; (10) $-NR^a-C(O)R^c$; (11) $-NR^bR^c$; (12) $-NR^aSO_2R^c$; (13) $-SO_2-NR^bR^c$; (14) $-C(O)-NR^bR^c$ and (15) $-OC(O)-NR^bR^c$;

and when $R^4$ represents Hetcy containing a nitrogen atom, said nitrogen atom can be optionally substituted with a member selected from the group consisting of: (a) $-C(O) NR^bR^c$; (b) $-CO_2R^c$; (c) $-C(O)R^c$; and (d) $-SO_2R^c$;

$R^8$ and $R^9$ are taken in combination and represent $-(CH_2)_{2-4}$;

$R^5$ represents H or $C_{1-6}$ alkyl;

$R^6$ is selected from the group consisting of H, OH, F or $C_{1-3}$alkyl;

$R^7$ is H or F, or $R^6$ and $R^7$ are taken in combination and represent oxo;

$R^a$ is H or $C_{1-10}$alkyl, optionally substituted with phenyl, OH, $OC_{1-6}$alkyl, $CO_2H$, $CO_2C_{1-6}$alkyl and 1-3 halo groups;

$R^b$ is H or $C_{1-10}$alkyl;

$R^c$ is H or is independently selected from: (a) $C_{1-10}$alkyl, optionally substituted with OH, $OC_{1-6}$alkyl, $CO_2H$, $CO_2C_{1-6}$alkyl, and 1-3 halo groups; (b) Aryl or Ar—$C_{1-6}$ alkyl, each optionally substituted with 1-5 halos and 1-3 members selected from the group consisting of: CN, OH, $C_{1-10}$alkyl and $OC_{1-10}$ alkyl, said alkyl and alkoxy being further optionally substituted with 1-5 halo groups up to perhalo; (c) Hetcy or Hetcy-$C_{1-6}$alkyl, optionally substituted with 1-5 halo groups and 1-3 groups selected from: oxo, $C_{1-10}$alkyl and $OC_{1-10}$ alkyl, said alkyl and alkoxy being further optionally substituted with 1-5 halo groups up to perhalo; and (d) HAR or HAR-$C_{1-6}$alkyl, optionally substituted with 1-5 halo groups and 1-3 groups selected from: $C_{1-10}$alkyl and $OC_{1-10}$ alkyl, said alkyl and alkoxy being further optionally substituted with 1-5 halo groups up to perhalo;

$R^d$ is $OC_{1-10}$alkyl, Aryl or Ar—$C_{1-10}$alkyl;

m is an integer selected from 0, 1 and 2;

n is an integer selected from 0 to 6;

p is an integer selected from 0, 1 and 2, and when at least one of m and n is other than 0, Z is selected from $CO_2R^a$, 5-tetrazolyl and 5-(2-oxo-1,3,4-oxadiazolyl), and when both m and n are 0, Z is selected from 5-tetrazolyl and 5-(2-oxo-1,3,4-oxadiazolyl).

8. A compound in accordance with claim 1 falling within table A below:

TABLE A

Key to Compounds

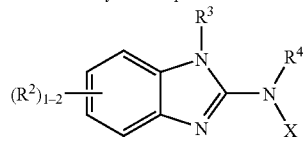

wherein $R^2$, $R^3$ and $R^4$ are in accordance with formula I and X is as shown below.

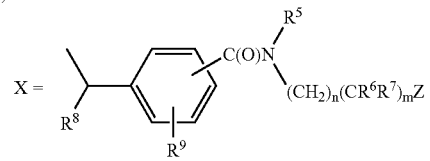

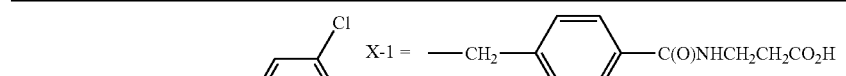

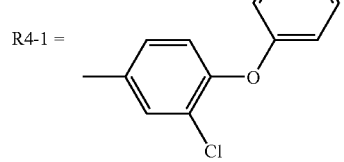

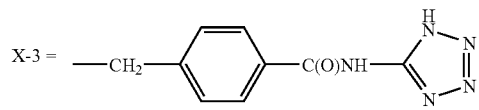

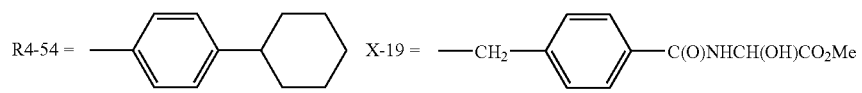

TABLE A-continued
Key to Compounds
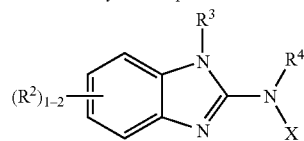
wherein $R^2$, $R^3$ and $R^4$ are in accordance with formula I and X is as shown below.
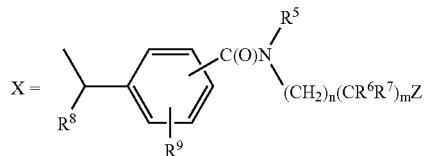
| | | | |
|---|---|---|---|
| R4-95 = | 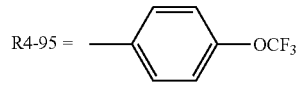 | X-21 = | 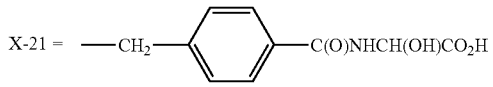 |
| R4-113 = | 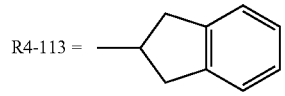 | X-29 = | 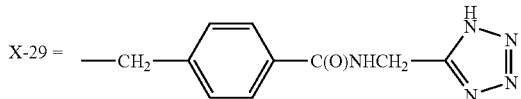 |
| R4-122 = | 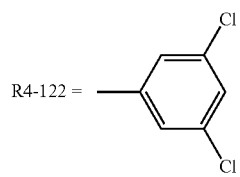 | X-70 = | 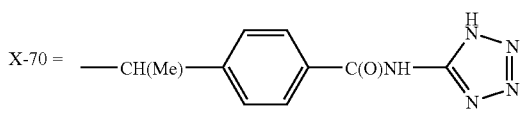 |
| R4-238 = | 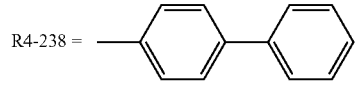 | X-85 = | 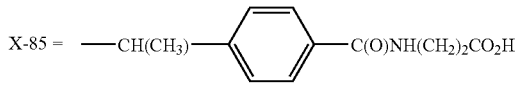 |
| R4-245 = | 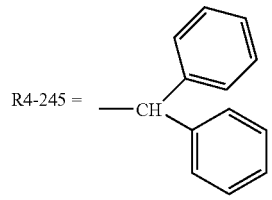 | X-86 = | 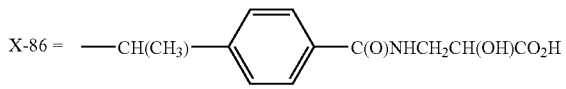 |
| R4-256 = | 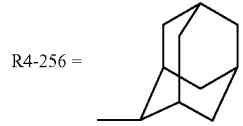 | X-226 = | 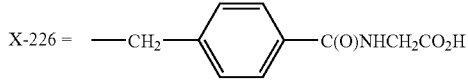 |
| R4-258 = | 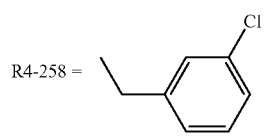 | X-227 = |  |
| R4-260 = | 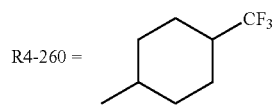 | X-237 = | 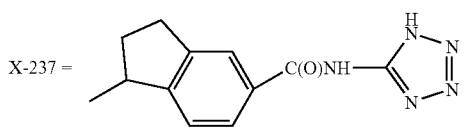 |

TABLE A-continued

Key to Compounds

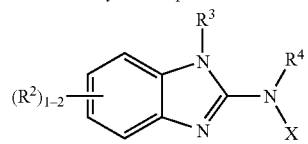

wherein $R^2$, $R^3$ and $R^4$ are in accordance with formula I and X is as shown below.

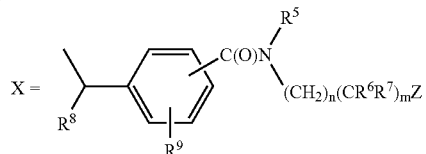

| | | | |
|---|---|---|---|
| R4-261 = | 4-bromophenyl-methyl | X-238 = | 1-methylindan-5-yl-C(O)NH—CH$_2$CH$_2$CO$_2$H |
| R4-262 = | 4-t-Bu-phenyl-methyl | X-239 = | 1-methylindan-5-yl-C(O)NH—CH$_2$CH(OH)CO$_2$H |
| R4-265 = | 4-chlorophenyl-ethyl | X-244 = | 4-ethyl-3-bromophenyl-C(O)NH-tetrazol-5-yl |
| R4-266 = | 2-chlorophenyl-ethyl | R4-267 = | 4-methylcyclohexyl-phenyl |
| R4-269 = | 6-fluoro-2-methyltetralin-yl | R4-273 = | 4-isopropyl-phenyl-methyl |
| R4-275 = | 3-phenylpropyl | R4-276 = | 4-phenylbutyl |
| R4-277 = | 5-phenylpentyl | R4-278 = | —(CH$_2$)$_2$-(4-chlorophenyl) |
| R4-282 = | 6-bromo-2-methyltetralin-yl | R4-284 = | 4-methylphenyl-cyclohexenyl |

TABLE A

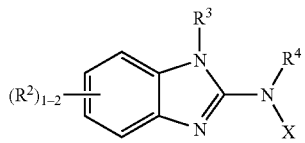

wherein

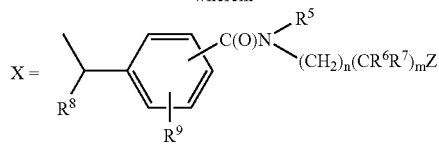

| Cpd No. | R² | R³ | R⁴ | X |
|---|---|---|---|---|
| 1 | 5-Me | H | R4-1 | X-1 |
| 2 | 5-Me | H | R4-2 | X-1 |
| 3 | 5-Me | H | R4-1 | X-3 |
| 4 | 5-Me | H | R4-2 | X-3 |
| 5 | 5-OCF₃ | H | R4-1 | X-1 |
| 6 | 5-OCF₃ | H | R4-2 | X-3 |
| 7 | 5-OCF₃ | H | R4-2 | X-1 |
| 8 | 6-Me | Me | R4-2 | X-3 |
| 9 | 5-Cl | H | R4-2 | X-3 |
| 10 | 5-Cl | H | R4-1 | X-3 |
| 11 | 6-Me | Me | R4-2 | X-1 |
| 12 | 5-Cl | H | R4-2 | X-1 |
| 13 | 5-Cl | H | R4-1 | X-1 |
| 14 | 5-Me | Me | R4-1 | X-3 |
| 15 | 5-Me | Me | R4-1 | X-1 |
| 16 | H | H | R4-2 | X-3 |
| 17 | H | H | R4-2 | X-1 |
| 18 | H | Me | R4-2 | X-1 |
| 19 | H | Me | R4-2 | X-19 |
| 20 | H | Me | R4-2 | X-3 |
| 21 | H | Me | R4-2 | X-21 |
| 22 | 6-Me | Me | R4-2 | X-21 |
| 23 | 5-Me | H | R4-2 | X-21 |
| 24 | H | Et | R4-2 | X-3 |
| 25 | H | Et | R4-2 | X-1 |
| 26 | H | Et | R4-2 | X-21 |
| 27 | H | n-Pr | R4-2 | X-3 |
| 28 | H | n-Pr | R4-2 | X-1 |
| 29 | H | n-Pr | R4-2 | X-29 |
| 30 | H | n-Pr | R4-2 | X-21 |
| 31 | 5-Me | H | R4-2 | X-29 |
| 32 | H | cPentyl | R4-2 | X-3 |
| 33 | H | cPentyl | R4-2 | X-1 |
| 34 | H | cPentyl | R4-2 | X-21 |
| 35 | H | Et | R4-2 | X-29 |
| 36 | H | Benzyl | R4-2 | X-3 |
| 37 | H | Benzyl | R4-2 | X-29 |
| 38 | H | Benzyl | R4-2 | X-1 |
| 39 | H | Benzyl | R4-2 | X-21 |
| 40 | H | —CH₂CH(Me)₂ | R4-2 | X-3 |
| 41 | H | —CH₂CH(Me)₂ | R4-2 | X-29 |
| 42 | H | —CH₂CH(Me)₂ | R4-2 | X-1 |
| 43 | H | —CH₂CH(Me)₂ | R4-2 | X-21 |
| 44 | H | H | R4-2 | X-29 |
| 45 | H | H | R4-2 | X-21 |
| 46 | H | Me | R4-2 | X-29 |
| 47 | H | CH₂CH₂F | R4-2 | X-3 |
| 48 | H | CH₂CH₂F | R4-2 | X-1 |
| 49 | H | CH₂CH₂F | R4-2 | X-21 |
| 50 | H | CH₂CH₂F | R4-2 | X-29 |
| 51 | H | CH₂CH=CH₂ | R4-2 | X-3 |
| 52 | H | CH₂CH=CH₂ | R4-2 | X-1 |
| 53 | H | CH₂CH=CH₂ | R4-2 | X-21 |
| 54 | H | H | R4-54 | X-3 |
| 55 | H | H | R4-54 | X-1 |
| 56 | H | H | R4-54 | X-21 |
| 57 | H | Me | R4-54 | X-3 |
| 58 | H | Me | R4-54 | X-1 |
| 59 | H | Me | R4-54 | X-21 |
| 60 | 5,6-di-Cl | H | R4-2 | X-3 |

TABLE A-continued

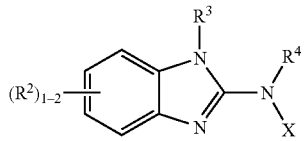

wherein

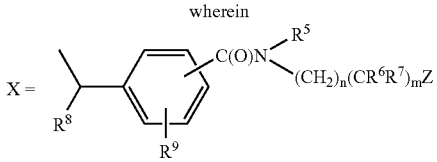

| Cpd No. | R² | R³ | R⁴ | X |
|---|---|---|---|---|
| 61 | 5,6-di-Cl | H | R4-2 | X-29 |
| 62 | 5,6-di-Cl | H | R4-2 | X-1 |
| 63 | 5,6-di-Cl | H | R4-2 | X-21 |
| 64 | 5,6-di-Cl | Et | R4-2 | X-3 |
| 65 | 5,6-di-Me | H | R4-2 | X-3 |
| 66 | 5,6-di-Me | H | R4-2 | X-29 |
| 67 | 5,6-di-Me | H | R4-2 | X-1 |
| 68 | 5,6-di-Me | H | R4-2 | X-21 |
| 69 | H | Me | R4-2 | X-70 |
| 70 | H | CH₂CH₂OH | R4-2 | X-3 |
| 71 | H | CH₂CH₂OH | R4-2 | X-1 |
| 72 | H | CH₂CH₂OH | R4-2 | X-21 |
| 73 | 5,6-di-Me | Me | R4-2 | X-3 |
| 74 | 5,6-di-Me | Me | R4-2 | X-29 |
| 75 | 5,6-di-Me | Me | R4-2 | X-1 |
| 76 | 5,6-di-Me | Me | R4-2 | X-21 |
| 77 | 5,6-di-Cl | Me | R4-2 | X-3 |
| 78 | 5,6-di-Cl | Me | R4-2 | X-1 |
| 79 | 5,6-di-Cl | Me | R4-2 | X-21 |
| 80 | 5,6-di-F | H | R4-2 | x-3 |
| 81 | 5,6-di-F | H | R4-2 | x-1 |
| 82 | 5,6-di-F | H | R4-2 | x-29 |
| 83 | 5,6-di-F | H | R4-2 | x-21 |
| 84 | H | Me | R4-2 | x-85 |
| 85 | H | Me | R4-2 | X-86 |
| 86 | 5,6-di-F | Me | R4-2 | X-3 |
| 87 | 5,6-di-F | Me | R4-2 | X-1 |
| 88 | 5,6-di-F | Me | R4-2 | X-21 |
| 89 | H | (CH₂)₃OH | R4-2 | X-3 |
| 90 | H | (CH₂)₃OH | R4-2 | X-21 |
| 91 | H | Me | R4-95 | X-3 |
| 92 | H | Me | R4-95 | X-21 |
| 93 | H | (CH₂)₂NMe₂ | R4-2 | X-3 |
| 94 | H | 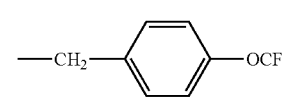 | R4-2 | X-3 |
| 95 | H | 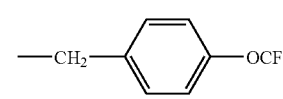 | R4-2 | X-21 |
| 96 | H | 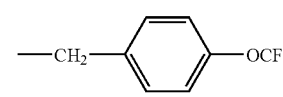 | R4-2 | X-1 |
| 97 | H | Phenyl | R4-2 | X-3 |
| 98 | H | Phenyl | R4-2 | X-29 |
| 99 | H | Phenyl | R4-2 | X-1 |
| 100 | H | Phenyl | R4-2 | X-21 |
| 101 | 6-allyloxy | Et | R4-2 | X-3 |
| 102 | 6-allyloxy | Et | R4-2 | X-1 |
| 103 | 6-allyloxy | Et | R4-2 | X-21 |
| 104 | 6-allyloxy | Et | R4-2 | X-29 |
| 105 | 5,6-di-F | Et | R4-2 | X-3 |
| 106 | H | Me | R4-113 | X-3 |
| 107 | 5,6-di-F | Et | R4-2 | X-21 |
| 108 | 6-OH | Et | R4-2 | X-3 |

TABLE A-continued wherein

X = [structure showing substituted phenyl with R8, R9, and C(O)N(R5)(CH2)n(CR6R7)mZ group]

| Cpd No. | R² | R³ | R⁴ | X |
|---|---|---|---|---|
| 109 | 6-OH | Et | R4-2 | X-1 |
| 110 | 5,6-di-F | Et | R4-2 | X-1 |
| 111 | 6-OH | Et | R4-2 | X-21 |
| 112 | 6-OH | Et | R4-2 | X-29 |
| 113 | 5-OMe | Me | R4-2 | X-3 |
| 114 | 5-OMe | Me | R4-2 | X-21 |
| 115 | 5-OMe | Me | R4-2 | X-1 |
| 116 | H | H | R4-122 | X-3 |
| 117 | H | H | R4-122 | X-1 |
| 118 | H | H | R4-122 | X-21 |
| 119 | H | H | R4-122 | X-29 |
| 120 | 5-OH | Me | R4-2 | X-3 |
| 121 | 5-OH | Me | R4-2 | X-1 |
| 122 | 5-OH | Me | R4-2 | X-21 |
| 123 | 5-allyloxy | Me | R4-2 | X-3 |
| 124 | 5-allyloxy | Me | R4-2 | X-1 |
| 125 | 5-benzyloxy | Me | R4-2 | X-3 |
| 126 | 5-benzyloxy | Me | R4-2 | X-1 |
| 127 | 6-allyloxy | Me | R4-2 | X-3 |
| 128 | 6-allyloxy | Me | R4-2 | X-1 |
| 129 | 6-allyloxy | Me | R4-2 | X-21 |
| 130 | 6-allyloxy | Me | R4-2 | X-29 |
| 131 | H | 4-Cl-phenyl-ethyl | R4-2 | X-3 |
| 132 | H | 3-Cl-phenyl-ethyl | R4-2 | X-3 |
| 133 | H | 2,4-diCl-phenyl-ethyl | R4-2 | X-3 |
| 134 | H | 4-Cl-phenyl-ethyl | R4-2 | X-21 |
| 135 | H | 3-Cl-phenyl-ethyl | R4-2 | X-21 |
| 136 | H | 2,4-diCl-phenyl-ethyl | R4-2 | X-21 |

TABLE A-continued

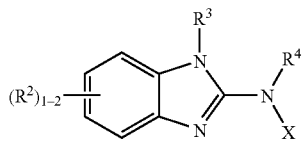

wherein

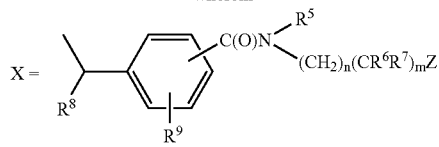

| Cpd No. | R² | R³ | R⁴ | X |
|---|---|---|---|---|
| 137 | H | (4-Cl-benzyl, ethyl) | R4-2 | X-1 |
| 138 | H | (3-Cl-benzyl, ethyl) | R4-2 | X-1 |
| 139 | H | (2,4-diCl-benzyl, ethyl) | R4-2 | X-1 |
| 140 | 6-OH | Me | R4-2 | X-3 |
| 141 | 6-OH | Me | R4-2 | X-1 |
| 142 | 6-OH | Me | R4-2 | X-21 |
| 143 | 6-OH | Me | R4-2 | X-29 |
| 144 | 5-n-propyloxy | Me | R4-2 | X-3 |
| 145 | 5-n-propyloxy | Me | R4-2 | X-29 |
| 146 | 5-n-propyloxy | Me | R4-2 | X-1 |
| 147 | 5-n-propyloxy | Me | R4-2 | X-21 |
| 148 | 5-isopropyloxy | Me | R4-2 | X-3 |
| 149 | 5-isopropyloxy | Me | R4-2 | X-29 |
| 150 | 5-isopropyloxy | Me | R4-2 | X-1 |
| 151 | 5-isopropyloxy | Me | R4-2 | X-21 |
| 152 | 6-n-propyloxy | Me | R4-2 | X-3 |
| 153 | 6-n-propyloxy | Me | R4-2 | X-1 |
| 154 | 6-n-propyloxy | Me | R4-2 | X-21 |
| 155 | 5-OMe | Me | R4-2 | X-29 |
| 156 | 5-cyclo-pentyloxy | Me | R4-2 | X-3 |
| 157 | 5-cyclo-pentyloxy | Me | R4-2 | X-29 |
| 158 | 5-OCH₂CH(Me)₂ | Me | R4-2 | X-3 |
| 159 | 5-OCH₂CH(Me)₂ | Me | R4-2 | X-29 |
| 160 | 6-benzyloxy | Me | R4-2 | X-3 |
| 161 | 6-isopropyloxy | Me | R4-2 | X-3 |
| 162 | 6-OMe | Me | R4-2 | X-3 |
| 163 | 6-benzyloxy | Me | R4-2 | X-1 |
| 164 | 6-isopropyloxy | Me | R4-2 | X-1 |
| 165 | 6-OMe | Me | R4-2 | X-1 |
| 166 | 6-benzyloxy | Me | R4-2 | X-21 |
| 167 | 6-isopropyloxy | Me | R4-2 | X-21 |
| 168 | 6-OMe | Me | R4-2 | X-21 |
| 169 | 5-benzyloxy | Me | R4-2 | X-21 |
| 170 | 5-cyclopentyloxy | Me | R4-2 | X-1 |
| 171 | 5-cyclopentyloxy | Me | R4-2 | X-21 |
| 172 | 5-isobutyloxy | Me | R4-2 | X-1 |
| 173 | 5-isobutyloxy | Me | R4-2 | X-21 |
| 174 | 6-allyloxy | Me | R4-113 | X-3 |
| 175 | 6-allyloxy | Me | R4-113 | X-1 |

TABLE A-continued
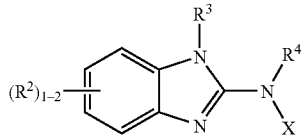
wherein
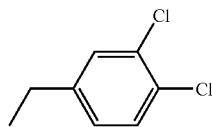
| Cpd No. | R² | R³ | R⁴ | X |
|---|---|---|---|---|
| 176 | H | 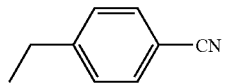 | R4-2 | X-3 |
| 177 | 6-allyloxy | Me | R4-113 | X-21 |
| 178 | H | 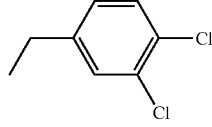 | R4-2 | X-3 |
| 179 | H | 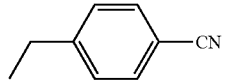 | R4-2 | X-21 |
| 180 | H | 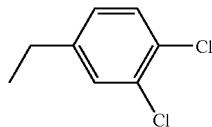 | R4-2 | X-21 |
| 181 | H | 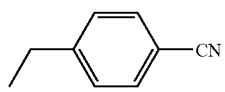 | R4-2 | X-1 |
| 182 | H | 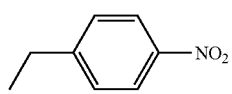 | R4-2 | X-1 |
| 183 | H | 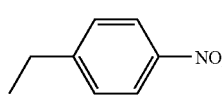 | R4-2 | X-3 |
| 184 | H | 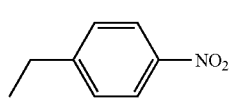 | R4-2 | X-21 |
| 185 | H | 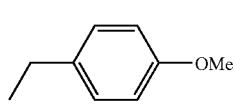 | R4-2 | X-1 |
| 186 | H |  | R4-2 | X-3 |

TABLE A-continued wherein

X = [structure showing phenyl group with R8, R9 substituents, C(O)N(R5)(CH2)n(CR6R7)mZ, and methyl branch]

| Cpd No. | R² | R³ | R⁴ | X |
|---|---|---|---|---|
| 187 | H | [4-OMe-phenyl-ethyl] | R4-2 | X-21 |
| 188 | H | [4-OMe-phenyl-ethyl] | R4-2 | X-1 |
| 189 | H | Me | R4-2 | X-237 |
| 190 | H | Me | R4-2 | X-238 |
| 191 | H | Me | R4-2 | X-239 |
| 192 | 6-cyclopentyloxy | Me | R4-2 | X-3 |
| 193 | 6-cyclopentyloxy | Me | R4-2 | X-1 |
| 194 | 6-cyclopentyloxy | Me | R4-2 | X-21 |
| 195 | 5-OMe | Me | R4-54 | X-3 |
| 196 | 5-OMe | Me | R4-54 | X-1 |
| 197 | 6-allyloxy | Me | R4-95 | X-3 |
| 198 | 6-allyloxy | Me | R4-95 | X-1 |
| 199 | 6-allyloxy | Me | R4-95 | X-21 |
| 200 | 6-OH | Me | R4-95 | X-3 |
| 201 | 5-OEt | Me | R4-2 | X-3 |
| 202 | 5-cyclobutyloxy | Me | R4-2 | X-3 |
| 203 | 5-cyclopropyl methoxy | Me | R4-2 | X-3 |
| 204 | 5-cyclopropyl methoxy | Me | R4-2 | X-1 |
| 205 | 5-cyclohexyl methoxy | Me | R4-2 | X-3 |
| 206 | 5-cyclohexyl methoxy | Me | R4-2 | X-1 |
| 207 | 5-OEt | Me | R4-2 | X-1 |
| 208 | 5-cyclobutyloxy | Me | R4-2 | X-1 |
| 209 | 5-OCH$_2$CHF$_2$ | Me | R4-2 | X-3 |
| 210 | 5-OCH$_2$CHF$_2$ | Me | R4-2 | X-1 |
| 211 | 5-cyclobutyl methoxy | Me | R4-2 | X-3 |
| 212 | 5-cyclobutyl methoxy | Me | R4-2 | X-1 |
| 213 | 5-cyclopentyl methoxy | Me | R4-2 | X-3 |
| 214 | 5-cyclopentyl methoxy | Me | R4-2 | X-1 |
| 215 | 6-n-propyloxy | Me | R4-95 | X-3 |
| 216 | 5-CF$_3$ | Me | R4-2 | X-3 |
| 217 | 6-benzyloxy | Me | R4-95 | X-3 |
| 218 | 5-CF$_3$ | Me | R4-2 | X-1 |
| 219 | 5-n-propyloxy | Me | R4-54 | X-3 |
| 220 | 6-n-propyloxy | Me | R4-95 | X-1 |
| 221 | 6-benzyloxy | Me | R4-95 | X-1 |
| 222 | 6-OEt | Me | R4-2 | X-3 |
| 223 | 6-cyclopropyl methoxy | Me | R4-2 | X-3 |
| 224 | 6-OCH$_2$CH(Me)$_2$ | Me | R4-2 | X-3 |
| 225 | 6-OEt | Me | R4-2 | X-1 |
| 226 | 6-cyclopropyl methoxy | Me | R4-2 | X-1 |
| 227 | 6-OCH$_2$CH(Me)$_2$ | Me | R4-2 | X-1 |
| 228 | H | Me | R4-54 | X-237 |

TABLE A-continued

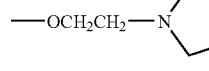

wherein

X =

| Cpd No. | R² | R³ | R⁴ | X |
|---|---|---|---|---|
| 229 | 5-Br | Me | R4-2 | X-3 |
| 230 | 5-Br | Me | R4-2 | X-1 |
| 231 | H | Et | R4-2 | X-226 |
| 232 | H | Et | R4-2 | X-227 |
| 233 | 6-OCH₂CHF₂ | Me | R4-2 | X-3 |
| 234 | 6-OCH₂CHF₂ | Me | R4-2 | X-1 |
| 235 | 5-OMe | Me | R4-2 | X-244 |
| 236 | H | Me | R4-245 | X-3 |
| 237 | 6-cyclohexyloxy | Me | R4-2 | X-3 |
| 238 | H | Me | R4-122 | X-3 |
| 249 | 5-n-propyloxy | Me | R4-2 | X-237 |
| 240 | 5-cyclopentyloxy | Me | R4-54 | X-3 |
| 241 | 5-cyclopentyloxy | Me | R4-54 | X-1 |
| 242 | 5-n-propyloxy | Me | R4-54 | X-1 |
| 243 | 6-cyclohexyl methoxy | Me | R4-2 | X-3 |
| 244 | 6-cyclohexyloxy | Me | R4-2 | X-1 |
| 245 | 6-cyclohexyl methoxy | Me | R4-2 | X-1 |
| 246 | H | Me | R4-256 | X-1 |
| 247 | 6- —OCH₂CH₂—N(pyrrolidine) | Me | R4-2 | X-3 |
| 248 | 5-OMe | Me | R4-258 | X-3 |
| 249 | 5-cyclopentyloxy | Me | R4-2 | X-244 |
| 250 | H | Me | R4-260 | X-3 |
| 251 | H | Me | R4-261 | X-3 |
| 252 | H | Me | R4-262 | X-3 |
| 253 | H | Me | R4-262 | X-1 |
| 254 | 5-OMe | Me | R4-122 | X-3 |
| 255 | 5-OMe | Me | R4-265 | X-3 |
| 256 | 5-OMe | Me | R4-266 | X-3 |
| 257 | H | Me | R4-267 | X-1 |
| 258 | H | Me | R4-267 | X-3 |
| 259 | H | Me | R4-269 | X-1 |
| 260 | H | Me | R4-269 | X-3 |
| 261 | H | Me | R4-238 | X-3 |
| 262 | H | Me | R4-238 | X-1 |
| 263 | H | Me | R4-273 | X-3 |
| 264 | H | Me | R4-273 | X-1 |
| 265 | H | Me | R4-275 | X-3 |
| 266 | H | Me | R4-276 | X-3 |
| 267 | H | Me | R4-277 | X-3 |
| 268 | H | Me | R4-278 | X-3 |
| 269 | H | Me | R4-278 | X-1 |
| 270 | 5-n-pentyloxy | Me | R4-122 | X-3 |
| 271 | 5-n-propyloxy | Me | R4-122 | X-3 |
| 272 | H | Me | R4-282 | X-1 |
| 273 | H | Me | R4-282 | X-3 |
| 274 | H | Me | R4-284 | X-3 |
| 275 | H | Me | R4-284 | X-1 |
| 276 | 5-OCF₃ | Me | R4-95 | X-3 |
| 277 | 5-CF₃ | Me | R4-95 | X-3 |
| 278 | 5-Cl | Me | R4-95 | X-3 |
| 279 | 5-OMe | Me | R4-95 | X-3 |

TABLE A-continued wherein

X = [structure: CH(R8)-phenyl(R9)-C(O)N(R5)-(CH2)n(CR6R7)mZ]

| Cpd No. | R² | R³ | R⁴ | X |
|---|---|---|---|---|
| 280 | 5-OMe | Me | R4-95 | X-1 |
| 281 | 5-n-propyloxy | Me | R4-95 | X-3 |
| 282 | 5-cyclopentyloxy | Me | R4-95 | X-3 | or a pharmaceutically acceptable salt thereof.

9. A pharmaceutical composition which is comprised of a compound in accordance with claim 1 in combination with a pharmaceutically acceptable carrier.

10. A method of treating type 2 diabetes mellitus in a mammalian patient in need of such treatment, comprising administering to said patient a compound in accordance with claim 1 in an amount that is effective to treat type 2 diabetes mellitus.

* * * * *